United States Patent
Bent

(10) Patent No.: US 10,195,219 B2
(45) Date of Patent: Feb. 5, 2019

(54) CANCER THERAPY

(71) Applicant: Rebecca Lambert Bent, Washington, CT (US)

(72) Inventor: Rebecca Lambert Bent, Washington, CT (US)

(73) Assignee: NED Biosystems, Inc., Walpole, MA (US)

( * ) Notice: Subject to any disclaimer, the term of this patent is extended or adjusted under 35 U.S.C. 154(b) by 0 days.

(21) Appl. No.: 14/351,766

(22) PCT Filed: Apr. 11, 2014

(86) PCT No.: PCT/US2014/033820
§ 371 (c)(1),
(2) Date: Apr. 14, 2014

(87) PCT Pub. No.: WO2014/169221
PCT Pub. Date: Oct. 16, 2014

(65) Prior Publication Data
US 2016/0030454 A1 Feb. 4, 2016

Related U.S. Application Data

(60) Provisional application No. 61/811,209, filed on Apr. 12, 2013.

(51) Int. Cl.
| | | |
|---|---|---|
| *A61K 31/664* | (2006.01) | |
| *A61K 31/12* | (2006.01) | |
| *A61K 31/485* | (2006.01) | |
| *A61K 31/155* | (2006.01) | |
| *A61K 31/385* | (2006.01) | |
| *A61K 31/352* | (2006.01) | |
| *A61K 45/06* | (2006.01) | |
| *A61K 31/198* | (2006.01) | |
| *A61K 31/4045* | (2006.01) | |
| *A61K 31/575* | (2006.01) | |
| *A61K 31/675* | (2006.01) | |
| *A61K 31/7048* | (2006.01) | |
| *A61K 38/33* | (2006.01) | |
| *A61K 38/08* | (2006.01) | |

(52) U.S. Cl.
CPC .......... *A61K 31/664* (2013.01); *A61K 31/12* (2013.01); *A61K 31/155* (2013.01); *A61K 31/198* (2013.01); *A61K 31/352* (2013.01); *A61K 31/385* (2013.01); *A61K 31/4045* (2013.01); *A61K 31/485* (2013.01); *A61K 31/575* (2013.01); *A61K 31/675* (2013.01); *A61K 31/7048* (2013.01); *A61K 38/08* (2013.01); *A61K 38/33* (2013.01); *A61K 45/06* (2013.01)

(58) Field of Classification Search
CPC .... A61K 31/12; A61K 31/664; A61K 31/485; A61K 31/155; A61K 31/385; A61K 31/352
See application file for complete search history.

(56) References Cited

U.S. PATENT DOCUMENTS

| | | | | |
|---|---|---|---|---|
| 4,888,346 A | * | 12/1989 | Bihari | A61K 31/485 514/282 |
| 2003/0078214 A1 | | 4/2003 | Kelly | |
| 2012/0059005 A1 | * | 3/2012 | Baselga | A61K 31/155 514/235.8 |
| 2012/0220664 A1 | * | 8/2012 | Struhl | A61K 31/155 514/635 |

FOREIGN PATENT DOCUMENTS

| | | |
|---|---|---|
| JP | 2004-2304 A | 1/2004 |
| WO | WO-01/78783 A2 | 10/2001 |
| WO | WO-2012/122295 A2 | 9/2012 |

OTHER PUBLICATIONS

Domont et al. ASCO Meeting, 2010, pp. 1-2.*
Dhingra et al. Int. J. Clin. Exp. Pathology, 2011, vol. 4, No. 2, pp. 134-146.*
Ipach et al., JCO, 2011, vol. 29, No. 33, pp. e799-e802.*
Gorski, David. Science e-Medicine, 2011, pp. 1-26.*
Kan et al. AntiCancer Research, 2012, vol. 32, pp. 5363-5370.*
Berkson et al. Integr. Cancer Ther., 2006, vol. 5, No. 1, pp. 83-89.*
Sadeghi et al. Clin. Cancer Res., 2012, vol. 18, No. 10, pp. 2905-2912.*
Donahue et al. (Experimental Biology and Medicine, 2011, vol. 236, pp. 883-895.*
Matulonis et al. Gynecologic Oncology, Apr. 6, 2012, vol. 126, pp. 41-46.*
Sarosy et al. Cancer, 2010, vol. 116, No. 6, pp. 1476-1484.*
Adams, C.P. and Brantner, V.V., Estimating the cost of new drug development: is it really 802 million?, Health Affairs, 25(2):420-428 (2006).
Aggarwal, B.B. et al., Curcumin: An Orally Bioavailable Blocker of TNF and Other Pro-inflammatory Biomarkers, British Journal of Pharmacology, 169:1672-1692 (2013).
Agrawal, Y.P., Low dose naltrexone therapy in multiple sclerosis, Med Hypotheses, 64(4):721-724 (2005).
Arendt, J., Safety of melatonin in long-term use (?), Journal of Biological Rhythms, 12(6):673-681 (1997).

(Continued)

*Primary Examiner* — Samira J Jean-Louis
(74) *Attorney, Agent, or Firm* — Choate, Hall & Stewart, LLP; Brenda Herschbach Jarrell; Stephanie L. Schonewald

(57) ABSTRACT

The present invention is directed to compositions and methods for the treatment of cancers, particularly cancers of epithelial origin. Therapy with a plurality of nutraceutical, non-chemotherapeutic and chemotherapeutic agents, that together target a plurality of cancer-supportive processes in a patient are disclosed. Among other things, the present invention encompasses the insight that redundant targeting of multiple such pathways provides effective treatment of various cancer, including late-stage cancers, metastasized cancers, and/or cancers that have failed treatment with traditional chemotherapy and/or other therapeutic modalities.

8 Claims, 1 Drawing Sheet

(56) References Cited

OTHER PUBLICATIONS

Author Not Known, CEA reduction to 6 in less than one month on low dose metronomic chemotherapy, retrieved on Jul. 11, 2014, http://www.humlegaarden.com.

Author Not Known, Excellent response in a breast cancer patient with lung metastases, retrieved on Jul. 11, 2014, http://www.humlegaarden.com.

Author Not Known, Harvard Palaver Series in Methods of Translational Science, retrieved on Jul. 11, 2014, http://1pm.hms.harvard.edu/palaver/sites/default/files/dr_Sukhatme.pdf.

Awwad, M. and North, R.J., Cyclophosphamide (Cy)—facilitated adoptive immunotherapy of a Cy-resistant tumour. Evidence that Cy permits the expression of adoptive T-cell mediated immunity by removing suppressor T cells rather than by reducing tumour burden, Immunology, 65(1):87-92 (1988).

Bayet-Robert, M. et al., Phase I dose escalation trial of docetaxel plus curcumin in patients with advanced and metastatic breast cancer, Cancer Biol Ther, 9(1):8-14 (2010).

Belcaro, G. et al., Efficacy and safety of Meriva®, a curcumin-phosphatidylcholine complex, during extended administration in osteoarthritis patients, Altern Med Rev, 15(4):337-344 (2010).

Bertolini, F. et al., Maximum tolerable dose and low-dose metronomic chemotherapy have opposite effects on the mobilization and viability of circulating endothelial progenitor cells, Cancer Res, 63(15):4342-4346 (2003).

Bocci, G. et al., Thrombospondin 1, a mediator of the antiangiogenic effects of low-dose metronomic chemotherapy, Proc Natl Acad Sci USA, 100(22):12917-12922 (2003).

Boehm, T. et al., Antiangiogenic therapy of experimental cancer does not induce acquired drug resistance, Nature, 390:404-407 (1997).

Brock, D.W., Ethical and value issues in insurance coverage for cancer treatment, Oncologist, 1:36-42 (2010).

Browder, T. et al., Antiangiogenic scheduling of chemotherapy improves efficacy against experimental drug-resistant cancer, Cancer Res, 60:1878-1886 (2000).

Buckstein, R. et al., High-Dose Celecoxib and Metronomic "Low-dose" Cyclophosphamide Is an Effective and Safe Therapy in Patients with Relapsed and Refractory Aggressive Histology Non-Hodgkins' Lymphoma, Clin. Cancer Res., 12(17): 5190-5198 (2006).

Buscemi, N. et al., The efficacy and safety of exogenous melatonin for primary sleep disorders. A meta-analysis, J Gen Intern Med, 20(12):1151-1158 (2005).

Büchler, P. et al., prevention of Metastatic Pancreatic Cancer Growth in vivo by Induction of Apoptosis with Genistein, a Naturally Occurring Isoflavanoid, Pancreas, 26(3):264-273 (2003).

Callahan, M.K. et al., Immunomodulatory therapy for melanoma: ipilimumab and beyond, Clin Dermatol, 31(2):191-199 (2013).

Cao, Y. et al., Forty-Year Journey of Angiogenesis Translational Research, Science Translational Medicine, 3(114):1-8 (2011).

Carrillo-Vico, A. et al., A review of the multiple actions of melatonin on the immune system, Endocrine, 27(2):189-200 (2005).

Conley, S.J. et al., Antiangiogenic agents increase breast cancer stem cells via the generation of tumor hypoxia, Proc Natl Acad Sci USA, 109(8):2784-2789 (2012).

Constantinou, M., Low Dose Naltrexone for Metastatic Melanoma, Castrate Resistant Prostate Cancer and Renal Cancer, Brown University, ClinicalTrials.gov, Identifier: NCT01650350, 3 pages (Jul. 24, 2012) [URL: http://clinicaltrials.gov/ct2/show/NCT01650350].

Cremer, D.R. et al., Safety evaluation of alpha-lipoic acid (ALA), Regul Toxicol Pharmacol., 46(1):29-41 (2006).

Cruz-Munoz, W. et al., Effective treatment of advanced human melanoma metastasis in immunodeficient mice using combination metronomic chemotherapy regimens, Clin Cancer Res, 15(15):4867-4874 (2009).

Cuomo, J. et al., Comparative Absorption of a Standardized Curcuminoid Mixture and its Lecithin Formulation, J. Nat. Prod, 74:664-669 (2011).

Cutando, A. et al., Role of melatonin in cancer treatment, Anticancer Res, 32(7):2747-2753 (2012).

Dauchy, B. and Mau, L., The Anticancer Effects of Melatonin on Leiomyosarcoma, National LeioMyoSarcoma Foundation, Inc. "Slay the Dragon", pp. 1-59 (Apr. 21, 2012).

Del Barco, S. (2011). et al., Metformin: multi-faceted protection against cancer, Oncotarget, 2(12):896-917 (2011).

Deng, X.S. et al., Metformin targets Stat3 to inhibit cell growth and induce apoptosis in triple-negative breast cancers, Cell Cycle, 11(2):367-376 (2012).

Dhillon, N. et al., Phase II Trial of Curcumin in Patients with Advanced Pancreatic Cancer, Clin. Cancer Res., 14(14):4491-4499 (2008).

DiMasi, J.A. et al., The price of innovation: new estimates of drug development costs, J Health Econ, 22(2):151-185 (2003).

Draft Guidance, Guidance for Industry Codevelopment of Two or More Unmarketed Investigational Drugs for Use in Combination. U.S. Dept of Health and Human Services, FDA, CDER, 9567dft, Dec. 2010.

Duque, J.E. et al., Metformin as a Novel Component of Metronomic Chemotherapeutic Use: A Hypothesis, J Exper & Clin Med, 4(3):140-144 (2012).

Ebos, J.M. and Kerbel, R.S., Antiangiogenic therapy: impact on invasion, disease progression, and metastasis, Nat Rev Clin Oncol, 8(4):210-221 (2011).

Ehrmann, D.A. et al., Effects of Metformin on Insulin Secretion, Insulin Action, and Ovaria Steroidogenesis in Women with Polycystic Ovary Syndrome, Journal of Clinical Endocrinology and Metabolism, 82(2):524-530 (1997).

Emmenegger, U. et al., A comparative analysis of low-dose metronomic cyclophosphamide reveals absent or low-grade toxicity on tissues highly sensitive to the toxic effects of maximum tolerated dose regimens, Cancer Res, 64(11):3994-4000 (2004).

Emmenegger, U. et al., Pharmacodynamic and pharmacokinetic study of chronic low-dose metronomic cyclophosphamide therapy in mice, Mol Cancer Ther, 6(8):2280-2289 (2007).

Faubert, B. et al., AMPK is a negative regulator of the Warburg Effect and suppresses tumor growth in vivo, Cell Metab., 17(1):113-124 (2013).

Ferrara, N. and Kerbel, R.S., Angiogenesis as a therapeutic target, Nature, 438(7070):967-974 (2005).

Feuerecker, B. et al., Lipoic acid inhibits cell proliferation of tumor cells in vitro and in vivo, Cancer Biology & Therapy, 13(14):1425-1435 (2012).

Finney, L. et al., X-ray fluorescence microscopy reveals large-scale relocalization and extracellular translocation of cellular copper during angiogenesis, PNAS, 104(7): 2247-2252 (2007).

Folkman, J. and Kalluri, R., Cancer without disease, Nature, 427(6977):787 (2004).

Folkman, J., Angigoenesis in cancer therapy—Endostatin and its mechanisms of action, Exp Cell Res, 312(5):594-607 (2006).

Folkman, J., Angiogenesis, Annu Rev Med, 57:1-18 (2006).

Folkman, J., Angiogenesis: an organizing principle for drug discovery, Nature Reviews, 6:273-286 (2007).

Folkman, J., Fundamental concepts of the angiogenic process, Cur Mol Med, 3(7):643-651 (2003).

Folkman, J., Tumor Angiogenesis: therapeutic implications, NEJM, 285(21):1182-1186 (1971).

Foretz, M. et al., Metformin inhibits hepatic gluconeogenesis in mice independently of the LKB1/AMPK pathway via a decrease in hepatic energy state, J Clin Invest, 120(7):2355-2369 (2010).

Ghiringhelli F, M. et al., Metronomic cyclophosphamide regimen selectively depletes CD4+CD25+ regulatory T cells and restores T and NK effector functions in end stage cancer patients, Cancer Immunol Immunother, 56(5):641-648 (2007).

Glienke, W. et al., Curcumin inhibits constitutive STAT3 phosphorylation in human pancreatic cancer cell lines and downregulation of survivin/BIRC5 gene expression, Cancer Invest, 28(2):166-171 (2010).

Goodwin, P.J. et al., Evaluation of metformin in early breast cancer: a modification of the traditional paradigm for clinical testing of anti-cancer agents, Breast Cancer Res. Treat., 126:215-220 (2011).

Guais, A. et al., Adding a combination of hydroxycitrate and lipoic acid (METABLOC™) to chemotherapy improves effectiveness

(56) References Cited

OTHER PUBLICATIONS against tumor development: experimental results and case report, Invest New Drugs, 30(1):200-211 (2012).
Guo, T.L. et al., Genistein Modulates Immune Responses and Increases Host Resistance to B16F10 Tumor in Adult Female B6C3F1 Mice, J. Nutr., 131(12):3251-3258 (2001).
Gupta, S.C. et al., Curcumin, a Component of Turmeric: From Farm to Pharmacy, Biofactors, 39(1):2-13 (2013).
Gupta, S.C. et al., Therapeutic roles of curcumin: lessons learned from clinical trials, AAPS Journal, 15(1):195-218 (2013).
Gwinn, D. A. et al., AMPK Phosphorylation of Raptor Mediates a Metabolic Checkpoint, Molecular Cell, 30: 214-226 (2008).
Hanahan, D. and Folkman, J., Patterns and emerging mechanisms of the Angiogenic switch during tumorigenesis, Cell, 86(3):353-364 (1996).
Hanahan, D. and Weinberg, R.A., Hallmarks of cancer: the next generation, Cell, 144(5):646-674 (2011).
Hanahan, D. and Weinberg, R.A., The hallmarks of cancer, Cell, 100(1):57-70 (2000).
Hasima, N. and Aggarwal, B.B., Cancer-linked targets modulated by curcumin, Int J Biochem Mol Biol, 3(4):328-351 (2012).
Henry Ford Health System, Melatonin shows potential to shlow tumor growth in certain breast cancers, Science Daily, 2 pages (Jan. 28, 2014).
Hermans, I.F. et al., Synergistic effect of metronomic dosing of cyclophosphamide combined with specific antitumor immunotherapy in a murine melanoma model, Cancer Res, 63(23):8408-8413 (2003).
Huang, X. et al., Genistein Inhibits p38 Map Kinase Activation, Matrix Metalloproteinase Type 2, and Cell Invasion in Human Prostate Epithelial Cells, Cancer Res., 65(8): 3470-3478 (2005).
Humphrey, R.W. et al., Opportunities and challenges in the development of experimental drug combinations for cancer, J Natl Cancer Inst, 103(16):1222-1226 (2011).
International Search Report for PCT/US2014/033820, 6 pages (dated Dec. 1, 2014).
Irving, G.R.B. et al., Prolonged biologically active colonic tissue levels of curcumin achieved after oral administration—a clinical pilot study including assessment of patient acceptability, Cancer Prev. Res. (Phila)., 6(20): 119-128 (2013).
Jenkins, D., ALA and Prostate Cancer., University of Toronto, ClinicalTrials.gov, Identifier: NCT00309439, 2 pages (Mar. 29, 20016). [URL: http://clinicaltrials.gov/ct2/show/NCT00309439].
Jiralerspong, S. et al., Metformin and pathologic complete responses to neoadjuvant chemotherapy in diabetic patients with breast cancer, J Clin Oncol, 27(20):3297-3302 (2009).
Jones, S.E. et al., Phase III trial comparing doxorubicin plus cyclophosphamide with docetaxel plus cyclophosphamide as adjuvant therapy for operable breast cancer, J Clin Oncol, 24(34):5381-7 (2006) and Erratum, J Clin Oncol, 25(13):1819 (2007).
Kalender, A. et al., Metformin, independent of AMPK, inhibits mTORC1 in a rag GTPase-dependent manner, Cell Metab, 11(5):390-401 (2010).
Kanai M, Y. et al., A phase I/II study of gemcitabine-based chemotherapy plus curcumin for patients with gemcitabine-resistant pancreatic cancer, Cancer Chemother Pharmacol, 68(1):157-164 (2011).
Kanai, M. et al., A phase I study investigating the safety and pharmacokinetics of highly bioavailable curcumin (Theracurmin®) in cancer patients. Cancer Chemother Pharmacol, (2013).
Kanai, M. et al., Dose escalation and pharmacokinetic study of nanoparticle curcumin, a potential anti-cancer agent with improved bioavailability, in healthy human volunteers, Kyoto University Research Information Repository, Cancer chemotherapy and pharmacology, 69(1): 65-70 (2012).
Kane, M.A. et al., Serum melatonin levels in melanoma patients after repeated oral administration, Melanoma Res, 4(1):59-65 (1994).
Kerbel, R.S. and Kamen, B.A., The anti-angiogenic basis of metronomic chemotherapy, Nat Rev Cancer, 4(6):423-36 (2004).
Kerbel, R.S., Tumor angiogenesis, N Engl J Med, 358(19):2039-2049 (2008).

Kim, H. et al., Mechanisms of action of the soy isoflavone genistein: emerging role for its effects via transforming growth factor b signaling pathways, Am. J. Clin. Nutr., 68(Suppl 6): 1418S-1425S (1998).
Kim, K.J. et al., Melatonin suppresses tumor progression by reducing angiogenesis stimulated by HIF-1 in a mouse tumor model, J Pineal Res, 54(3):264-270 (2013).
Kumar, S. et al., Metformin Intake is Associated with Better Survival in Ovarian Cancer, Cancer, 119(3):555-562 (2013).
Lakshman, M. et al., Dietary Genistein Inhibits Metastasis of Human Prostate Cancer in Mice, Cancer Res., 68(6): 2024-2032 (2008).
Larghero, P. et al., Biological assays and genomic analysis reveal lipoic acid modulation of endothelial cell behavior and gene expression, Carcinogenesis, 28(5): 1008-1020 (2007).
Larsson, O. et al., Distinct perturbation of the translatome by the antidiabetic drug metformin, Proc Natl Acad Sci USA, 109(23):8977-8982 (2012).
Lazarevic, B. et al., Efficacy and safety of short-term genistein intervention in patients with localized prostate cancer prior to radical prostatectomy: a randomized, placebo-controlled, double-blind Phase 2 clinical trial, Nutr Cancer, 63(6):889-898 (2011).
Lemoine, P. et al., Prolonged-release melatonin for insomnia—an open-label long-term study of efficacy, safety, and withdrawal, Ther Clin Risk Manag, 7:301-311 (2011).
Lin, C-C. et al., Metformin Enhances Cisplatin Cytotoxicity by Suppressing Signal Transducer and Activator of Transcription-3 Activity Independently of the Liver Kinase B1-AMP-Activated Protein Kinase Pathway, American Journal of Respiratory Cell and Molecular Biology, 49: 241-250 (2013).
Lissoni, P. et al., A new neuroimmunotherapeutic strategy of subcutaneous low-dose interleukin-2 plus the long-acting opioid antagonist naltrexone in metastatic cancer patients progressing on interleukin-2 alone, Neuro Endocrinol Lett, 23(3):255-258 (2002).
Lissoni, P. et al., A randomised study with subcutaneous low-dose interleukin 2 alone vs interleukin 2 plus the pineal neurohormone melatonin in advanced solid neoplasms other than renal cancer and melanoma, Br J Cancer, 69(1):196-199 (1994).
Lissoni, P. et al., A randomized study of chemotherapy with cisplatin plus etoposide versus chemoendocrine therapy with cisplatin, etoposide and the pineal hormone melatonin as a first-line treatment of advanced non-small cell lung cancer patients in a poor clinical state, J Pineal Res, 23(1):15-19 (1997).
Lissoni, P. et al., Five years survival in metastatic non-small cell lung cancer patients treated with chemotherapy alone or chemotherapy and melatonin: a randomized trial, J Pineal Res, 35(1):12-15 (2003).
Lissoni, P. et al., Neuroimmunomodulation in medical oncology: application of psychoneuroimmunology with subcutaneous low-dose IL-2 and the pineal hormone melatonin in patients with untreatable metastatic solid tumors, Anticancer Res, 28(2B):1377-1381 (2008).
Lissoni, P., Decreased toxicity and increased efficacy of cancer chemotherapy using the pineal hormone melatonin in metastatic solid tumour patients with poor clinical status, Eur J Cancer, 35(12):1688-92 (1999).
Liu, S-L. et al., A Novel Inhibitory Effect of Naloxone on Macrophage Activation and Atherosclerosis Formation in Mice, Journal of the American College of Cardiology, 48(9): 1871-1879 (2006).
Loeffler, M. et al., Immunostimulatory Effects of low-Dose Cyclophosphamide are Controlled by Inducible Nitric Oxide Synthase, Cancer Res., 65(12): 5027-5030 (2005).
Loven, D. et al., Low-dose metronomic chemotherapy: from past experience to new paradigms in the treatment of cancer, Drug Discov Today, 18(3-4):193-201 (2013).
Lutsiak, M.E.C. et al., Inhibition of CS4+25+T regulatory cell function implicated in enhances immune response by low-dose cyclophosphamide, Blood, 105(7): 2862-2868 (2005).
Lv, D. et al., Melatonin inhibits the expression of vascular endothelial growth factor in pancreatic cancer cells, Chin. J. Cancer Res., 24(4): 316-322 (2012).

(56) References Cited

OTHER PUBLICATIONS

MacKenzie, G.G. et al., Curcumin induces cell-arrest and apoptosis in association with the inhibition of constitutively active NF-kappaB and STAT3 pathways in Hodgkin's lymphoma cells, Int J Cancer, 123(1):56-65 (2008).
Maitland, M.L. et al., Analysis of the yield of phase II combination therapy trials in medical oncology, Clin Cancer Res, 16(21):5296-5302 (2010).
Man, S. et al., Antitumor effects in mice of low-dose (metronomic) cyclophosphamide administered continuously through the drinking water, Cancer Res, 62(10):2731-2735 (2002).
Marczylo, T.H. et al., Comparison of systemic availability of curcumin with that of curcumin formulated with phosphatidylcholine, Cancer Chemother Pharmacol, 60(2):171-177 (2007).
Marini, H. et al., Breast Safety and Efficacy of Genistein Aglycone for Postmenopausal Bone Loss: A Follow-Up Study, J. Clin. Endocrinol. Metab., 93(12): 4784-4796 (2008).
McClain, M.R. et al., Acute, subchronic and chronic safety studies with genistein in rats, Food Chem Toxicol, 44(1):56-80 (2006).
McClain, M.R. et al., Subchronic and chronic safety studies with genistein in dogs, Food Chem Toxicol, 43(10):1461-1482 (2005).
Mediavilla, M.D. et al., Basic mechanisms involved in the anti-cancer effects of melatonin, Curr Med Chem, 17(36):4462-4481 (2010).
Mercola, J., One of the RARE Drugs that Actually Helps Your Body to Heal Itself, Mercola.com, 3 pages (Sep. 19, 2011).
Messing, E. et al., A phase 2 cancer chemoprevention biomarker trial of isoflavone G-2535 (genistein) in presurgical bladder cancer patients, Cancer Prev Res (Phila), 5(4):621-630 (2012).
Miller, R.A. and Birnbaum, M.J., An energetic tale of AMPK-independent effects of metformin, J Clin Invest, 120(7):2267-2270 (2010).
Moungjaroen, J. et al., Reactive Oxygen Species Mediate Caspase Activation and Apoptosis Induced by Lipoic Acid in Human Lung Epithelial Cancer Cells through Bcl-2 Down-Regulation, Journal of Pharmacology and Experimental Therapeutics, 319(3): 1062-169 (2006).
Nakahara, T. et al., Cyclophosphamide enhances immunity by modulating the balance of dendritic cell subsets in lymphoid organs, Blood, 115(22):4384-4392 (2010).
Ocker, M. and Höpfner, M., Apoptosis-modulating drugs for improved cancer therapy, Eur Surg Res, 48(3):111-120 (2012).
Owen, J.L. et al., Molecular events involved in the increased expression of matrix metalloproteinase-9 by T lymphocytes of mammary tumor-bearing mice, International Journal of Molecular Medicine, 21: 125-134 (2008).
Penel, N. et al., Cyclophosphamide-based metronomic chemotherapy: after 10 years of experience, where do we stand and where are we going?, Crit Rev Oncol Hematol, 82(1):40-50 (2012).
Perkins, S. et al., Chemopreventive Efficacy and Pharmacokinetics of Curcumin in the Min/+ Mouse, a Model of Familial Adenomatous Polyposis, Cancer Epidemiology, Biomarkers & Prevention, 11: 535-540 (2002).
Peters K; Brain Tumor Fund for the Carolinas. Low-Dose Naltrexone for Glioma Patients. In: ClinicalTrials.gov [Internet]. Bethesda (MD): National Library of Medicine (US). 2000-[Feb. 23, 2011]. Available from http://clinicaltrials.gov/ct2/show/NCT01303835: NCT01303835.
Record, I.R. et al., Genistein inhibits growth of B16 melanoma cells in vivo and in vitro and promotes differentiation in vitro, Int J Cancer, 72(5):860-864 (1997).
Riether, C. et al., From "magic bullets" to specific cancer immunotherapy, Swiss Med Wkly, 143:13734 (2013).
Rodriguez, C. et al., Mechanisms involved in the pro-apoptotic effect of melatonin in cancer cells, Int J Mol Sci, 14(4):6597-6613 (2013).
Rozman, K.K. et al., NTP-CERHR expert panel report on the reproductive and developmental toxicity of genistein, Birth Defects Res B Dev Reprod Toxicol, 77(6):485-638. Review (2006).

Saydmohammed, M. et al., Curcumin suppresses constitutive activation of STAT-3 by up-regulating protein inhibitor of activated STAT-3 (PIAS-3) in ovarian and endometrial cancer cells, J Cell Biochem, 110(2):447-56 (2010).
Schnipper, L.E. et al., Value and cancer care: toward an equitable future, Clin Cancer Res, 16(24):6004-6008 (2010).
Schwartz, L. et al., A combination of alpha lipoic acid and calcium hydroxycitrate is efficient against mouse cancer models: preliminary results, Oncol Rep, 23(5):1407-1416 (2010).
Shackelford, D.B. and Shaw, R.J., The LKB1-AMPK pathway: metabolism and growth control in tumour suppression, Nat Rev Cancer, 9(8):563-575 (2009).
Sharma, R.A. et al., Phase I clinical trial of oral curcumin: biomarkers of systemic activity and compliance, Clin Cancer Res, 10(20):6847-6854 (2004).
Shaw, R.J. et al., The kinase LKB1 mediates glucose homeostasis in liver and therapeutic effects of metformin, Science, 310(5754):1642-1646 (2005).
Shaw, R.J., LKB1 and AMP-activated protein kinase control of mTOR signalling and growth, Acta Physiol (Oxf), 196(1):65-80 (2009).
Shay, K.P. et al., Alpha-lipoic acid as a dietary supplement: Molecular mechanisms and therapeutic potential, Biochim Biophys Acta, 1790(10):1149-1160 (2009).
Singleton, P.A. et al., Synergistic effects of methylnaltrexone with 5-fluorouracil and bevacizumab on inhibition of vascular endothelial growth factor-induced angiogenesis, Mol. Cancer. Ther., 7(6): 1669-1679 (2008).
Smith, J.P. et al., Low-dose naltrexone therapy improves active Crohn's disease, Am J Gastroenterol, 102(4):820-828 (2007).
Smith, J.P. et al., Safety and tolerability of low-dose naltrexone therapy in children with moderate to severe Crohn's disease: a pilot study, J Clin Gastroenterol, 47(4):339-345 (2013).
Stoelting, S. et al., Low-dose oral metronomic chemotherapy prevents mobilization of endothelial progenitor cells into the blood of cancer patients, in Vivo, 22(6):831-866 (2008).
Su, C.C. et al., Curcumin inhibits human lung large cell carcinoma cancer tumour growth in a murine xenograft model, Phytother Res, 24(2):189-192 (2010).
Sánchez-Hidalgo, M. et al., Melatonin, A Natural Programmed Cell Death Inducer in Cancer, Current Medicinal Chemistry, 19: 3805-3821 (2012).
Vogelstein, B. et al., Cancer genome landscapes, Science, 339(6127):1546-1558 (2013).
Wang, Y.M. et al., The efficacy and safety of melatonin in concurrent chemotherapy or radiotherapy for solid tumors: a meta-analysis of randomized controlled trials, Cancer Chemother Pharmacol, 69(5):1213-1220 (2012).
Ward, P.S. and Thompson, C.B., Metabolic reprogramming: a cancer hallmark even warburg did not anticipate, Cancer Cell, 21(3):297-308 (2012).
Watkins, L.R. et al., Glia as the "bad guys": Implications for improving clinical pain control and the clinical utility of opioids, Brain Behav. Immun., 21(2): 131-146 (2007).
Watson, J.L. et al., Curcumin-induced apoptosis in ovarian carcinoma cells is p53-independent and involves p38 mitogen-activated protein kinase activation and downregulation of Bcl-2 and survivin expression and Akt signaling, Mol Carcinog, 49(1):13-24 (2010).
Wenger, J.B. et al., Combination therapy targeting cancer metabolism, Med Hypotheses, 76(2):169-72 (2011).
Wong, R.S., Apoptosis in cancer: from pathogenesis to treatment, J Exp Clin Cancer Res, 30:87 (2011).
Woodcock, J. et al., Development of Novel Combinator Therapies, N Engl J Med, 364(11):985-987 (2011).
Written Opinion for PCT/US2014/033820, 9 pages (dated Dec. 1, 2014).
Wu, B. et al., DAPK1 modulates a curcumin-induced G2/M arrest and apoptosis by regulating STAT3, NF-κB, and caspase-3 activation, Biochem Biophys Res Commun, 434(1):75-80 (2013).
Xu, C. et al., Melatonin is involved in the apoptosis and necrosis of pancreatic cancer cell line SW-1990 via modulating of Bcl-2/Bax balance, Biomed Pharmacother, 67(2):133-139 (2013).

(56) References Cited

OTHER PUBLICATIONS

Younger, J. et al., Low-dose naltrexone for the treatment of fibromyalgia: findings of a small, randomized, double-blind, placebo controlled, counterbalanced, crossover trial assessing daily pain levels, Arthritis Rheum, 65(2):529-538 (2013).
Younger, J. et al., The use of low-dose naltrexone (LDN) as a novel anti-inflammatory treatment for chronic pain, Clin. Rheumatol., 33: 451-459 (2014).
Yun, J. et al., Glucose deprivation contributes to the development of KRAS pathway mutations in tumor cells, Science, 325(5947):1555-1559 (2009).
Zhang, C. et al., Curcumin Selectively Induces Apoptosis in Cutaneous T-Cell Lymphoma Cell Lines and Patients' PBMCs: Potential Role for STAT-3 and NF-κB Signaling, Journal of Investigative Dermatology, 130 2110-2119 (2010).
Barni, S. et al., A randomized study of low-dose subcutaneous interleukin-2 plus melatonin versus supportive care alone in metastatic colorectal cancer patients progressing under 5-fluorouracil and folates, Oncology, 52(3):243-245 (1995).
Donahue, R.N. et al., Low-dose naltrexone suppresses ovarian cancer and exhibits enhanced inhibition in combination with cisplatin, 236: 883-895 (2011).
Foster, T.S., Efficacy and safety of alpha-lipoic acid supplementation in the treatment of symptomatic diabetic neuropathy, Diabetes Educ, 33(1):111-117 (2007).
Gomez-Pinillos, A. and Ferrari, A.C., mTOR signaling pathway and mTOR inhibitors in cancer therapy, Hematol Oncol Clin North Am, 26(3):483-505 (2012).
Hung, C.S. et al., Knockdown survivin expression reduces the efficacy of curcumin treatment in hepatocellular carcinoma cells, Ann Surg Oncol, 19(11):3547-3555 (2012).
Korotchkina, L.G. et al., R-lipoic acid inhibits mammalian pyruvate dehydrogenase kinase, Free Radic Res, 38(10):1083-1092 (2004).
Lissoni, P. and Rovelli, F., Principles of psychoneuroendocrinoimmunotherapy of cancer, Immunotherapy, 4(1):77-86 (2012).
Lissoni, P. et al., A randomized study of neuroimmunotherapy with low-dose subcutaneous interleukin-2 plus melatonin compared to supportive care alone in patients with untreatable metastatic solid tumour, Support Care Cancer, 3(3):194-197 (1995).
Lissoni, P. et al., A randomized study of tamoxifen alone versus tamoxifen plus melatonin in estrogen receptor-negative heavily pretreated metastatic breast-cancer patients, Oncol Rep, 2(5):871-873 (1995).
Lissoni, P. et al., Modulation of cancer endocrine therapy by melatonin: a phase II study of tamoxifen plus melatonin in metastic breast cancer patients progressing under tamoxifen alone, British Journal of Cancer, 71: 854-856 (1995).
Lissoni, P. et al., Neuroimmunotherapy of untreatable metastatic solid tumors with subcutaneous low-dose interleukin-2, melatonin and naltrexone: modulation of interleukin-2-induced antitumor immunity by blocking the opioid system, Neuroendocrinology Letters, 23(4):341-344 (2002).
Lissoni, P., Biochemotherapy with standard chemotherapies plus the pineal hormone melatonin in the treatment of advanced solid neoplasms, Pathol Biol (Paris), 55(3-4):201-204 (2007).
Marín, Y.E. et al., Curcumin downregulates the constitutive activity of NF-kappaB and induces apoptosis in novel mouse melanoma cells, Melanoma Res, 17(5):274-283 (2007).
Pasquier, E. et al., Metronomic chemotherapy: new rationale for new directions, Nat Rev Clin Oncol, 7(8):455-65 (2010).
Sánchez-Barceló, E.J. et al., Clinical uses of melatonin: evaluation of human trials, Curr Med Chem, 17(19):2070-95. Review (2010).
Yoon, G. et al., Safety, tolerability, and feasibility of high-dose naltrexone in alcohol dependence: an open-label study, Hum Psychopharmacol, 26(2):125-132 (2011).
Xin-Yu, W. and Qian-Jin, L., Recent Progress in Research on Toxicological Mechanism of Cyclophosphamide and the Improving Measures, Progress in Pharmaceutical Sciences, 30(10): 452-456 (2006).
Author Not Known, Immediate improvement in patient with multiple metastases in breast cancer, (Jun. 10, 2010), <<https://www.humlegaarden.com>>. Retrieved on Jun. 25, 2018.
Dowling, R. Jo. et al, Understanding the benefit of metformin use in cancer treatment, BMC Medicine, 9(33): 1-6 (2011).
Lissoni, P. et al, Clinical results with the pineal hormone melatonin in advanced cancer resistant to standard antitumor therapies, Oncology, 48(6): 448-50 (1991). [Abstract only].
Na, M. H. et al, Effects of α-lipoic acid on cell proliferation and apoptosis in MDA-MB-231 human breast cells, Nutrition Research and Practice, 3(4): 265-271 (2009).
Royt, M. et al, Curcumin sensitizes chemotherapeutic drugs via modulation of PKC, telomerase, NF-kappaB and HDAC in breast cancer, Ther. Deliv., 2(10): 1275-93 (2011). [Abstract only].
Wenzel, U. et al, α-lipoic acid induces apoptosis in human colon cancer cells by increasing mitochondrial respiration with a concomitant $O_2$-generation, Apoptosis, 10: 359-368 (2005).
Yu, Z. et al, Inhibition of proliferation and induction of apoptosis by genistein in colon cancer HT-29 cells, Cancer Letters, 215: 159-166 (2004).
Duque, J.E. et al., Antitumor mechanisms of metformin: Signaling, metabolism, immunity and beyond, Universitas Scientiarum, 15(2): 1-6 (2010).

* cited by examiner

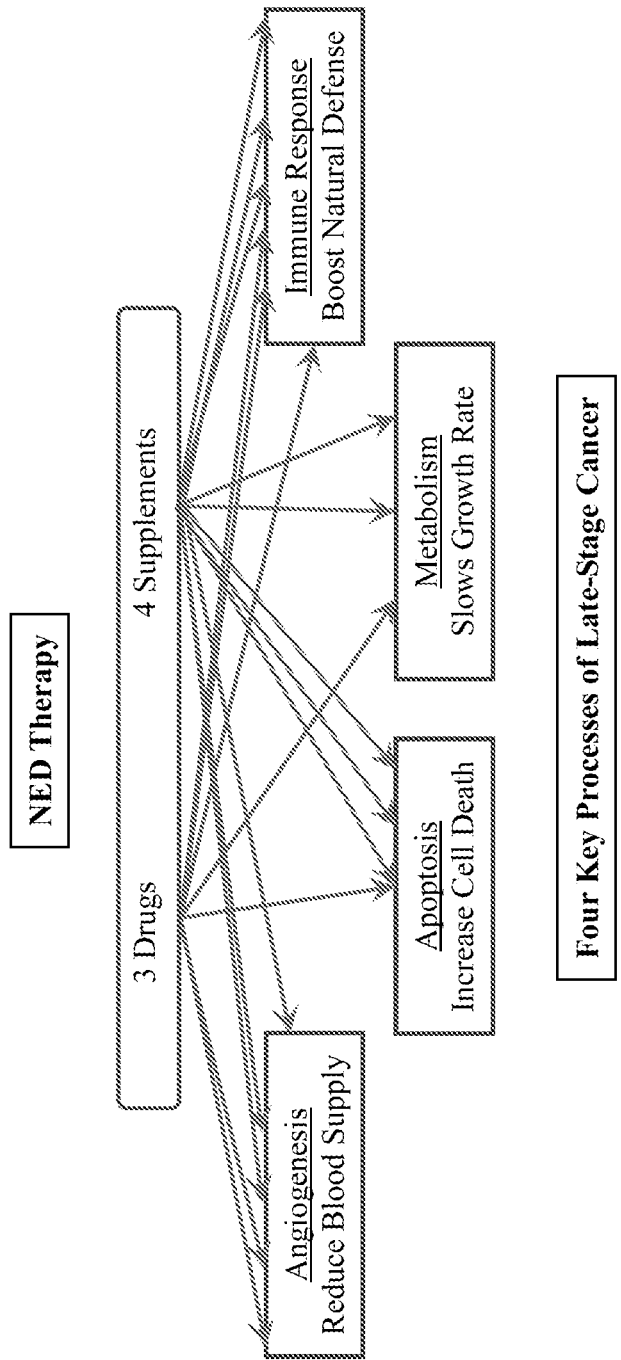

CANCER THERAPY

CROSS REFERENCE TO RELATED APPLICATIONS

This application is a U.S. national phase application under 35 U.S.C. § 371 of international PCT application no. PCT/US2014/33820, filed Apr. 11, 2014, which claims the benefit of priority to U.S. Provisional Patent Application No. 61/811,209, entitled "TREATMENT FOR CANCERS OF EPITHELIAL ORIGIN" filed Apr. 12, 2013; the entire contents of each of these prior applications is incorporated herein by reference.

BACKGROUND

Cancer is a leading cause of death worldwide, accounting for 7.6 million deaths (around 13% of all deaths) in 2008. Lung, stomach, liver, colon, and breast cancer cause the most cancer deaths each year, according to the World Health Organization. Cancer is the second leading cause of death in the United States, exceeded only by heart disease. In 2008, more than 565,000 people died of cancer, and more than 1.48 million people had a diagnosis of cancer, according to the United States Cancer Statistics: 1999-2008 Incidence and Mortality Web-based Report. The cost of cancer extends beyond the number of lives lost and new diagnoses each year. The financial costs of cancer also are overwhelming. According to the National Institutes of Health, cancer cost the United States an estimated $263.8 billion in medical costs and lost productivity in 2010. (See, www.cdc.gov/chronicdisease/resources/publications/AAG/dcpc.htm.)

SUMMARY

The present invention relates in general to methods and compositions for the treatment of cancer, in some embodiments for the treatment of cancers of epithelial cell origin. Improved treatment methods and regimens described herein are the product of a novel and comprehensive approach to the development of individualized treatments for cancer. The approach to treatment recognizes that cancer growth and metastasis depends on unchecked cellular processes, in particular angiogenesis, and simultaneously the activation of multiple metabolic and signaling pathways in the patient. Pathways that in a normal individual would suppress, or at least not support, cancer growth are inactive, blocked or attenuated in a cancer patient; likewise, pathways that are cancer-supportive, which are held in check or counterbalanced in a normal individual, are amplified in a cancer patient. In some embodiments, an object of the therapeutic approach of the present invention is to inhibit or attenuate angiogenesis as well as to rebalance as many of the metabolic, intercellular signaling, and intracellular signaling pathways that are detected or suspected to be contributing to the survival or growth of the cancer.

In some particular embodiments, objects of provided treatment protocols described herein are to achieve one or more of the following:

blocking, interrupting, or attenuating tumor angiogenesis (i.e., the formation and development of the vasculature that tumors need in order to thrive and progress) or pathways that support angiogenesis, including disruption of signaling inducing vasculogenic mimicry (e.g. tumor stem cell activity);

reducing, blocking, or reversing the mechanisms of chemo-resistance to chemotherapeutic drugs, in order to enhance effectiveness of chemotherapy, preferably while increasing anti-tumor, pro-apoptotic activity;

supporting a metabolic shift from aerobic glycolysis (the "Warburg Effect") to glucose oxidation, which promotes or renews a capacity for undergoing apoptosis;

blocking, interrupting, or attenuating intracellular tumor cell signal transduction pathways that promote tumor cell growth;

inhibiting intercellular signaling pathways that facilitate tumor invasion into local tissues and tumor metastasis (i.e., the spread of tumor cells to other tissues or organs);

Inducing opioid immune modulation that has an inhibitory effect on cell proliferation. (Donahue R N et al., Low-dose naltrexone targets opioid growth factor receptor pathway to inhibit cell proliferation: mechanistic evidence from tissue culture model, *Exp. Biol. Med.* (Maywood), 2011 Sep. 1; 236(9); 1036-50)

reducing or avoiding toxic side effects of chemotherapy and any other active ingredients added to a treatment regimen; and augmenting or enhancing the patient's host defenses (particularly the host immune system), their general health and well-being.

In some embodiments, the present invention provides a unique approach for the treatment of cancer, combining use of one or more agents conventionally included in cancer treatments with administration of one or more naturally-occurring compounds and/or nutrients, e.g., "nutraceuticals".

In some embodiments, treatment protocols described herein are designed to inhibit, arrest, and/or otherwise disrupt, or, where appropriate, enhance endogenous signaling pathways and/or upregulate anti-angiogenic regulators (such as angiostatin, endostatin, or thrombospodin-1) that, when dysregulated, lead to the formation or support the development of cancerous growth or tumors.

In a preferred embodiment, the present invention is directed to compositions and methods for the treatment of cancers or tumors that are epithelial cell related.

In another embodiment, the present invention is designed to prevent the recurrence of cancer, by continuing the disclosed treatment regimen once it has been determined that the cancer or tumor is in remission or, in other words, there is no evidence of disease.

One unique feature of the method and compositions described herein is that the combination of compounds and dosages of each can be tailored for each individual or patient in order to maximize the benefit realized for that particular patient. In this respect, the treatment regimen will be based on a pretreatment analysis of specific parameters, for example, on an analysis of blood or biopsied tissue obtained from the patient to be treated, prior to initiating the regimen.

The present invention provides a unique integrative approach to cancer therapy, in which conventional oncology can be merged with complementary modalities. The complementary aspect emphasizes the use of natural compounds and non-chemotherapeutic drugs to facilitate a synergistic approach in which each element of treatment, both conventional and non-conventional, is designed to inhibit angiogenesis and the oncogenic signaling transduction pathways within cancer cells and the intercellular signaling between tumor cells and their local cellular and biochemical microenvironment, with a strong emphasis on disruption of the intercellular signaling that fuels the ongoing processes of tumor angiogenesis.

The present invention encompasses a variety of novel insights, including defining the sources of various problems associated with certain conventional chemotherapeutic regimens, as described herein.

For example, in some embodiments, the present invention provides therapeutic modalities that target multiple pathways. In some embodiments, the present invention provides therapeutic regimens utilizing a combination of components that together target a particular pathway multiple times and/or in multiple ways (see, for example, as illustrated in FIG. 1).

In some embodiments, the present invention encompasses the recognition that a variety of agents that are not traditional chemotherapeutic agents in that, for example, they do not specifically modulate a particular single druggable target (e.g., inhibit an oncogene product or enhance a tumor suppressor gene product), are useful in treating cancer, particularly when utilized in combination as described herein.

In some embodiments, the present invention encompasses the recognition that certain agents developed and/or utilized for treatment of non-life-threatening and/or chronic diseases, disorders and conditions are unexpectedly particularly useful in the treatment of cancer when they target pathways as described herein and/or are utilized in combination as described herein.

In some embodiments, the present invention encompasses the recognition that chronic administration of agents, particularly of agents with high therapeutic indices, and/or particularly at doses well below their maximum tolerated doses is unexpectedly particularly useful in the treatment of cancer, particularly when utilized in combination as described herein.

Various other insights and advantages provided by the present disclosure are discussed in further detail herein.

In certain particularly preferred embodiments of the present invention, methods and/or compositions are individually tailored to the patient in need of treatment and are based on a number of parameters measured in, for example, blood samples or tissue biopsies taken from the patient to be treated, to determine the optimal combination and dosages of each compound of the composition selected for the treatment of that individual.

It is also contemplated in certain embodiments that, once a cancer is in remission (e.g., by following the methods and teachings disclosed herein), the patient can continue on a treatment regimen according to the invention, in order to maintain or lengthen the period of remission, or until one or more abnormally upregulated cancer-supportive metabolic and/or signaling pathways or one or more abnormally downregulated cancer-suppressive metabolic and/or signaling pathways return to normal. In this way, following the methods of the invention helps to prevent recurrence of the disease.

In some embodiments, treatment regimens provided by the present invention comprise administration of a combination of active ingredients, which may be administered in addition to conventional anticancer therapeutics (chemotherapeutic agents), so that an inventive combination will often include naturally occurring compounds, nutrients, extracts or other nutraceutical compounds such as, for instance, Curcumin, etc., non-chemotherapeutic agents, such as, for instance, Metformin, Naltrexone, Melatonin, etc.; and/or chemotherapeutic agents such as cyclophosphamide. In some embodiments, a composition to be administered to a cancer patient may comprise a combination of from 3 to 8 or more of these nutraceutical compounds (as currently available or as approved drugs), non-chemotherapeutic drugs, and chemotherapeutic drugs (see, for example, FIG. 1). A particular combination of compounds and dosage of each may be determined by one skilled in the art, for example, the patient's oncologist or primary care physician.

Therefore, the present invention is directed in general to a unique integrative approach to cancer therapy, in which conventional oncology may be merged with complementary modalities. The complementary aspect emphasizes the use of low toxicity combinations to augment and/or improve use of conventional agents to promote synergistic effects or compound effects. In particular, components of inventive combination therapy treatments are designed to collectively abrogate angiogenesis and the oncogenic signaling transduction pathways within cancer cells and the intercellular signaling between tumor cells and their local cellular and biochemical micro-environment, to the end that all or as many biological systems as possible that contribute to the survival of the cancer will be addressed, to the detriment of the cancer and to the improvement of health of the patient. Active ingredients included in the novel approach to cancer treatment described herein have been demonstrated to improve the conventional treatment of cancers, e.g., cancers of epithelial origin (such as breast cancer, esophageal cancer, uterine cancer, liver cancer, etc.), and all forms of cancer or other diseases where regulation of angiogenesis and multiple signaling pathways is called for.

In various aspects, therefore, the present invention provides compositions for administration to a patient diagnosed with cancer, optionally as an adjunct to a chemotherapy, a composition comprising at least three ingredients, each of which is capable of regulating a specific metabolic pathway or intracellular signaling pathway or intercellular signaling pathway implicated in the advent of the cancer, wherein at least three such pathways are addressed. The compositions of the invention may be in the form of an admixture of three or more ingredients, or they may simply be separate ingredients packaged to be used together, so that specific endogenous pathways or processes in the cancer patient are treated simultaneously.

In one embodiment, a composition according to the invention comprises at least three different compounds, wherein at least one compound is selected from Table 1 and from at least two of the following three tables, Tables 2-4, below:

TABLE 1

| Metronomic chemotherapy |
| --- |
| Cyclophosphamide |

TABLE 2

| Naltrexone |
| --- |
| Curcumin |
| Opiod Growth Factor (Met5-enkephalin) |

TABLE 3

| Metformin |
| --- |
| Genistein |
| Curcumin |
| N-Acetyl Cysteine |
| Alpha Lipoic Acid |
| Squalamine |

TABLE 4

Melatonin
Metformin
Naltrexone
Genistein
Squalamine

In an embodiment, a composition of the present invention comprises a combination of Naltrexone, Metformin, and Cyclophosphamide. In further embodiments, one or more other compounds are added to this combination.

In a further embodiment, a composition of the present invention is comprised of at least four different compounds, wherein one compound is selected from each of the four Tables 1-4, above.

In a further embodiment, a composition according to the invention comprises Cyclophosphamide, Metformin, Melatonin, and Curcumin. In a further embodiment, a composition according to the invention comprises the foregoing four compounds and, in addition, Naltrexone, Alpha Lipoic Acid, and Genistein. In a further embodiment, a composition according to the invention comprises Cyclophosphamide, Metformin, Melatonin, Curcumin, Naltrexone, Alpha Lipoic Acid, and Squalamine.

In another embodiment, a composition according to the invention comprises at least five different compounds selected from Tables 1-4, with at least one compound being selected from each of Tables 1, 2, 3, and 4, above.

In a further embodiment, a composition according to the invention comprises Curcumin, Genistein, Cyclophosphamide, Melatonin, and Metformin. In another embodiment, a composition according to the invention comprises at least six different compounds selected from Tables 1-4, with at least one compound being selected from each of Tables 1, 2, 3, and 4, above. A particular embodiment is a composition comprising Curcumin, Cyclophosphamide, Metformin, Melatonin, Alpha Lipoic Acid, and Naltrexone.

In a further embodiment, a composition according to the invention comprises seven compounds as set forth in Table 5, or equivalents thereof:

TABLE 5

Curcumin
Melatonin
Naltrexone
Metformin
Cyclophosphamide
Alpha Lipoic Acid
Genistein (pure)

The foregoing composition is advantageously used as a supplement to standard chemotherapeutic agents.

In a preferred embodiment, the invention provides a supplement for treatment of cancer, comprising the compounds listed in Table 6 below, in sufficient dosages to provide the respective daily amounts:

TABLE 6

| Compound | Amount/Day |
| --- | --- |
| Curcumin | 2400 mg (6 × 400 mg) |
| Melatonin | 10 mg |
| Naltrexone | 4.5 mg |
| Metformin | 500 mg |

TABLE 6-continued

| Compound | Amount/Day |
| --- | --- |
| Cyclophosphamide | 25 mg/day or 50 mg/day |
| Alpha Lipoic Acid | 1200 mg (4 × 300 mg) |
| Genistein (pure) | 8400 mg (6 × 1400 mg) |

For each of the compounds listed in Tables 1-6, substitutions may be made of equivalent compounds that contain the same active ingredient as the original compound or which have a similar effect on the same cellular process (such as angiogenesis), metabolic pathway, intracellular signaling pathway, or intercellular signaling pathway as the original compound. Suitable equivalents for the preferred compounds listed in Tables 1-6 are discussed infra.

The present invention also contemplates the use of any of the previously described compositions in the treatment of cancer, more particularly in the treatment of a cancer of epithelial origin.

In further embodiments, the present invention involves the use of a composition comprising at least three compounds, wherein at least one compound is selected from Table 1 and from at least two of the three Tables 2, 3, and 4, above, for making a medicament for treating an individual suffering from cancer, more particularly for the treatment of a cancer of epithelial origin. In further embodiments, the present invention involves the use of a composition comprising at least four compounds, wherein one compound is selected from each of Tables 1, 2, 3, and 4, above, for making a medicament for treating an individual suffering from cancer, more particularly for the treatment of a cancer of epithelial origin. In further embodiments, the present invention involves the use of a composition comprising at least five compounds selected from Tables 1-4, wherein at least one compound is selected from each of Tables 1, 2, 3, and 4, above, for making a medicament for treating an individual suffering from cancer, more particularly for the treatment of a cancer of epithelial origin. In further embodiments, the present invention involves the use of a composition comprising at least six compounds selected from Tables 1-4, wherein at least one compound is selected from each of Tables 1, 2, 3, and 4 above, for making a medicament for treating an individual suffering from cancer, more particularly for the treatment of a cancer of epithelial origin. In further embodiments, the present invention involves the use of a composition comprising at least six compounds selected from Tables 1-4, wherein at least one compound is selected from each of Tables 1, 2, 3, and 4, above, for making a medicament for treating an individual suffering from cancer, more particularly for the treatment of a cancer of epithelial origin. In further embodiments, the present invention involves the use of a composition comprising at least seven compounds selected from Tables 1-4, wherein at least one compound is selected from each of Tables 1, 2, 3, and 4, above, for making a medicament for treating an individual suffering from cancer, more particularly for the treatment of a cancer of epithelial origin. In a further embodiment, a composition is provided for treating an individual suffering from cancer, more particularly for the treatment of a cancer of epithelial origin, comprising Cyclophosphamide, Metformin, Melatonin, and Curcumin. In a further embodiment, a composition is provided for treating an individual suffering from cancer, more particularly for the treatment of a cancer of epithelial origin, comprising the foregoing four compounds and, in addition, Naltrexone, Alpha Lipoic Acid, and Genistein. In further embodiments, the present invention involves the use of a composition comprising the compounds listed in Table 5, above, for making a medicament for treating an individual suffering from cancer, more particularly for the treatment of a cancer of epithelial origin.

In yet another embodiment, the present invention provides a method for treating an individual suffering from cancer, more particularly for the treatment of a cancer of epithelial origin comprising administering any of the compositions as set forth above. Also disclosed is a method for treating an individual suffering from cancer, more particularly for treating a cancer of epithelial origin, comprising administering any of the compositions set forth above as an adjunct to chemotherapy.

The present invention also provides a method for treating an individual suffering from cancer, more particularly for the treatment of epithelial cell related cancers comprising the steps:

(a) detecting abnormally elevated levels in epithelial tissue or blood of said individual of one or more pro-angiogenic regulators selected from the group consisting of VEGF, MMP-9, MMP-2, TNF-α, TGF-β, EGFR, IL-6, and Leptin, and/or detecting abnormally low levels of angiostatin, endostatin, Thrombospodin-1 or other anti-angiogenic regulator in organ tissue or blood of said individual;

(b) detecting abnormal or undesirable activation of at least two metabolic, intercellular signaling, or intracellular signaling pathways identified in groups I, II, III, IV, and V, below, and wherein abnormal or undesirable activation is detected for pathways in at least two separate groups:

| Group I: Molecular, Genetic, and Intracellular Signaling Pathways |
| --- |
| PI3K/AKT/mTOR |
| RAS/RAF/MEK/ERK (also known as MAP-Kinase (MAPK) Pathway, or ERK 1/2 Pathway) |
| Epidermal Growth Factor Receptor (EGFR) |
| HEDGEHOG |
| Cross-talk between HEDGEHOG and mTOR pathways |
| Insulin Growth Factor-1 (IGF-1) |
| Cross-talk between IGN-1 and Focal Adhesion Kinase (FAK) pathways |
| Vascular Endothelial Growth Factor (VEGF) |
| Cross-talk between VEGF and EGFR pathways |
| BCL-2 (BCL-$X_L$ and MCL-1) |
| NF-kappaB (NFκB) |
| Hypoxia-Inducible Factor 1-alpha (HIF-1α) |
| Vasculogenic mimicry (e.g. tumor stem cell activity) |

| Group II: Tumor Suppression Immune Function |
| --- |
| p53, p21 gene disruptions or mutations |
| Mitochondrial respiration |

| Group III: Metabolic Regulation |
| --- |
| Aerobic glycolysis, Oxidative stress, Warburg effect, COX-2 activation |

| Group IV: Cell Cycle Arrest |
| --- |
| Apoptosis dysregulated; Abnormal cell proliferation |

(c) administering a composition comprising Cyclophosphamide and at least one compound selected from the group of compounds corresponding to the pathway activation detected in (a) and (b) according to the following Table 7 (e.g., Table 7A or Table 7B), said compound being administered in an amount effective to alter said abnormal or undesirable pathway activation toward normal, that is, toward a level of activity in an individual not exhibiting cancer:

TABLE 7A

| Abnormal or Undesired Activity Detected in step (a) or (b) | Selection for Compound to be Administered |
| --- | --- |
| Angiogenic Regulators: | |
| VEGF overexpressed | Melatonin, Curcumin, |
| MMP-9 overexpressed | Curcumin, Metformin, |
| MMP-2 overexpressed | Metformin, Curcumin, |
| TNF-α overexpressed | Alpha Lipoic Acid, Curcumin, |
| EGFR overexpressed | Curcumin, |
| IL-6 overexpressed | Curcumin |
| Leptin overexpressed | Curcumin |
| Group I - Molecular, Genetic, and Intracellular signaling Pathways: | |
| PI3K/AKT/mTOR dysregulated | Curcumin, Melatonin, |
| EGFR-mediated pathways activated | Curcumin, |
| HEDGEHOG activated | Curcumin, |
| cross-talk between HEDGEHOG and mTOR pathways activated | Curcumin, |
| Insulin Growth Factor-1 (IGF-1) pathway activated | Curcumin |
| VEGF-mediated signaling pathways activated | Curcumin, |
| cross-talk between VEGF and EGFR pathways activated | Curcumin, |
| BCL-2 (BCL-$X_L$ and MCL-1) genes overexpressed | Curcumin, |
| NF-kappaB (NFκB) activated | Alpha Lipoic Acid, Naltrexone, |
| Vasculogenic mimicry (e.g. tumor stem cell activity) | Curcumin |
| Group II - Tumor Suppression: | |
| p53 and p21 genes deactivated or mutated | Curcumin, Genistein |
| mitochondrial respiration abnormalities | |
| Group III - Metabolic Regulation: | Metformin, Melatonin, |
| oxidative stress, anaerobic glycolysis, Warburg effect, COX-2 activation | Metformin, Melatonin, Naltrexone, |
| Group IV - Cell Cycle Arrest: | |
| apoptosis dysregulated | Melatonin, Naltrexone |

TABLE 7B

| Abnormal or Undesired Activity Detected in step (a) or (b) | Selection for Compound to be Administered |
| --- | --- |
| Angiogenic Regulators: | |
| VEGF overexpressed | Melatonin, Curcumin, Genistein, Alpha Lipoic Acid, Metformin |
| MMP-9 overexpressed | Curcumin, Metformin, Genistein, Melatonin, |
| MMP-2 overexpressed | Metformin, Curcumin, Genistein, |
| TNF-α overexpressed | Alpha Lipoic Acid, Curcumin, Genistein, Melatonin |
| EGFR overexpressed | Curcumin, Cyclophosphamide, |
| IL-6 overexpressed | Curcumin, Metformin, Genistein, |
| Leptin overexpressed | Curcumin, Genistein, Metformin |
| Group I - Molecular, Genetic, and Intracellular signaling Pathways: | |
| PI3K/AKT/mTOR dysregulated | Curcumin, Melatonin, Alpha Lipoic Acid, Cyclophosphamide, Metformin, |
| EGFR-mediated pathways activated | Curcumin, Alpha Lipoic Acid, |

TABLE 7B-continued

| Abnormal or Undesired Activity Detected in step (a) or (b) | Selection for Compound to be Administered |
|---|---|
| HEDGEHOG activated | Curcumin, Genistein, Alpha Lipoic Acid, |
| cross-talk between HEDGEHOG and mTOR pathways activated | Curcumin, |
| Insulin Growth Factor-1 (IGF-1) pathway activated | Curcumin, Genistein, Metformin, |
| VEGF-mediated signaling pathways activated | Curcumin, Genistein, Melatonin, |
| cross-talk between VEGF and EGFR pathways activated | Curcumin, Melatonin |
| BCL-2 (BCL-$X_L$ and MCL-1) genes overexpressed | Curcumin, Genistein, |
| NF-kappaB (NFκB) activated | Alpha Lipoic Acid, Naltrexone, Genistein, Curcumin, Cyclophosphamide, Metformin, |
| HIF1-α activated | Alpha Lipoic Acid, Curcumin, Genistein, Melatonin, Metformin |
| vasculogenic mimicry (e.g. tumor stem cell activity) | Curcumin, Genistein |
| Group II - Tumor Suppression: | |
| p53 and p21 genes deactivated or mutated | Curcumin, Genistein, Metformin, Alpha Lipoic Acid, |
| mitochondrial respiration abnormalities | Curcumin, Metformin, Alpha Lipoic Acid, |
| Group III - Metabolic Regulation: | Metformin, Melatonin, |
| oxidative stress, anaerobic glycolysis, Warburg effect, COX-2 activation | Metformin, Melatonin, Naltrexone, Alpha Lipoic Acid, |
| Group IV - Cell Cycle Arrest: | |
| apoptosis dysregulated | Melatonin, Naltrexone, Genistein, Cyclophosphamide, Metformin |

Tables 5 and 6, above, show a list of components that can be advantageously administered as part of the treatment regimen described herein for treating a patient diagnosed with cancer, more particularly for the treatment of epithelial cell-related cancers. The list of Table 6 includes typical daily doses for each compound. It will be understood by practitioners in the field that the dosages will be tailored to the individual patient based on, for example, the results of a blood analysis of the patient, monitoring patient progress, etc., to determine which compounds from the list, and what dosages of each, will be most beneficial, i.e., provide the highest likelihood for reducing the size of the tumor. Through continual monitoring of the patient, the compounds and dosages will be adjusted accordingly.

DESCRIPTION OF THE DRAWING

FIG. 1 presents an illustration of an inventive strategy of treating cancer by targeting multiple pathways.

DEFINITIONS

Below are provided certain definitions of terms used herein, many or most of which confirm common understandings of those skilled in the art.

Activating agent: As used herein, the term "activating agent" refers to an agent whose presence or level correlates with elevated level or activity of a target, as compared with that observed absent the agent (or with the agent at a different level). In some embodiments, an activating agent is one whose presence or level correlates with a target level or activity that is comparable to or greater than a particular reference level or activity (e.g., that observed under appropriate reference conditions, such as presence of a known activating agent, e.g., a positive control).

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Addressed: By "addressed", when used in reference to a process or pathway targeted by therapy as described herein is meant that the process or pathway will be altered by the administration of an inventive therapeutic protocol (e.g., by one or a combination of agents included in an inventive therapeutic protocol) toward normalcy, that is, toward the characteristic function of that process or pathway in a normal individual, or an individual that does not suffer from the cancer being treated.

Adult: As used herein, the term "adult" refers to a human eighteen years of age or older. Body weights among adults can vary widely with a typical range being 90 pounds to 250 pounds.

Agent: As will be clear to those skilled in the art, the term "agent" as used herein may refer to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Antagonist: As used herein, the term "antagonist" refers to an agent that i) inhibits, decreases or reduces the effects of another agent; and/or ii) inhibits, decreases, reduces, or delays one or more biological events. Antagonists may be or include agents of any chemical class including, for example, small molecules, polypeptides, nucleic acids, carbohydrates, lipids, metals, and/or any other entity that shows the relevant inhibitory activity. An antagonist may be direct (in which case it exerts its influence directly upon its target) or indirect (in which case it exerts its influence by other than binding to its target; e.g., by interacting with a regulator of the target, for example so that level or activity of the target is altered).

Antibody: As is known in the art, an "antibody" is an immunoglobulin that binds specifically to a particular antigen. The term encompasses immunoglobulins that are naturally produced in that they are generated by an organism reacting to the antigen, and also those that are synthetically produced or engineered. An antibody may be monoclonal or polyclonal. An antibody may be a member of any immunoglobulin class, including any of the human classes: IgG, IgM, IgA, and IgD. A typical immunoglobulin (antibody) structural unit as understood in the art, is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). In some embodiments, the term "full length" is used in reference to an antibody to mean that it contains two heavy chains and two light chains, optionally associated by disulfide bonds as occurs with naturally-produced antibodies. In some embodiments, an antibody is produced by a cell. In some embodiments, an antibody is produced by chemical synthesis. In some embodiments, an antibody is derived from a mammal. In some embodiments, an antibody is derived from an animal such as, but not limited to, mouse, rat, horse, pig, or goat. In some embodiments, an antibody is produced using a recombinant cell culture system. In some embodiments, an antibody may be a purified antibody (for example, by immune-affinity chromatography). In some embodiments, an antibody may be a human antibody. In some embodiments, an antibody may be a humanized antibody (antibody from non-human species whose protein sequences have been modified to increase their similarity to antibody variants produced naturally in humans). In some embodiments, an antibody may be a chimeric antibody (antibody made by combining genetic material from a non-human source, e.g., mouse, rat, horse, or pig, with genetic material from humans).

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Approximately: As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Combination therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Comparable: The term "comparable", as used herein, refers to two or more agents, entities, situations, sets of conditions, etc that may not be identical to one another but that are sufficiently similar to permit comparison therebetween so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: A "composition" or a "pharmaceutical composition" according to this invention, refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Metronomic therapy: As used herein, the term "metronomic therapy" or "metronomic chemotherapy" refers to the frequent, e.g., daily, administration of therapeutic agents at doses significantly less than the maximum tolerated dose (MTD). For example, metronomic administration of Cyclophosphamide at a low dose, e.g., 50 mg/day as compared with representative MTD doses of 600 mg/m$^2$-750 mg/m$^2$ for three weeks, has shown promising results in a wide range of cancers. N. Penel et al., *Critical Reviews in Oncology/Hematology*, 82:40-50 (2012).

Modulator: The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, such cancer or tumor is or comprises a cancer of the prostate, or tumor in the prostate. In some embodiments, the disorder or condition is metastatic cancer.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable salt: As used herein, the term "pharmaceutically acceptable salt" means a salt prepared by conventional means, and are well known by those skilled in the art. Suitable pharmaceutically acceptable salts include, but are not limited to, salts of pharmaceutically acceptable inorganic acids included but not limited to hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic, ammonium, tetaalkylammonium, and valeric acids and the like. General information on types of pharmaceutically acceptable salts and their formation is known to those skilled in the art and is as described in general texts such as "Handbook of Pharmaceutical Salts" P. H. Stahl, C. G. Wermuth, 1st edition, 2002, Wiley-VCH.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Reference: The term "reference" is often used herein to describe a standard or control agent or value against which an agent or value of interest is compared. In some embodiments, a reference agent is tested and/or a reference value is determined substantially simultaneously with the testing or determination of the agent or value of interest. In some embodiments, a reference agent or value is a historical reference, optionally embodied in a tangible medium. Typically, as would be understood by those skilled in the art, a reference agent or value is determined or characterized under conditions comparable to those utilized to determine or characterize the agent or value of interest.

Refractory: The term "refractory" as used herein, refers to any subject or condition that does not respond with an expected clinical efficacy following the administration of provided compositions as normally observed by practicing medical personnel.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.*, 2000, 92(3):205-216. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic.

Solid form: As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc.

In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: The term "therapeutically effective amount", as used herein and applied to any individual agent for use according to the invention means an amount which, when administered to the individual in need in the context of inventive therapy, will block, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure"

for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. The term "treating" also may include the reduction, stabilization, regression, elimination of cancer, more particularly for the reduction, stabilization, regression, elimination of epithelial cell related cancers related to abnormal growth of epithelial cells. The term "treating" may also include the promotion of cellular health in one or more organs or systems of the individual prescribed a treatment regimen as described herein.

Therapeutic index: As is known in the art, the term "therapeutic index" refers to a ratio of unacceptably unsafe dose to efficacious dose for a particular index. Specifically, the therapeutix index is the ratio of $TD_{50}$ (Dose that causes a toxic response in 50% of the relevant population) and $ED_{50}$ (dose that is therapeutically effective in 50% of the population).

Therapeutic regimen: A "therapeutic regimen", as that term is used herein, refers to a dosing regimen whose administration across a relevant population is correlated with a desired or beneficial therapeutic outcome.

Treatment: As used herein, the term "treatment" (also "treat" or "treating") refers to any administration of a substance (e.g., anti-receptor tyrosine kinases antibodies or receptor tyrosine kinase antagonists) that partially or completely alleviates, ameliorates, relives, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Vasculogenic Mimicry: Those of ordinary skill in the art will appreciate that the term "vasculogenic mimicry" is often used in the field to refer to tumor stem cell activity. Vasculogenic mimicry describes the formation of fluid-conducting channels by highly invasive and genetically dysregulated tumor cells without participation by endothelial cells and independent of angiogenesis. Two distinct types are identified: tubular type and patterned matrix type. The underlying induction of vasculogenic mimicry seems to be related to hypoxia, which may promote the plastic phenotype of tumor cells capable of creating this vasculature.

DETAILED DESCRIPTION OF CERTAIN EMBODIMENTS

The ensuing detailed description provides exemplary embodiments of the invention, and the disclosure of specific examples is not intended to limit the scope, applicability, or configuration of the invention. Guidance provided by this detailed description will permit and enable the skilled practitioner to put to use all the embodiments of the invention described herein and covered by the appended claims without undue experimentation. It will be understood that various changes may be made to the specific combinations and/or arrangement of the elements or compounds without departing from the description or coverage of the claims. Substitution of known equivalents or specific equivalents disclosed herein, for example for any named component of a pharmaceutical composition or therapeutic regimen described in the application, is within the skill of practitioners in the field of this invention.

In general, the present invention encompasses the recognition that many processes or pathways in an individual become altered in an individual suffering from cancer, compared to the same processes or pathways as they function in normal individuals not suffering from cancer. The pathways affected by cancer include metabolic pathways (e.g., regulation of glucose metabolism, hormone release and uptake, etc.), intercellular signaling pathways (e.g., regulation of cell proliferation, migration, circulation as a function of the regulation of cytokines and growth factors), and intracellular signaling pathways (e.g., differential gene expression, cell cycle perturbation or arrest, mutation, etc.).

Table 8 contains a listing of a variety of agents reported to be involved in pathways that have been found to be altered in patients diagnosed with cancer:

TABLE 8

Overexpressed or Downregulated Agents Involved in Cancer

VEGF
MMP-9
MMP-2
TNF-α
TGF-β
IL-6
Leptin
Thrombospodin-1
PI3K/AKT/mTOR
RAS/RAF/MEK/ERK (also known as MAP-Kinase (MAPK) Pathway, or ERK 1/2 Pathway)
Epidermal Growth Factor Receptor (EGFR)
HEDGEHOG
Cross-talk between HEDGEHOG and mTOR pathways
Insulin Growth Factor-1 (IGF-1)
Cross-talk between VEGF and EGFR pathways
BCL-2 (BCL-$X_L$ and MCL-1)
NF-kappaB (NFκB)
Mirk/Dyrk 1B
p53, p21 gene disruptions or mutations
Aerobic glycolysis, oxidative stress (Warburg Effect)
Vasculogenic mimicry (e.g. tumor stem cell activity)
Enzymatic or endocrine abnormalities
Mitochondrial respiration abnormalities
Apoptotic dysfunction and cell proliferation dysfunction For example, listed agents are involved in intracellular signal transduction pathways that drive tumor cell growth and/or in intracellular signaling pathways that promote angiogenesis, tumor invasion into normal tissues and the extracellular matrix, and/or tumor cell metastasis through lymphatic channels and the bloodstream to other tissues and organs. In some instances, established "cross-talk" or interaction between certain signaling pathways is deemed so extensive that it is included as an additional separate pathway.

The list presented in Table 8 is not in order of importance, among other things because the relative importance of certain pathways may well differ, at least to some extent, from patient to patient. Only an individualized, or "personalized" genomic, molecular, or proteomic tumor cell analysis would be able to provide insight into which pathways are relatively more powerful in their contribution to carcinogenesis and tumor progression in any one patient. In some embodiments, such a personalized approach may be utilized in selecting a particular regimen for use in accordance with the present invention, for example through periodic and/or regular testing of signaling proteins to select and/or monitor the impact of therapy and optionally to provide direction in optimizing individualized treatment and/or dosing.

The disruption of normal metabolic, intercellular signaling, and intracellular signaling pathways is a characteristic of cancer generally, although the range of pathways affected and the degree typically varies with the type of cancer and/or from patient to patient. Nevertheless, the principles of treatment developed herein are generally applicable; specific embodiments for treatment of particular tumors and/or patients can readily be developed and practiced by those skilled in the art, following the teachings provided herein.

As described herein, the present invention provides technologies for addressing multiple pathways involved in cancer through use of combination therapies. In many embodiments, combinations of therapeutic agents are selected so that each targeted pathway is addressed at least twice, and preferably three times, through use of the complete combination. By "addressed" is meant that the process or pathway will be altered by the administration of one or more of the composition components toward normalcy, that is, toward the characteristic function of that process or pathway in a normal individual, or an individual that does not suffer from the cancer being treated. Detection of normal or abnormal functioning of the pathways listed in Table 8 is within the skill of practitioners in this field.

Failure of Conventional Therapies

Among other things, the present invention encompasses the recognition that approximately 50% of all cases are diagnosed after local invasion or metastasis has occurred (Table 9), and long-term survival is low in this setting, particularly if distant metastases are present at the time of first diagnosis.

TABLE 9

Current Cancer Therapy Failure:
Approximately 50% of all major solid tumor cases are diagnosed after invasion or metastasis has occurred (percent five-year survival of solid tumor patients)

| Cancer Type | Invasion and/or Local Metastasis at Diagnosis (Stages II or III) | Distant Metastasis at Diagnosis (Stage IV) |
|---|---|---|
| Prostate | 100 | 28 |
| Ovarian (epithelial) | 52 | 18 |
| Breast | 62 | 15 |
| Melanoma | 64 | 15 |
| Kidney | 64 | 8 |
| Colorectal | 51 | 6 |
| Liver | 18 | 4 |
| Lung (non-small-cell) | 20 | 1 |
| Glioblastoma | 9 | — |
| Pancreatic (exocrine) | 5 | 1 |

Source - American Cancer Society (percentages are averages of Stage II, III A/B/C data, where applicable) 54% of above tumors were diagnosed at Stage II, III or IV in 2010 (American College of Surgeons)

Although significant progress has been made in cancer treatment, particularly with respect to hematologic malignancies, lymphomas and a small subset of metastatic solid tumors, the present invention encompasses the recognition that treatments for most metastatic solid tumors provide very limited benefit and are extremely expensive. For example, of twenty-five new US FDA cancer drug approvals for solid tumors over the past seven years, the average increase in overall survival and/or progression-free survival in the approval-based trial was 3.4 months (US FDA website). In addition, the average cost per quality-adjusted life year (QALY) for new cancer drugs is $200,000-$300,000. With health care expenditures projected to reach 20% of our gross national product within the next decade, value-equity and cost-effectiveness considerations for cancer treatment are becoming problematic (see, for example, Brock Oncologist 15 Suppl 1:36, 2010 PubMed PMID:20237216; Schnipper et al Clin Cancer Res 16(24):6004, 2010 Dec. 15 PubMed PMID:21169254)

The present invention appreciates that, over the past 50 years scientists have identified many, if not most, of the genetic alterations which cause cancer. Approximately 300,000 unique mutations have been discovered as a result of the sequencing of over 3,000 individual tumors. Although common solid tumors contain an average of 33-66 gene mutations that would be expected to alter their protein products, only a small percentage, called "driver" gene mutations, contribute directly to the generation and maintenance of the malignant phenotype. Drivers include genes involved in the stimulation of cell proliferation (oncogenes), which are mutationally activated or overexpressed, and genes that prevent inappropriate cell proliferation (suppressor genes), which are mutationally inactivated or deleted. On average, solid tumor cells contain at least 3-10 of these "driver" mutations. Hematologic malignancies (leukemias and lymphomas) average significantly fewer driver genes, making many of them easier to treat (Vogelstein et al Science 339(6127):1546, 2013 Mar. 29; PubMed PMID 23539594).

The present invention encompasses appreciation that consolidation of these findings has led to the concept that cancer results from deregulation of 8 key hallmarks or cellular pathways (Hanahan et al Cell 100(1):57, 2000 Jan. 7, PubMed PMID: 10647931; Hanahan et al Cell. 144(5):646, 2011 Mar. 4, PubMed PMID:21376230). These pathways involve proliferation stimulation and suppression (oncogenes and suppressor genes), invasion and metastasis, replicative mortality, angiogenesis, programmed cell death or apoptosis, cellular metabolism and energetics, genomic stability, and immune surveillance.

According to the present invention, the pathways that are most important for the survival of tumor cells in metastatic lesions, and therefore the most therapeutically relevant, are 1) angiogenesis, 2) apoptosis, 3) cellular metabolism and energetics, and 4) immune surveillance (Table 10):

TABLE 10

Hallmark Cancer Pathways: Signifncant Therapeutically Relevant Targets

| | |
|---|---|
| Tumor angiogenesis | Formation of new blood vessels, and modification of existing ones |
| Apoptosis (programmed cell death or suicide) | Loss of ability to undergo apoptosis in response to cellular damage or stress |
| Metabolism and energetics | Shift from complete oxidation of glucose to partial oxidation via aerobic glycolysis (Warburg effect), providing building blocks for cell proliferation and reducing ROS production |
| Immune surveillance | Tumor-mediated inhibition of inate and adaptive anti-tumor immune responses, and stimulation of pro-tumorigenic inflammatory responses |

Moreover, the present invention appreciates that targeting of any or all of the other pathways will not necessarily lead to tumor cell death or cell death within a relevant timeframe. For example, the present invention appreciates that many patients who cannot be cured by current therapy already have metastatic disease at the time of first diagnosis, so therapies that prevent invasion or metastasis may slow down subsequent spread, but cannot be curative. Additionally, the present invention observes that, since the average doubling time of solid tumors in patients is 100-400 days and individual tumor cells can divide within a few days, it is likely that at any one point in time, many cells in a tumor are either not dividing or are dormant. Thus, drugs targeting proliferation pathways cannot be expected to kill every tumor cell. Still further, the present invention appreciates that genomic instability and replicative immortality associated with cancer are most important during cancer development and/or operate on a time-scale that is not therapeutically accessible.

Modern or "targeted" cancer drug discovery has focused primarily on the discovery of small molecules or biologics (mainly antibodies) that interfere with the function of oncogene products. These proteins generally have an enzymatic activity that can be inhibited by the therapeutic, and have been referred to as "drugable" targets. The present invention identifies the source of various problems with such an approach.

For example, the present invention appreciates that, as mentioned above, oncogene-targeted therapeutics may not be efficient at killing non-dividing or dormant tumor cells. In addition, of 138 identified cancer-causing driver genes, 64 are oncogenes, but only 31 of these have a "drugable" enzymatic activity. Moreover, 74 of the 138 drivers are suppressor genes, where mutation results in functional loss of the gene product. Such alterations cannot be directly repaired or restored by small molecule or antibody therapy. Thus, 31+74 or 105 out of 138 currently identified cancer causing genes (76%) fall in the undrugable, or not easily drugable, category (Vogelstein et al Science 339(6127): 1546, 2013 Mar. 29, PubMed PMID: 235395943).

There is also significant heterogeneity between different types of cancer, and between tumors of the same histological type isolated from different patients with respect to what combination (typically about 3-10) driver genes, out of the possible 138, are mutated. Thus, the present invention observes that a particular pathway may be deregulated as a result of mutation in an oncogene in one patient, but the same pathway may be deregulated by an upstream or downstream undrugable suppressor gene mutation in another patient. Overlap between cellular pathways may also lead to redundancy across mutations in one tumor. In this scenario, targeted inhibition of a single oncogene may be ineffective, for example if compensated by another pre-existing mutation (Vogelstein et al Science 339(6127):1546, 2013 Mar. 29, PubMed PMID: 235395943; Hanahan & Weinberg Cell 100(1):57, 2000 Jan. 7, PubMed PMID: 10647931; Hanahan & Weinberg Cell 144(5):646, 2011 Mar. 4, PubMed PMID:21376230). The present invention appreciates that these realities are the source of problems with many conventional chemotherapeutic treatment strategies.

The present invention further appreciates another source of a problem with conventional chemotherapeutic treatment strategies for cancer: tumor or angiogenic rebound in between doses or after cessation of treatment with toxic compounds. The present invention provides the specific insight that these problems highlight a need for effective therapy, particularly combinations, that can be administered chronically (i.e. for extended periods).

The present invention further encompasses the recognition of the source of problem with many traditional chemotherapeutic treatment strategies that results from genomic instability of tumors. That is, tumors undergo additional mutation and selection after treatment is initiated, resulting in drug resistance via enhanced drug efflux, metabolism or a compensatory driver mutation. The present invention appreciates that, even with the use of combinations of oncogene-targeted and traditional cytotoxic therapies, current drug discovery paradigms, particularly those focused on treatment of solid tumors, tend to produces drug that are effective against only one or a few types of cancer, are only effective in a sub-set of patients with one type of cancer and/or provide, on average, only 3 additional months of life.

Still further, the present invention appreciates that the current regulatory landscape, which was designed primarily to avoid unanticipated combination or synergistic toxicity in clinical trials involving non-life-threatening diseases, discourages development of combination therapies, particularly when coupled with the extended timeframe (typically 10-14 years) and daunting pricetag (on average several hundred million dollars to discover and develop each new cancer drug, with estimates varying from $43 million to more than $2 billion/drug, Adams & Brantner Health Aff (Millwood) 25(2):420, 2006 March-April, PubMed PMID: 16522582, DiMasi et al J Health Econ 22(2):151, 2003 March, PubMed PMID:12606142). Particularly discourages is the development of combination therapy approaches that utilize agents that are not expected to be efficacious alone.

Indeed, the present invention appreciates that various additional scientific, resource and business constraints have hindered rational or efficient approaches to combination therapy development in oncology (Humphrey et al J Natl Cancer Inst 103(16):1222, 2011 Aug. 17, PubMed PMID: 21765011, Levinson Science 38(5975):137, 2010 Apr. 9, PubMed PMID:20378778, Woodcock et al N Engl J Med 364(11):985, 2011 Mar. 17, PubMed PMID:21323535). These constraints include the potential for unacceptable toxicity when combining two conventional chemotherapeutic agents, because even modern or targeted therapeutics are most active and typically used individually at their maximum tolerated dose (MTD). In other words, they have a narrow therapeutic index (TI). Additionally, there is an historically low predictability of Phase III success with Phase II combination data, difficulties associated with patient recruitment (only 3% of cancer patients volunteer for clinical trials), and hesitation by companies to combine their proprietary investigational compound with one from another company (Maitland et al Clin Cancer Res 16(21):5296, 2010 Nov. 1, PubMed PMID:20837695). The present invention encompasses the recognition that these constraints have limited the development of certain approaches to cancer therapy, and particularly have led development away from particularly strategies that the present invention defines as clearly desirable, targeting multiple therapeutically relevant hallmark pathways (e.g., combinations of angiogenesis, apoptosis, cellular metabolism and energetics, and immune surveillance) as described herein.

Thus, the present invention appreciates that, while much progress has taken place in the past 40 years, current therapies, led by maximum tolerated dose chemotherapy, have shown significant limitations in eliminating the disease progression over longer timeframes and later stage disease. Moreover, although use of customized cocktails of multiple targeted agents, or discovery of single drugs with multi-targeting capabilities, has been discussed in the field, it is an approach that has not been adequately defined or explored. The present invention provides specific strategies for targeting multiple pathways, and furthermore defines classes of agents, with specific exemplification, that can effectively be used together to treat cancer.

Targeting Multiple Pathways

As discussed above, the present invention provides the teaching that effective cancer therapies utilize a combination of agents that together target multiple hallmark cancer pathways. In certain embodiments, a utilized combination includes a collection of agents that together address each targeted pathway at least twice. In some embodiments, at least one such pathway is targeted at least three times by a utilized combination. In some embodiments, each such pathway is targeted at least twice or at least three times by a utilized combination.

Those skilled in the art, reading the present disclosure and its identification of pathways to be targeted, as well as its teaching of assembling collections of agents that both target multiple pathways and, in some embodiments, target individual pathways more than one, will readily be able to select appropriate agents for combination use in accordance with the present invention. A variety of strategies for targeting particular pathways are known in the art and/or described herein.

Below, pathways of particular interest for targeting in accordance with the present invention are discussed in further detail. A representative strategy for targeting each of these pathways is illustrated, for example, in FIG. 1:

Angiogenesis

"Angiogenesis" refers to the generation of new blood vessels into a tissue or organ. Under normal physiological conditions, humans or animals only undergo angiogenesis in very specific restricted situations. For example, angiogenesis is normally observed in wound healing, fetal and embryonal development, and formation of the corpus luteum, endometrium, and placenta. The endogenous control of angiogenesis is a highly regulated system of angiogenic stimulators and inhibitors. The control of angiogenesis has been found to be altered in certain disease states and, in many cases, the pathological damage associated with the disease is related to uncontrolled angiogenesis.

Angiogenic regulators in the human or animal body can generally be divided into two main groups: (1) pro-angiogenic regulators that directly or indirectly stimulate capillary and blood vessel growth, and (2) anti-angiogenic regulators or endogenous inhibitors that retard angiogenesis. Examples of pro-angiogenic regulators include, for example, Tumor Necrosis Factor (TNF-α), Granulocyte Colony-Stimulating Factor (GCSF), and Vascular Endothelial Growth Factor (VEGF). Examples of anti-angiogenic regulators include, for example, Interferon gamma (IFN-γ), Thrombospondin-1, endostatin, and angiostatin.

In many diseases and in cancer in particular, angiogenesis is an important process that supports the disease, and therefore the process of angiogenesis itself becomes a target for therapeutic intervention. Recent medical research has documented the essential role angiogenesis plays in supporting disease. Angiogenesis is particularly well documented as a pivotal process in cancer, wherein avascular benign tumors are transformed into life-threatening malignant tumors.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants (pro-angiogenic regulators) induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis can avert the damage caused by the invasion of the new microvascular system.

Persistent, unregulated angiogenesis occurs in a multiplicity of disease states, including tumor metastasis and abnormal growth by endothelial cells, and angiogenesis supports the pathological damage seen in these conditions. The diverse pathological states created due to unregulated angiogenesis have been grouped together as angiogenic dependent or angiogenic associated diseases. Therapies directed at control of the angiogenic process seek to abrogate or mitigate development, maintenance, and/or expansion of these diseases. Angiogenesis has become an important target for cancer treatment with the recognition that it is one of the critical events necessary for cancer growth and metastasis. As a tumor develops, its size is limited by the diffusion of metabolites from existing blood vessels. Tumor angiogenesis is essential for cancerous tumors to keep growing and spreading.

As a tumor grows, cells at the center become starved of oxygen, inducing the expression of a transcription factor, hypoxia inducible factor-1 (HIF-1), which upregulates the expression of a range of angiogenic factors. Growth factor signaling also initiates HIF-1 activity, pre-empting the need for growing cells to maintain oxygen homeostasis. As a result, HIF-1 itself has been isolated as a therapeutic target for cancer.

Approximately 9 out of 120 approved cancer drugs target angiogenesis, predominantly via inhibition of the vascular endothelial growth factor (VEGF) pathway. Despite initial responses, the clinical benefits obtained in terms of progression-free survival or overall survival have been more modest than expected, due to intrinsic or acquired resistance and possibly also rebound mechanisms. In addition, combination approaches of anti-angiogenic therapies with oncogene-targeted or cytotoxic therapies have not produced synergistic responses in the clinic. A more recent approach, called metronomic anti-angiogenic therapy, takes advantage of the finding that certain cytotoxic anti-tumor drugs, such as cyclophosphamide, are anti-angiogenic when administered daily at low, non-toxic doses (25-41). The present invention encompasses the recognition that this approach may decrease the potential for rebound angiogenesis and enhance the potential for synergism in combination settings.

In some embodiments, the present invention utilizes metronomic anti-angiogenic therapy in combination with targeting of other hallmark pathways, as described herein. In some particular embodiments, the present invention utilizes metronomic anti-angiogenic therapy with an agent that also targets another pathway. To give but one example, in some embodiments, the present invention utilizes metronomic cyclophosphamide; in addition to its anti-angiogenic effects, metronomic cyclophosphamide can enhance anti-tumor immune responses.

Apoptosis

Normal mammalian cells have a variety of programmed cell death pathways, designed to induce cellular suicide or apoptosis when cells are damaged or exposed to sub-optimal conditions. Apoptotic cell death prevents accumulation of undesirable mutations and, unlike necrotic cell death, eliminates cells without causing local tissue damage. Many of the ways that tumors avoid engagement of apoptosis pathways are well-understood, frequently involving overexpression of apoptosis inhibitor proteins (42-43).

Although more difficult to target than enzymes involved in cell proliferation and angiogenesis, a number of drugs are under development in this area. The present invention recognizes a potential pitfall in this approach, and particularly in the understandable incentive to combine pro-apoptptic agents with existing anti-proliferative agents. That is, the present invention appreciates that over-expression of proteins which inhibit apoptosis allows the tumor cell to continue to accumulate mutations and to divide in an uncontrolled fashion. Pharmaceutical approaches to reverse this increasing insensitivity to apoptosis should cause the tumor cell to be more susceptible to the programmed cell death pathways. Given the propensity in cancer therapy to combine agents for added benefit, it would seem logical to also treat the patient with cytotoxic, apoptosis-inducing agents. The present invention appreciates, however, that, paradoxically, these cytotoxic agents at high doses cause a delay in cell cycle progression. Thus, cells which survive the cytotoxic insult are more likely to be temporally non-proliferating and less sensitive to apoptosis inducing stimuli. Therefore, in accordance with the present invention, it is possible that certain pro-apoptotic drugs will work best under conditions where tumor cells are actively trying to divide, rather than against dormant or non-dividing cells. In some particular embodiments of the present invention, anti-proliferative agents are not utilized in combination with pro-apoptotic agents. In some embodiments, pro-apoptotic agents are used in combination with one or more agents that promotes or supports cell proliferation. In some embodiments, however, patients are treated with both anti-proliferative and pro-apoptotic agents.

Immune Surveillance

The potential for induction of anti-tumor immune responses (immune surveillance) has been appreciated for over 100 years, but the fundamental mechanisms by which tumors evade immune destruction have only recently been elucidated. It is now clear that tumors express and secrete factors that shift the balance of the innate or inflammatory immune response from anti-tumorigenic to pro-tumorigenic. This is accomplished by suppressing anti-tumor natural killer (NK) cell and cytotoxic T lymphocyte (CTL) function, and enhancing general pro-inflammatory responses which stimulate tumor growth and tumor angiogenesis. In addition, despite the fact that tumors express, on average, 33-66 mutant proteins, several of which should be recognizable as foreign antigens, tumors block antigen presentation, as well as induction and maturation of adaptive immune responses (44).

Elucidation of these immune surveillance mechanisms has resulted in the development and approval of at least one therapeutic (ipilimumab), which directly stimulates anti-tumor immune responses. This compound has produced long-term responses in a sub-set of malignant melanoma patients, but is also associated with significant toxicity, due to activation of auto-immune responses in normal tissues (45).

Thus, the present invention appreciates that it is possible to restore immune surveillance in cancer patients. The present invention further recognizes that combination of agents that hit related immune response mechanisms and other pathways will significantly increase response rate.

Metabolism and Energetics

Aberrant metabolism related to energy production was first described in tumor cells almost 90 years ago by Otto Warburg, who observed that tumors have a higher than normal rate of aerobic glycolysis. The reasons for this have only recently become apparent (46-50). Most normal epithelial cells are not actively dividing. Non-dividing cells in normal tissues have minimal requirements for catabolic intermediates, have a plentiful oxygen supply and thus, can afford to fully oxidize glucose via glycolysis and the tricarboxylic acid cycle (TCA), and then use the NADH and FADH generated to make ATP by oxidative phosphorylation. This strategy is more efficient than glycolysis with respect to ATP production, but results in loss of glycolytic and TCA intermediates that could otherwise be used in anabolic pathways to make ribose sugars for nucleotides, lipids, and amino acids for proteins. Production of ATP by oxidative phosphorylation is also 100-times slower than glycolysis-driven ATP production. In addition, oxidative phosphorylation generates reactive oxygen species (ROS), which can damage cellular constituents, leading to apoptosis.

Normal cells have several anti-oxidant mechanisms, don't need to continually make large amounts of DNA, RNA, lipid or protein, and can afford to make ATP relatively slowly. Tumor cells, on the other hand, divide more frequently than normal cells, requiring significantly larger pools of DNA, RNA, lipid and protein precursors. Although a significant amount of lactic acid and only 2 net ATPs are produced via glycolysis, rapid turnover can satisfy cellular energy requirements and lactic acid can be recycled to glucose in the liver. Use of glycolytic pathways for metabolism allows tumor cells to produce the large amounts of precursors needed for uncontrolled cell proliferation. Also, by de-emphasizing oxidative phosphorylation, tumor cells can reduce production of ROS. Reducing ROS is important for tumor cells because they not able to repair and recover from non-specific oxidative damage as easily as normal cells. Finally, tumors are continuously exposed to hypoxic (low oxygen) conditions as they grow and struggle to induce formation of new blood vessels. Decreasing their reliance on oxygen-dependent oxidative phosphorylation provides tumor cells with an additional survival advantage in this setting.

During the past decade, it has been found that the shift from oxidative phosphorylation-based energy production to an aerobic glycolysis-based approach in tumor cells requires a large number of primary and secondary alterations in multiple pathways, including those involved in cell proliferation, apoptosis and angiogenesis. For example, mutational activation of certain oncogenes leads, among other things, to increased expression of a glucose transport protein that is required to accumulate sufficient glucose to power anaerobic glycolysis (51). The oncogenes and the glucose transporter are components of the mammalian target of rapamycin (mTOR) signaling pathway that integrates signals controlling protein biosynthesis, cell growth, cell cycle progression, energy metabolism, angiogenesis and apoptosis (52-54). Since this pathway is centrally involved in energy metabolism, including glucose utilization and production, it is not surprising that it also plays a role in the etiology and treatment of type 2 diabetes.

The present invention encompasses the recognition that it is desirable to treat cancer by targeting metabolism and/or energetics pathways in tumor cells, particularly while targeting other pathways, as described herein. The present invention particularly observes that metformin, a well-tolerated first-line drug of choice used to suppress glucose production in type 2 diabetes, has also been found to reverse several of the aberrant metabolic features of tumor cells (55-67).

Agents for Use in Inventive Therapeutic Regimens

As described herein, it has become clear that hallmark cancer pathways overlap and cooperate with each other, looking much like the subway map from a large city. Three to ten very specific mutations or defects among the many hundreds of "stations in the system" can be sufficient to turn a normal cell into a cancer cell. Redundancy and genomic instability, leading to drug resistance and/or new cancer causing mutations can compensate quickly when one or perhaps even two defects are corrected by targeted therapeutics. On the other hand, it is statistically much more likely that any two or more pathway interventions will cause an unacceptable breakdown of the system in normal cells, than selective killing of tumor cells, because normal cells require and use all of the same pathways, but without the benefits of genomic instability.

In light of these realities, the present invention identifies sources of problems with conventional approaches to the development and/or implementation of strategies for the treatment of cancer. As described herein, approaches that individually target proliferation stimulation and suppression (oncogenes and suppressor genes), invasion and metastasis, replicative mortality, angiogenesis, programmed cell death or apoptosis, cellular metabolism and energetics, genomic stability, and immune surveillance, may be ineffective against particular cancer cells, including for example cells that may be in a dormant state, or cells that arise in late stage (e.g., metastasized) cancers. Conventional focus on "drug-gable" significantly restricts options. Moreover, the typical reliance on narrow-therapeutic-index agents, usually utilized at or near their maximum tolerated dose, complicates or even prevents development of effective combination therapies through conventional strategies.

The present invention provides new and improved strategies for developing and/or implementing cancer therapy. Among other things, the present invention appreciates the benefits of targeting multiple pathways, and furthermore appreciates that combinations of particular interest both target multiple pathways and target individual pathways in multiple ways.

Moreover, the present invention encompasses the recognition that in certain embodiments it is desirable to utilize agents (and/or dosing regimens) with a broader therapeutic index than that commonly observed for conventional chemotherapeutic agents. Such conventional agents are typically characterized by a therapeutic index within the range of about 2 to about 5. In some embodiments, the present invention utilizes one or more agents whose therapeutic index is within the range of about 10 to about 100.

The present invention encompasses the particular insight that therapeutic agents developed for and/or effective in treatment of certain non-life-threatening conditions, and particularly of chronic conditions, may target one or more pathways that, as described herein, are hallmark cancer pathways, and may be useful in combination therapies as described herein. Such agents typically show a wide safety margin, particularly when developed for long-term therapy. Indeed, agents approved for long-term therapy of non-life-threatening diseases, disorders, or conditions typically have had to meet stringent regulatory risk-benefit requirements. The lower the morbidity associated with the condition being treated, the lower the acceptable risk for its therapy. In accordance with certain embodiments of the present invention, agents developed for treatment of low-morbidity, chronic illnesses that target one or more hallmark cancer pathways as described herein are particularly useful in inventive therapeutic regimens for the treatment of cancer.

Still further, the present invention encompasses the recognition that certain traditional and/or nutraceutical medicine approaches, including complementary and alternative medicines (CAM) identify and/or utilize well-tolerated agents that target the relevant pathways described herein. In many embodiments, such agents may be or include purified or partially purified natural products or extracts. In some embodiments, such products have been identified and/or characterized as a result of decades, or even centuries, of observational trial and error. Typically, traditional and/or nutraceutical agents are well tolerated (i.e., are associated with minimal toxicities), and show high therapeutic indices (e.g., typically well above 10, and often within the at least 10 to at least 100 range described herein, sometimes even higher).

Among other things, therefore, the present invention provides cancer therapies that utilize combinations of agents that show high therapeutic indices and/or together target multiple allmark cancer pathways, preferably in multiple ways.

In some embodiments, natural compounds and supplements referred to as "Nutraceuticals", "Natural Medicines", or "Phytomedicines" are suitable for use in combination therapies of the invention. As described herein, such nutraceuticals may be selected based on the quality and number of preclinical or clinical studies presenting either credible evidence of clinical anti-tumor activity in human cancer patients or demonstrating their ability to affect one or more tumorigenic and angiogenic signaling pathways described herein, and/or to interfere with the noted "cross-talk" between pathways that is essential for tumor cells to proliferate, for angiogenesis to flourish, and for tumor progression.

In some embodiments, combination therapies of the present invention may include, in addition to one or more nutraceutical compounds, any of a number of non-chemotherapeutic or chemotherapeutic drugs for their desired effects on metabolic or signaling pathways. Such non-chemotherapeutic or chemotherapeutic drugs may address the same pathway(s) as nutraceutical components of a composition of the invention or may address pathways not adequately altered by administration of nutraceutical components. As these components are drugs and thus subject to regulations, they normally may only be included by order of a physician or qualified and licensed healthcare practitioner. Exemplary non-chemotherapeutic drugs include but are not limited to Metformin, Cyclophosphamide, Naltrexone, Melatonin, and others. Those of ordinary skill in the art will appreciate that some or all of these agents may, in some embodiments, be utilized in accordance with their approved drug regimens or protocols. Alternatively or additionally, in some embodiments, these agents are or may be utilized at different doses, and/or according to different regimens or protocols than those for which they have been approved. In some embodiments, such doses and/or regimens or protocols are known and/or established in the art. In some embodiments, order of a physician or qualified and licensed healthcare practitioner may not be required for such administration. For example, those skilled in the art will appreciate that melatonin has a variety of well-established uses (including as otherwise described herein), some but not all of which have been subject to formal regulatory approval. In some embodiments, one or more non-chemotherapeutic drugs are chosen as significant components of the methods and compositions described herein, based on research demonstrating their capacity to suppress or disrupt key signaling pathways involved in cancer, more particularly for the treatment of epithelial cell related cancers cancer. The evidence supporting their anti-cancer efficacy varies from agent to agent, but in almost all cases there is sound published evidence of anti-cancer activity, and in some cases anti-angiogenic activity.

Clinical trials mostly offer access to Phase I or II studies of targeted therapies that, again, may target just one marker, or in some cases, several markers. Currently approved cancer therapies typically involve the selection of a single chemotherapeutic agent found to have a direct impact on cancer cell growth and administering as much of that agent as can be tolerated by the patient without being fatally toxic. One concept embodied by the present invention is that by addressing only one pathway with a chemotherapeutic drug leaves several other cancer-supportive pathways unchecked or cancer-suppressive pathways unenhanced, which may leave the cancer alternative pathways of angiogenesis, growth, or migration. By contrast, with inventive therapeutic protocols described herein, although potency of particular individual agents (e.g., natural compounds and/or non-chemotherapeutic drugs) against any one target may be less than that of a rationally designed pharmaceutical, the combination of multiple agents (and particularly of multiple natural compounds [e.g., Nutraceuticals] and/or non-chemotherapeutic pharmaceuticals), preferably including multiple agents against individual target pathways, has the potential to address multiple pathways with multiplicative pharmacologic potencies.

In some embodiments, provided inventive therapeutic regimens utilize only nuctraceutical agents and/or agents developed and/or approved for non-cancer conditions (e.g., non-chemotherapeutic agents). In some embodiments, provided inventive therapeutic regimens utilize at least one agent that has been approved for treatment of one or more cancers; in some such embodiments, such agents is utilized in accordance with the present invention according to a dosing regimen that is different from the approved cancer treatment regimen. In some embodiments, such different regimen involves administration of lower individual doses and/or lower overall exposure over a period of time, as compared with a reference (e.g., approved) cancer therapeutic regimen utilizing the same agent.

Exemplary agents useful for inclusion in certain embodiments of inventive combination therapy regimens for the treatment of cancer are discussed individually below. For many of them, there are a number of equivalent agents that will be known to those skilled in the art.

Nutraceutical and/or Non-Chemotherapeutic Agents

Alpha-Lipoic Acid

Alpha-Lipoic Acid is a fatty acid produced by the body for converting glucose into energy. It is also known to have antioxidant properties beneficial for fighting harmful chemicals that contribute to onset of disease. It is also referred to by the following names: Acetate Replacing Factor, A-Lipoic Acid, Acide Alpha-Lipoïque, Acide Alpha-Lipoïque R, Acide DL-Alpha-Lipoïque, Acide Lipoïque, Acide Thioctique, Acide 1,2-dithiolane-3-pentanoïque, Acide 1,2-dithiolane-3-valérique, Acide 5 Valérique (1,2-dithiolan-3-yl), Acide 6,8-dithiooctanoïque, Acide 6,8-Thioctique, Acido Alfa Lipoico, Alpha-Lipoic Acid Extract, ALA, Biletan, Extrait d'acide Alpha-Lipoïque, Lipoic Acid, Lipoicin, R-ALA, R-Alpha-Lipoic Acid R, S-Alpha Lipoic Acid, (R)-Lipoic Acid, R-Lipoic Acid, RS-Alpha-Lipoic Acid Thioctacid, Thioctan, Thioctic Acid, 1,2-dithiolane-3-pentanoic acid, 1,2-dithiolane-3-valeric acid, 6,8-dithiooctanoic acid, 6,8-thioctic acid, 5-(1,2-dithiolan-3-yl) valeric acid.

Although manufactured by the body and found in trace amounts in foods such as spinach, broccoli, peas, Brewer's yeast, brussel sprouts, rice, bran, potatoes and organ meats (kidney, heart, liver), it is the concentrated amounts of Alpha-Lipoic Acid found in supplements that provides the best antioxidant effect. When produced endogenously in plants or humans, it is complexed with proteins. However, when taken in supplement form, it is not bound to proteins and is likely in a 1000 fold greater amount than can be obtained through regular diet.

Alpha-Lipoic Acid is known to inhibit TNF-α-induced NF-kappaB pathway activation which leads to endothelial activation and monocyte adhesion, which are the initial steps to leading to inflammation caused by oxidative stress. Alpha-Lipoic Acid has also been found to inhibit copper- and iron-mediated oxidative damage and accumulation via chelation of free metal ions. This process suppresses the induced oxidative damage caused by reactions that produce reactive free radicals. The addition of Alpha-Lipoic Acid to cultured cells has been shown to activate PKB/Akt-dependent signaling resulting in increased survival of neurons.

Several Alpha-Lipoic Acid supplements are presently manufactured. It is important to note that Alpha-Lipoic Acid contains an asymmetric carbon, meaning there are two possible optical isomers that are mirror images of each other (R- and S-isomers). Most supplements may contain a 50/50 racemic mixture of each R-Alpha-Lipoic Acid and S-Alpha-Lipoic Acid. Supplements that contain only the R-isomer are available but the level of purity may be uncertain. Since taking Alpha-Lipoic Acid with a meal decreases its bioavailability, it is generally recommended that it be taken on an empty stomach (one hour before or two hours after eating).

Commercial suppliers for ALA include Source Naturals Alpha Lipoic Acid, Swanson Ultra Alpha Lipoic Acid, NOW Foods Alpha Lipoic Acid, Bluebonnet Alpha Lipoic Acid, Country Life R-Lipoic Acid, Solgar Alpha Lipoic Acid.

Curcumin

The active ingredient in the spice Turmeric is curcumin, which is extracted from the rhizome of the plant *curcuma longa* Linn. Curcumin is the principal curcuminoid, or polyphenolic compound found in such extracts, with others including demethoxycurcumin and bisdemethoxycurcumin.

Turmeric is also known as *Curcuma, Curcuma aromatica, Curcuma domestica, Curcumae longa*, Curcumae Longae Rhizoma, Curcumin, Curcumine, Curcuminoid, Curcuminoïde, Curcuminoïdes, Curcuminoids, Halada, Haldi, Haridra, Indian Saffron, Nisha, Pian Jiang Huang, Racine de Curcuma, Radix Curcumae, Rajani, Rhizoma Cucurmae Longae, Safran Bourbon, Safran de Batallita, Safran des Indes, Turmeric Root, Yu Jin.

Curcumin's mechanisms of action include inhibition of several cell signaling pathways, effects on cellular enzymes such as cyclooxygenase and effects on angiogenesis and cell-cell adhesion. Curcumin also affects gene transcription and induces apoptosis.

Curcumin is effective at inhibiting the signal transduction pathway of PI3K/Akt, MAPK, and NF-κB activation, as well as the Sonic Hedgehog (Shh) signaling pathway by down-regulating the Shh protein. In turn, reduction of beta-catenin, the activated/phosphorylated form of Akt and NF-κB, triggers apoptosis.

The oncogenic pathways inhibited by curcumin include down-regulation of epidermal growth factor receptors (EGFR and erbB2), Insulin-like growth factor type-1 receptor (IFG-1R), sonic hedgehog (SHH)/GLIs) and Wnt/b-catenin and PARP, IKK, EGFR, JNK, MAPK and 5-LOX. In addition curcumin suppresses downstream signaling elements such as signal transducers and activators of transcription (STATs), PI3K/Akt, nuclear factor-kappa B (NF-κB), and its targeted genes, including IL-6, COX-2, and MMPs.

Curcumin is most beneficial when take in liposomal form. The most bioavailable supplement is Life Extension's Super Bio Curcumin® which absorbs into the bloodstream up to seven times better than conventional 95% curcumin extract. Alternatively or additionally, another highly bioavailable form of Curcumin is Euromedica CuraPro BCM-95® or Progressive Labs Curcumin BCM-95®. Other curcumin supplements add piperine, (*Piper nigrum*) to enhance absorption of curcumin in their products. However, the interactions of piperine with many medications can cause problems including toxicity if taken in high doses. Curcumin can exist in the tautomeric forms that include the 1,3-diketo and the enol form. The most stable form of Curcumin is its planar enol form. Additionally Biomar™ Curcumin is commercially available.

Alternatives to Super Bio-Curcumin and/or Euromedica BCM-95® include all 95% Curcumin supplements including Jarrow Formulas Curcumin 95, NOW Foods Curcumin, Genceutic Naturals Curcumin BCM-95, etc.

Turmeric Extract in fact only provides 2-6% curcumin, and it can be important to take Curcumin in higher levels. Any supplement that is lower than 95% Curcumin is not as effective. Only about 50-60% is absorbed (in contrast to 96% absorption with Super Bio Curcumin®). In addition, dilutions with other supplements such as bioperine reduce bioavailability, and as mentioned piperine can interact with other medications negatively. Synthetic, petroleum-derived curcumin supplements may only contain on or two of the important curcuminoids found in natural supplements. Resveratrol is not a substitute. There are "Ultimate Antioxidants" that contain Curcumin and other important antioxidants, but do not reach the quality or bioavailability of other supplements (e.g. Natural Factors®Ultimate Antioxidant claims 95% total curcuminoids, but does not specify which, and has 13 other factors that may or may not be beneficial).

In some embodiments, when administering Curcumin, consideration may desirably be given to factors impacting a patient's ability to absorb administered material. For example, if may be desirable or necessary to reduce or eliminate one or more Curcumin otherwise desirable or appropriate Curcumin doses if a patient has suffered damage (including, for example, removal by surgery; see Examples) of part of his or her gastrointestinal tract. Alternatively or additionally, it might be desirable to administer Curcumin in a more palatable or bioavailable form (e.g., as a liquid) to certain patients.

Genistein

Genistein is an isoflavone extracted from fermented soy. It is also referred to as Basidiomycetes Polysaccharide, Fermented Genistein, Fermented Isoflavone, GCP, Genistein Polysaccharide, Génistéine du Polysaccharide Combiné, Isoflavone Combined Polysaccharide, Polysacaridos Combinados de Genisteina, and Soy Isoflavone Polysaccharide.

Genistein plays an important role in reducing the incidence of breast and prostate cancers. It has been shown that genistein inhibits the activation of NF-kappaB and Akt signaling pathways, both of which are known to maintain a homeostatic balance between cell survival and apoptosis. Furthermore, genistein has been found to have antioxidant properties, and shown to be a potent inhibitor of angiogenesis and metastasis. In addition, genistein works to target endogenous copper which leads to pro-oxidant signaling and consequent cell death.

Genistein has also been shown to downregulate the IGF-1/IGF-1R signaling pathway and inhibit cell growth in hormone refractory PC-3 prostate cancer cells. Treatment with Genistein resulted in a significant inhibition of IGF-1- stimulated cell growth. Treatment with Genistein also strongly attenuated IGF-1-induced β-catenin signaling that correlated with increasing the levels of E-cadherin and decreasing cyclin D1 levels in PC-3 cells. In addition, genistein inhibited T-cell factor/lymphoid enhancer factor (TCF/LEF)-dependent transcriptional activity.

Genistein has also been shown to inhibit VEGF-induced endothelial cell activation by decreasing PTK activity and MAPK activation, resulting in anti-angiogenic activity. Exposure to genistein also decreased activation of JNK and p38, not ERK-1/2, induced by VEGF. It also inhibited activity of MMPs.

Genistein is readily bioavailable. The purest form is commercially available in 99% purity from laboratories including LC Labs, Enzo Life Sciences, BioVision. However, not all forms are suitable for human consumption. Less preferable sources are the soy isoflavone supplements that contain genistein at lower concentrations.

Melatonin

Melatonin is a hormone secreted by the pineal gland and found naturally in the body. Melatonin is also synthetically produced in a laboratory for medical use. It is also referred to as MEL, Melatonina, Mélatonine, MLT, N-acetyl-5-methoxytryptamine, N-Acétyl-5-Méthoxytryptamine, and Pineal Hormone.

Melatonin has known, potent anti-oxidant, anti-inflammatory, and anti-tumor properties, but it also influences oncogenic pathways including mTOR, which plays a role in pancreatic cancer. Melatonin induces pro-apoptotic signaling in pancreatic cancer cells; restores mitochondrial function which in turn restores apoptosis of pancreatic cancer cells; and enhances patients' responses to Capecitabine (XELODA). Leja-Szpak, et al., *J Pineal Res.*, 49(3):248-55 (2010); Gonzalez, et al., *J Pineal Res.*, Epub 2010; Ruiz-Rabelo, et al., *Pancreas*, Epub 2010.

Melatonin is known to suppress tumor angiogenesis by inhibiting HIF-1α stabilization under hypoxia, leading to a decrease in VEGF expression. Melatonin also inhibits cell proliferation and migration of HUVECs and also decreases both the VEGF protein secreted and the protein produced by pancreatic carcinoma cells. In addition, VEGF mRNA expression is known to be down-regulated by melatonin. Melatonin has also been shown to inhibit cell proliferation and induce apoptosis in cancer cells in vitro by simultaneously suppressing the COX-2/PGE2, p300/NF-κB, and PI3K/Akt/signaling and activating the Apaf-1/caspase-dependent apoptotic pathway.

The most beneficial form of Melatonin is in pharmaceutical grade (not "natural", animal, or bovine) supplements having a purity of 99% or greater. The bioavailability of melatonin varies widely. A bioavailable source is Thorne Research Melatonin-5™. Melatonin has several clinical analogs that bind to melatonin receptors, but ultimately have a different function (most commonly as a sleep aid only or antidepressant only). These include S20242, agomelatine, and 2-Bromomelatonin. When melatonin, ramelteon, tasimelteon, PD-6735, and agomelatine are compared, agomelatine is the analogue that exhibits the most potential for the treatment of major depression. Unlike melatonin, agomelatine is a competitive antagonist of human and porcine serotonin (5-HT2C) receptors and human 5-HT2B receptors.

Alternatively or additionally, there are medications that include impurities and low levels of melatonin, for example, Circadin used for insomnia. Melatonin should only be taken in synthetic (man-made) form. The alternative that is extracted from ground-up cow pineal glands is rarely used, as it may spread disease.

Melatonin is reported to be useful in the treatment of a variety of diseases, disorders, and conditions, and recommended dosing regimens include, for example:

For age-related macular degeneration (vision loss with age), three milligrams of melatonin have been taken by mouth nightly at bedtime for six months.

To improve body temperature regulation in the elderly, 1.5 milligrams of melatonin has been taken by mouth nightly for two weeks.

For Alzheimer's disease or cognitive decline, melatonin has been taken by mouth in doses of 1-10 milligrams daily for 10 days up to 35 months.

For inflammation, melatonin has been taken by mouth in doses of 10 milligrams nightly for six months or five milligrams the night before and one hour before surgery.

For asthma, three milligrams of melatonin has been taken by mouth for four weeks.

For withdrawal from benzodiazepines (antianxiety agents), doses of 1-5 milligrams have been taken by mouth daily for from several weeks up to one year.

For cancer, melatonin has been taken by mouth in doses of 1-40 milligrams daily, with 20 milligrams being most common, for several weeks to months.

Melatonin has been applied to the skin.

For chronic fatigue syndrome, five milligrams of melatonin has been taken by mouth five hours before bed for three months.

For COPD (chronic lung disorder causing breathing difficulty), three milligrams of melatonin has been taken by mouth nightly two hours before bed for three months.

For circadian rhythm sleep disorders in people with and without vision problems, melatonin has been taken by mouth as a single dose of 0.5-5 milligrams before bed or as a daily dose for 1-3 months.

For delayed sleep phase syndrome, melatonin has been taken by mouth in doses of 0.3-6 milligrams, with five milligrams being most common, daily before sleeping for two weeks to three months.

For delirium, 0.5 milligrams of melatonin has been taken by mouth nightly for up to 14 days.

For depression, six milligrams of slow-release melatonin has been taken by mouth at bedtime for four weeks.

For exercise performance, 5-6 milligrams of melatonin has been taken by mouth one hour before exercise or before bedtime.

For fertility, three milligrams of melatonin has been taken by mouth nightly from the third to fifth day of the menstrual cycle until hormone injection (human chorionic gonadotropin, HCG), or on the day of hormone injection.

For fibromyalgia, 3-5 milligrams of melatonin has been taken by mouth nightly for four weeks to 60 days.

For stomach and intestine disorders, 3-10 milligrams of melatonin has been taken by mouth nightly for 2-12 weeks.

For headache, 2-10 milligrams of melatonin has been taken by mouth nightly for 14 days to eight weeks.

For liver inflammation, five milligrams of melatonin has been taken by mouth twice daily for 12 weeks.

For high blood pressure, melatonin has been taken by mouth in doses of 1-5 milligrams either as a single dose during the day or before bedtime, or daily for 1-3 months.

For high cholesterol, five milligrams of melatonin has been taken by mouth daily for two months.

For insomnia in the elderly, melatonin has been taken by mouth in doses of 0.1-5 milligrams at or two hours before bedtime for up to several months, in the form of melatonin-rich night milk or slow-release Circadin®. A dose of 0.5 milligrams has been placed in the cheek for four nights.

For jet lag, 0.1-8 milligrams of melatonin has been taken by mouth on the day of travel (close to target bedtime at destination), then daily for several days, in the form of standard or slow-release melatonin (Circadin®).

For memory, three milligrams of melatonin has been taken by mouth before testing.

For menopause, three milligrams of melatonin has been taken by mouth nightly at bedtime for 3-6 months.

For Parkinson's disease, doses of 3-50 milligrams have been taken by mouth nightly before bed for 2-10 weeks. (High doses of 3-6.6 grams of melatonin have also been taken by mouth daily; however, these doses were used in an older 1972 study and are no longer in use.)

For periodic limb movement disorder, three milligrams of melatonin has been taken by mouth nightly for six weeks.

For REM sleep behavior disorder, 3-12 milligrams of melatonin has been taken by mouth daily for four weeks.

For restless leg syndrome, a single dose of three milligrams of melatonin has been taken by mouth.

For sarcoidosis (chronic widespread inflammation), 20 milligrams of melatonin has been taken by mouth daily for one year, then decreased to 10 milligrams for a second year.

For muscle movement problems in people with schizophrenia, 2-10 milligrams of melatonin has been taken by mouth daily.

For seasonal affective disorder (SAD), two milligrams of sustained-release melatonin has been taken by mouth 1-2 hours nightly for three weeks. A dose of 0.5 milligrams of melatonin has been taken under the tongue for six days.

For seizure disorders, doses of melatonin taken by mouth were 3-10 milligrams daily for 2-4 weeks to three months.

For sleep (general), doses of melatonin taken by mouth were 0.3-10 milligrams.

For sleep disorders in people with behavioral, developmental, or mental disorders, 0.1-10 milligrams of melatonin has been taken by mouth daily for up to one year.

For sleep disturbance in Alzheimer's disease, 1.5-10 milligrams of melatonin has been taken by mouth nightly for 10 days to 35 months, together with light exposure or in the form of capsules.

For sleep disturbance in those with asthma, three milligrams of melatonin has been taken by mouth for four weeks.

For sleep disturbance in those with autism, 0.75-10 milligrams of melatonin has been taken nightly before bedtime for two weeks to six months.

For sleep disturbance in those with COPD, three milligrams of melatonin has been taken by mouth nightly.

For sleep disturbance in those with cystic fibrosis, three milligrams of melatonin has been taken by mouth nightly at bedtime for 21 days.

For sleep disturbance in those with depression, 0.5-10 milligrams of melatonin has been taken by mouth for 3-4 weeks, in addition to regular therapy.

For sleep disturbance in healthy people, 0.1-80 milligrams of melatonin has been taken by mouth, generally nightly before bed for one or several days up to 26 weeks. A dose of 50 milligrams has been injected into the vein.

For sleep disturbance in people undergoing hemodialysis, three milligrams of melatonin has been taken by mouth for six weeks.

For sleep disturbance in hospitalized and medically ill people, 3-5.4 milligrams of melatonin has been taken by mouth nightly.

For sleep disturbance in people with a learning disability, 0.5-9 milligrams of melatonin has been taken by mouth for 32-73 days.

For sleep disturbance in those with Parkinson's disease, 3-50 milligrams of melatonin has been taken by mouth at bedtime for 2-4 weeks.

For sleep disturbance after surgery, five milligrams of melatonin has been taken by mouth for three nights.

For sleep disturbance in people with mental disorders, 2-12 milligrams of melatonin has been taken by mouth daily before resting for up to 12 weeks For sleep disturbance in people with traumatic brain injury, five milligrams of melatonin has been taken by mouth for one month.

For sleep disturbance in people with tuberous sclerosis complex (a genetic disorder causing tumors to grow in brain and other organs), five milligrams of melatonin has been taken 20 minutes before bed for two weeks.

For smoking, 0.3 milligrams of melatonin has been taken by mouth 3.5 hours after nicotine withdrawal.

For surgery, 3-15 milligrams of melatonin has been taken by mouth or placed under the tongue, and 0.05-0.2 milligrams per kilogram has been placed under the tongue, either alone or with other sedatives, typically 90 minutes before surgery or the night before and 90 minutes before surgery.

For anxiety or sedation before surgery, 3-10 milligrams and/or 0.05-0.5 milligrams per kilogram of melatonin have been injected into the vein, either alone or with other sedatives before surgery.

For tardive dyskinesia (uncontrolled, repetitive movements), 2-20 milligrams of melatonin has been taken by mouth for 4-12 weeks.

For low platelets, 20 milligrams of melatonin has been taken by mouth nightly for two months.

For ringing in the ears, three milligrams of melatonin has been taken by mouth daily for up to 80 days.

For ulcers, five milligrams of melatonin has been taken by mouth twice daily for 21 days together with other medications.

For nighttime urination, two milligrams of melatonin has been taken by mouth daily for four weeks.

For work shift sleep disorder, 1.8-10 milligrams of melatonin has been taken by mouth up to three times daily for up to six days before daytime sleep after a night shift.

For skin sun damage, melatonin has been applied to the skin in the form of a gel (20-100 milligrams of melatonin in 70% ethanol, in concentrations of 0.05-0.5% in 0.12 milliliters of gel); 0.6 milligrams per meter squared from 15 minutes before to 240 minutes after sun exposure, alone or with vitamins C and E; five percent melatonin in ethanol, propylene glycol, and water; and 5.85 microliters of solutions containing 1.2-5% melatonin, alone or with vitamins C and E.

Melatonin can impact on circadian rhythm differently depending on the time of day at which it is taken, so that attention is typically given to the timing of melatonin dosing.

In accordance with embodiments of the present invention, suitable amounts of Melatonin will be 0.3-75 mg, preferably 1.0-50 mg, more preferably 1.0-20 mg, more preferably 1.0-10 mg, more preferably 2.0-10 mg per day. Most preferably the dosage amounts will range between 0.3 mg and 5.0 mg, between 1.0 mg and 5.0 mg, or between 3.0 mg and 6.0 mg, with all or part of the dose being administered at night/bedtime. Particularly preferred dosages will be 3.0-6.0 mg nightly, or 10-50 mg nightly in severe cases.

Metformin

Metformin is a pharmaceutical compound initially indicated for diabetes and has the following brand names: Glucophage, Riomet®, Fortamet, Glumetza. Approved dosing regimens for diabetic patients are individually tailored, with maximum recommended daily dosages set at 2550 mg for adults or 2000 mg for pediatric patients. Typically, clinically significant responses are not seen at doses below 1500 mg/day. However, therapy is typically initiated with a lower starting dose (e.g., 500 mg once or twice/day or 85-mg/day), with gradually increasing subsequent doses (e.g., increasing in increments of 500 mg/week or 850 mg/2 weeks)

Metformin modulates the mTOR pathway, which antiproliferative effects during treatment with paclitaxel.

Metformin also functions in reducing cell growth, protein synthesis, MAPK3/1, and P90RSK phosphorylation in response to IGF1 through an AMPK-dependent mechanism in cultured bovine granulosa cells. In addition, Metformin strongly inhibited the proliferation, migration, and MMP-2 and -9 expression of HUVECs, also partially AMPK-dependent. Metformin also inhibits cell proliferation, migration and invasion through reexpression of miRNAs and decreased expression of CSC-specific genes, which suggests that Metformin could be useful for overcoming therapeutic resistance of cancer cells, including, for example, pancreatic cancer cells or cells of other epithelial cell cancers.

The present invention recognizes at least two main lines of evidence that suggest that Metformin's primary target is the immortalizing step during tumorigenesis. First, Metformin activates intracellular DNA damage response checkpoints. Second, Metformin attenuates the anti-senescence effects of the ATP-generating glycolytic metabotype, i.e., the Warburg effect, which is required for self-renewal and proliferation of CSCs. If Metformin therapy presents an intrinsic barrier against tumorigenesis by lowering the threshold for stress-induced senescence, then the present invention teaches that Metformin therapeutic strategies may be pivotal for therapeutic intervention for cancer.

Sources of Metformin include Metformin hydrochloride, which is a derivative of metformin present in Riomet (brand name analogs Apo-Metformin, Fortamet, Gen-Metformin, Glucophage, Glucophage XR, Glycon, Metformin HCL, Novo-Metformin, Nu-Metformin) Brand names of combination products include Actoplus Met (Metformin and pioglitazone), Avandamet (Metformin and rosiglitazone), Glucovance (Metformin and Glyburide), Janumet (Metformin and sitagliptin), Kombiglyze (Metformin and saxagliptin), Metaglip (Metformin and Glipizide), PrandiMet (Metformin and repaglinide), all of which have different clinical implications.

Low doses of Metformin have shown multiple pathway effects against cancer. Among its most important potential roles in cancer therapy is Metformin's capacity to improve insulin sensitivity, which results in a reduction in insulin levels and a marked reduction in the quantity and activity of Insulin Growth Factor-1 (IGF-1), which is a critical driver of malignant growth in pancreatic cancer. (Bao, et al., *Biochem Biophys Acta.*, Epub (2010)) Researchers from UCLA have identified cross-talk between insulin/IGF-1 and GPCR signaling systems as a key to pancreatic cancer growth, and since Metformin has been shown to block this cross-talk, they propose Metformin as a promising candidate for pancreatic cancer prevention and treatment. Rozengurt, et al., *Clin Cancer Res.,* 16(9):2505-11 (2010). There is also evidence that Metformin assists in a shift from aerobic glycolysis (the "Warburg Effect") to glucose oxidation, which results in restoration of normal mitochondrial function that, in turn, triggers a renewed capacity for undergoing apoptosis. Martinez-Outschoorn, et al., *Cell Cycle,* 9(16): 3256-76 (2010).

In embodiments of the present invention, a Metformin dosage regimen will be designed by the attending physician to address the particular metabolic pathways implicated in the disease, for the particular patient, bearing in mind, of course, that in selecting the appropriate dosage in any specific case, consideration must be given to the patient's weight, general health, age, and other factors which may influence response to the drug. In general, in a composition according to the invention for treating cancers of epithelial origin cancer, the dosage range will be 50-2000 mg/day, preferably 500-1000 mg/day. Alternatively, doses of 100 mg, 250 mg, 500 mg, 625 mg, 750 mg, 850 mg, or 1000 mg from one to four times a day, or similar dosing regimens, may be administered.

N-Acetyl Cysteine

The active ingredient N-Acetyl Cysteine (NAC) is derived from the amino acid L-cystein. It is a more stable form of Cysteine that can be taken as a supplement. Cysteine is an essential amino acid required for the production of glutathione, a free radical fighter.

NAC is also referred to as: Acetyl Cysteine, Acétyl Cystéine, Acetylcysteine, Acétylcystéine, Chlorhydrate de Cystéine, Cysteine, Cystéine, Cysteine Hydrochloride, Cystine, Hydrochlorure de Cystéine, L-Cysteine, L-Cystéine, L-Cysteine HCl, L-Cystéine HCl, NAC, N-Acetil Cisteína, N-Acetyl-B-Cysteine, N-Acétyl Cystéine, N-Acetyl-L-Cysteine, N-Acétyl-L-Cystéine, N-Acetylcysteine, and N-Acétylcystéine.

NAC has been associated with diminished oxidative stress reflected in preserved antioxidant levels and lower inflammation reflected in lower interleukin levels. NAC is also effective to maintain Vitamins C and E in their reduced state, enhancing their effectiveness which in turn makes the produced glutathione more effective. It is also known to prevent apoptosis through inverse regulation of NFκB and JNK pathways and inducing differentiation of the cells. By suppressing the NF-kappa B pathway, it also represents an attractive therapeutic target for treatments to control neutrophilic inflammation. Treatment of certain carcinomas with NAC monitors expression of the COX-2 protein, inducing apoptosis. It is predicted that this could be effective as a predictor of chemoresistance and that assessment of the COX-2 status could be advantageous to identify cervical cancer patients who may benefit from NAC administration. NAC has also been shown to inhibit both COX-2 expression and NF-kappaB nuclear translocation, which in turn is suggestive that NAC could inhibit the inflammatory process.

NAC is most beneficial (bioavailable) when administered in liposomal form. It is important to use pharmaceutical grade NAC (e.g. Swanson Ultra Pharmaceutical Grade Ajupure® N-Acetyl L-Cysteine).

As an alternative or in addition to NAC, some studies suggest that garlic, selenium, alpha-lipoic acid, and/or L-cysteine can also boost cellular levels of Glutathione, although not as effectively. Life Extension produces a supplement that is comprised of Glutathione, Cysteine and Vitamin C. Glutathione molecules are large and can have trouble crossing the intestinal system to reach the blood stream. However, there are "Glutathione precursors" that are more easily absorbed. Foods known to be rich in Glutathione include vegetables and fruits such as spinach, broccoli, brussels sprouts, parsley, avocado, asparagus, grapefruit, strawberries, milk thistle, whey protein, etc. In addition, there are "Ultimate Antioxidants" that contain NAC and other important antioxidants, but do not reach the quality or bioavailability of these supplements' potential (e.g. Natural Factors® Ultimate Antioxidant contains 100 mg unspecified NAC as well as 13 other ingredients). Milk Thistle, another supplement beneficial to liver health, functions under different mechanisms. (See Milk Thistle supplement above for additional information).

NAC can prove very desirable and/or effective when there is pulmonary involvement.

Naltrexone

Naltrexone hydrochloride is an opioid receptor antagonist that is prescribed as a treatment to reduce the pleasurable effects of alcohol and opioid drugs, thereby reducing cravings. It also has implications in cancer treatment.

Blockage of Opioid Growth Factor (OGF) and OGFr with the nonselective opioid receptor antagonist naltrexone has been shown to upregulate the expression of OGF and OGFr. Administration of a low dosage of naltrexone (LDN) has been shown to block endogenous opioids from opioid receptors for a short period of time. The mechanism of action in cancer targets and inhibits tumor cell proliferation and angiogenesis. LDN has a stimulatory effect on immune cells via an indirect interaction with their opiate receptors, whereas high-dose naltrexone has an inhibitory effect.

Naltrexone is the active ingredient found in name brands including Depade, Vivitrol, and ReVia. Naltrexone is most preferably available in pill form in ReVia (formerly called Trexan). Vivitrol is administered intramuscularly once a month.

Approved dosing regimens for naltrexone include:

TABLE 11

Exemplary Approved Dosing Regimens for Naltrexone

| Indication | Route | Dose |
|---|---|---|
| Alcohol or Opiate Dependence | Oral | 50 mg once a day<br>Optionally 25 mg initial dose<br>Optionally 100 mg doses once/week or every other day<br>Optionally 150 mg doses every third day |
| | Imtramulscular (gluteal injection) | 380 mg once a month, alternating buttocks |

It has been demonstrated that low-doses of Naltrexone, given before bedtime, is associated with clinical improvement and some remissions in cancer patients, even among patients on no conventional cancer therapies. Bihari, B., 2009, Low-Dose Naltrexone for Cancer, online publication at: www.lowdosenaltrexone.org/ldn_and_cancer.htm. A series of published cases in the journal *Integrative Cancer Therapies* documented the complete remissions of 4 patients with advanced pancreatic cancer who combined intravenous high doses of the antioxidant Alpha-Lipoic Acid along with daily low-dose oral Naltrexone. Berkson and Berkson, *Integr. Cancer Ther.,* 5(1):83-9 (2006); Berkson, et al., *Integr. Cancer Ther.* 8(4):416-22 (2009), erratum in *Integr. Cancer Ther.,* 9(2):247 (2010).

Suitable amounts of Naltrexone for use in accordance with many embodiments of the present invention will be 0.1-10 mg, preferably 1.0-10 mg, more preferably 1.5-4.5 mg. For the purposes herein, preferred doses are 3.0 mg and 4.5 mg, in some embodiments rapid release. Related compounds such as (S)—N-methylnaltrexone and Nalmefene may also be used in place of Naltrexone, at equivalent Naltrexone dose.

In some embodiments, inclusion and/or dosing of Naltrexone may be reduced or excluded, particularly for patients relying on pain medications with which Naltrexone might or will interfere. Naltrexone can prove very desirable and/or effective in boosting immune system responses, but can decrease efficacy of certain pain medications, sometimes with undesirable effect.

Opioid Growth Factor

Opioid Growth Factor (OGF) [Met(5)]-enkephalin is an endogenous pentapeptide endorphin with antineoplastic and antiangiogenic activities. OGF acts by binding to the opioid growth factor receptor (OGFr), found on certain tumor cells and vascular cells, and inhibiting tumor cell proliferation and angiogenesis. OGF plays a role in cell proliferation during development, cancer, cellular renewal, wound healing, and angiogenesis.

Several signaling pathways are affected by opioids. Growth-promoting effects were found to be mediated through Akt and Erk signaling cascades. Death-promoting effects are initiated by inhibition of nuclear factor-B, increase of Fas expression, p53 stabilization, cytokine and chemokine release, and activation of nitric oxide synthase, p38, and c-Jun-N-terminal kinase. These are mediated by opioid receptor activation and protein-signaling.

Treatment of tumor cells with OGF slows cell replication in a dose-related, noncytotoxic way. Opioid Growth Factor [Met(5)]-enkephalin is tolerated at a maximum dose of 250 µg/kg over a 30-minute intravenous infusion once or twice weekly. Metronomic dosing of 50 µg/kg injected subcutaneously twice daily shows no toxicity. OGF and its receptor OGFr are considered a principal endogenous opioid axis for regulation of cell proliferation.

Unlike chemotherapy, OGF does not directly destroy cancer cells and is not cytotoxic. An alternative to opioid growth factor could be low-dose-naltrexone or other therapies using opioid blocking mechanisms.

In some embodiments, inclusion and/or dosing of OGH may be reduced or excluded, particularly for patients relying on pain medications. OGH can prove very desirable and/or effective in boosting immune system responses, but can decrease efficacy of certain pain medications, sometimes with undesirable effect.

Squalamine

Squalamine, is an antimicrobial agent, also shown to inhibit the growth of blood vessels within solid tumors. Squalamine can be derived from the internal organs of dogfish shark (*Squalus acanthias*), and has been produced synthetically as well. Squalamine's common name is Squalamine lactate. It is also referred to as Aiguillat, Escualamina, Spiny Dogfish Shark, Squalene, Squalène, *Squalus acanthias*, Squalamax™ and Evizon. Squalamine should not be confused with shark cartilage, which is prepared from the cartilage of spiny dogfish sharks, hammerhead sharks and other shark species.

Squalamine has been shown to exhibit antiangiogenic properties, and has been studied as a treatment for cancer, age-related macular degeneration and bacterial infections. Squalamine enhances bacterial and fungicidal effects when used in combination with standard antibiotics. In angiogenic events, Squalamine inhibits multiple growth factors, including VEGF, PDGF, and bFGF. In addition to its anti-angiogenic mechanism, Squalamine also inhibits the sodium-proton antiporter pump system in the cell membrane. By binding to the membrane, it alters the intracellular pH, disrupts angiogenic signaling, and allows for standard of care chemotherapeutic agents to enter and induce apoptosis, thereby enhancing cytotoxicity of such chemotherapeutic drugs. Squalamine has also been shown to decrease blood flow by decreasing the volume of endothelial cells in vascular beds and narrowing vessels. Squalamine blocks several disease pathways including VEGF and MAPK inhibiting angiogenesis, migration, and proliferation.

The primary natural source of Squalamine is in the tissue (not oil) of the liver, gallbladder, spleen, testes, stomach, gills and intestines of primarily the Dogfish shark, and/or the circulating white blood cells of the sea lamprey. Alternatively or additionally, Squalamine has been synthetically engineered. Nu-Gen Nutrition sells Squalamax dietary supplement which is concentrated squalamine. Squalamine does not have high oral bioavailability. Squalamine is available in an intravitrial injectible form, oral supplement, topical eye drops, and nasal spray. The maximum tolerated dose (MTD) recommended has been found to be 300 mg/m2/day.

Squalamine can be obtained both naturally at high concentration through supplements like Squalamax or synthetically through Evizon. Evizon is the first patented synthetic Squalamine supplement. Squalene and Shark Cartilage are not substitutes for Squalamine, although both have been demonstrated to have potential antiviral, antibacterial and antiangiogenic potential.

Chemotherapeutic and/or Non-Chemotherapeutic Approved Drugs

Cyclophosphamide

Cyclophosphamide (CTX) is a synthetic nitrogen mustard alkylating agent used to treat cancers and autoimmune disorders. In the liver it is converted into the active forms, aldophosphamide and phosphoramide mustard, that have chemotherapeutic activity when they bind to DNA and inhibit DNA replication and initiate cell death.

Cyclophosphamide given at the maximum tolerated dose (MTD) increases cytotoxicity and immunosuppression, and mainly targets proliferating tumor cells. Alternatively, lower metronomic dose concentrations administered at regular intervals without rest periods are immunostimulatory, due to a greater toxicity for suppressor T cells than helper T lymphocytes, and because of the stimulation of NK cells. Additionally, metronomic Cyclophosphamide has antiangiogenic properties by inhibiting preferentially the endothelial cell activity of a tumor's growing vasculature.

Administration of metronomic Cyclophosphamide primarily induces expression of the endogenous inhibitor Thrombospondin-1 (TSP-1). TSP-1 contributes to the suppression of tumor growth when treated with metronomic Cyclophosphamide. Tumors that express a high TSP-1 level are more susceptible to tumor suppression with this treatment.

Suppression of the extracellular regulatory kinase 1 and 2 (ERK1/2) and upstream MEK1/2 proteins is a primary function of Cyclophosphamide. This mechanism serves to lower levels of expression and phosphorylations of MEK1/2 and ERK1/2 proteins and inhibit the proliferation of cancer cells. Cyclophosphamide also activates the PI3K/Akt pathway, a survival-promoting intracellular signaling pathway.

Cyclophosphamide is only available by prescription for a metronomic dosage of 50 mg or less. Trade names include Cytoxan, Neosar, Clafen, Endoavan, Procytox, Revimmune, Carlovan, Cicloval, Cycloblastin, Cyclobastine, CYCLOcell, Cyclostin, Cyclostine, Cytophophan, Endoxana, Enduxan, Fosfaseron, Genoxal, Ledoxine, Procytox, and Sendoxan. The chemical structure of Cyclophosphamide is also known as cytophosphane, ciclofosfamida, ciclofosfamide, claphene, cp monohydrate, CPM, cyclophspham, Cyclophosphamid monohydrate, cyclophosphamidum, cyclophosphan, cyclophosphanum, mitoxan, syklofosfamid, zytoxan.

Approved dosing regimens for cyclophosphamide include:

TABLE 12

Exemplary Approved Cycophophamide Dosing

| Indication | Route | Dose |
| --- | --- | --- |
| Malignant Diseases | IV (intermittent therapy) | 40-50 mg/kg (400-1800 mg/m2) Divided over 2-5 days Map be repeated at intervals of 2-4 weeks |
| | IV (continuous daily therapy) | 60-1200 mg/m2/day (1-2.5 mg/mk/day) |
| | PO (intermittent therapy) | 400-1000 mg/m2 Divided over 4-5 days |
| | PO (continuous daily therapy) | 50-100 mg/m2/day; or 1-5 mg/kg/day |
| Nephrotic Syndrome | | 2-3 mg/kg/day for up to 12 weeks when corticosteroids unsuccessful |
| Non-Hodgkin Lymphoma | | 600-1500 mg/m$^2$ IV with other antineoplastics (part of CHOP regimen); dose intensification possible |
| Breast Cancer | | 600 mg/m$^2$ IV with other antineoplastics; dose intensification possible |

In many embodiments of the present invention, Cyclophosphamide is administered according to a metronomic dosing regimen. In certain particular embodiments, such metronomic dosing regimen is or includes doses of 50 mg/day.

Other Agents

Those skilled in the art will appreciate that various of the agents discussed above herein in the section entitled "Nutraceutical and/or Non-Chemotherapeutic Agents" could alternatively or additionally be addressed in the present section treating "Chemotherapeutic and/or Non-Chemotherapeutic Approved Drugs". It will specifically be appreciated that such characterizations are intended for convenience and not limitation.

In particular, those skilled in the art will specifically appreciate that above-discussed agents such as Metformin and/or Naltrexone can reasonably be considered in either the category of nutraceutical compounds or the category of approved drugs.

Monitoring and/or Adjusting Therapy

Components of inventive therapeutic protocols may, in some embodiments, be prescribed on a predetermined individualized program based, for example, on the blood profile of an individual who has been diagnosed with a cancer. After an initial period, such blood test(s) may be repeated and adjustment made to the regimen, both as to the component compounds and their dosing regimens (e.g., timing and/or amount). In some embodiments, inventive combination regimens are specifically blended to address the specific deficiencies detected in the patient's blood and are precisely dosed accordingly based on, for example, the patient's weight, age, sex, and/or severity of the imbalances or deficiencies intended to be addressed by the nutraceutical. One skilled in the art, for example a patient's oncologist or primary care physician, following analysis of, for instance, blood samples from the affected patient, will be able to determine the precise combination of nutraceuticals and the proper dosages of each compound.

Administration

In general, agents included in inventive combination therapies may be administered in any form, preferably as a tablet, powder, or liquid, formulated into a pharmaceutically acceptable carrier or excipient, depending on the condition of the patient. In some embodiments, providing custom tailored dosages eliminates the need for pre-formulated capsules and tablets. Additionally, non-active ingredients well known in the art, such as binders, fillers, coatings, preservatives, coloring agents, flavoring agents and other additives may optionally be formulated with one or more administered agents, or left out completely if there is a risk of negative side effects to the patient such as increased the risk of intestinal inflammation or interference with the absorption of particular compounds.

In some embodiments, one or more agents included in an inventive therapeutic regimen is administered according to a metronomic regimen.

In some embodiments, inventive therapeutic regimens are added to a program of chemotherapy. In some such embodiments, the compositions of the invention supplement the chemotherapeutic action by addressing additional processes and pathways not addressed by chemotherapeutics and on which the cancer cells of the patient could rely for energy, unchecked proliferation, and migration if such processes and pathways were not controlled or normalized. In many embodiments, effectiveness of any suitable chemotherapeutic used for the treatment of cancer, more particularly for the treatment of epithelial cell related cancers cancer will be improved by adding compositions and combination therapies according to the invention.

Cancers

Those of ordinary skill in the art, reading the present disclosure, will appreciate that one of the particular advantages of inventive therapeutic strategies is their broad applicability across a wide range of cancers.

Those of ordinary skill in the art will particularly appreciate that the present disclosure provides methods and/or compositions particularly useful in the treatment of late-stage cancers. For example, in some embodiments, provided methods and/or compositions are utilized to treat Stage II, Stage III, and/or Stage IV cancer. In some embodiments, provided methods and/or compositions are utilized to treat cancer that has metastasized. In some embodiments, provided methods and/or compositions are utilized to treat cancer that has relapsed after treatment with another therapeutic modality. In some embodiments, provided methods and/or compositions are utilized to treat cancer that has relapsed after treatment with a plurality of other therapeutic modalities.

In some embodiments, methods and/or compositions provided in accordance with the present invention are particularly useful in the treatment of solid tumors. In some embodiments, methods and/or compositions provided in accordance with the present invention are particularly useful in the treatment of tumors of epithelial origin.

In some embodiments, methods and/or compositions provided in accordance with the present invention are particularly useful in the treatment of cancers for which no specific approved therapy exists.

In some embodiments, methods and/or compositions provided in accordance with the present invention may be utilized in the treatment of any cancer, including epithelial cell cancers, sarcomas, and/or blood cancers (leukemias or lymphomas), from Stage I to terminal. In some embodiments, methods and/or compositions provided in accordance with the present invention are particularly useful in the treatment of cancer selected from the group consisting of epithelial cell cancers or sarcomas, methods and/or compositions provided in accordance with the present invention are particularly useful in the treatment of epithelial cell cancers.

In some embodiments, methods and/or compositions provided in accordance with the present invention are particularly useful in the treatment of late stage cancers (e.g., Stage II, Stage III, or Stage IV cancers), methods and/or compositions provided in accordance with the present invention are particularly useful in the treatment of terminal cancers.

In some embodiments, methods and/or compositions provided in accordance with the present invention are particularly useful in the treatment of metastasized cancers.

methods and/or compositions provided in accordance with the present invention are particularly useful in the treatment of cancers that have been, are being, and/or will be treated with conventional therapies including for example conventional chemotherapeutic strategies (e.g., therapies that utilize chemotherapeutic agents at or near their maximum tolerated doses, in some embodiments according to dosing cycles with interspersed breaks).

In some embodiments, methods and/or compositions provided in accordance with the present invention are particularly useful in the treatment of cancer selected from the group consisting of breast cancer, lung cancer, ovarian cancer, pancreatic cancer, etc. In some embodiments, methods and/or compositions provided in accordance with the present invention are particularly useful in the treatment of adenocarcinoma. In some embodiments, methods and/or compositions provided in accordance with the present invention are particularly useful in the treatment of leiomyosarcoma.

EXEMPLIFICATION

Example 1: Exemplary Seven-Component Regimen

A particularly preferred supplementary regimen useful, for example, for treatment of cancers of epithelial origin in cancer patients, includes the following combination of agents:

TABLE 13

Exemplary Inventive Therapeutic Protocol

| Agent | Daily Dose |
|---|---|
| Cyclophosphamide | 50 mg |
| Curcumin | 2400 mg (6 × 400 mg) |
| Melatonin | 10 mg |
| Naltrexone | 4.5 mg |
| Metformin | 500 mg |
| Alpha Lipoic Acid | 1200 mg (4 × 300 mg) |
| Genistein (pure) | 8400 mg (6 × 1400 mg) |

While this combination was specifically designed with reference to actual cancer patients and background data, it was realized that the approach of addressing critical pathways and processes, particularly angiogenesis and other metabolic and signaling pathways, that are dysregulated in cancer but may be returned toward normal state by the administration of nutraceutical, chemotherapeutic and/or non-chemotherapeutic combinations, leading to anti-oncogenic effects. This realization has been applied to design a large range of combination therapies that will be effective so long as they address at least a three abnormally activated or dysregulated pathways from among angiogenesis/vasculogenesis, tumor suppression dysregulation, cell cycle arrest (apoptosis disruption and cell proliferation), and metabolic disruption (e.g., Warburg effect, anaerobic glycolysis, oxidative stress). The compositions and method of the present invention are designed to combine a range of agents and/or therapeutic modalities that address at least three endogenous processes (see, for example, as illustrated in FIG. 1).

Example 2: Exemplary Inventive Therapeutic Regimen Including Three Non-Chemotherapeutic Drugs The present Example specifically describes compositions for use in accordance with the present invention that utilize three non-chemotherapeutic drugs. These three in combination, i.e., Metformin, Cyclophosphamide, and Naltrexone, provide a novel composition, in some embodiments particularly useful for treatment of pancreatic cancer. Such composition addresses critical processes in cancer development and thus provides a useful composition for the therapeutic approach to treatment taught herein.

The use of these three drugs in combination for cancer treatment, especially as an adjunct to chemotherapy, is a novel combination providing effects on several of the most important metabolic, intercellular signaling, and intracellular signaling pathways that are dysregulated in cancers of epithelial origin and other cancers. These include, notably, the pro-angiogenic processes, tumor suppression, and Warburg effect/anaerobic glycolysis/oxidative stress. Accordingly, compositions comprising Metformin, cyclophosphamide, and Naltrexone, are a particularly promising embodiment of the present invention.

Example 3: Exemplary Tailored Inventive Therapeutic Regimens

The present Example describes certain particular embodiments of inventive compositions and/or therapeutic regimens.

In particular, the following Tables 1-6 provide a list of nutraceutical compounds and/or non-chemotherapeutic or chemotherapy drugs for use in methods and compositions of the present invention, for example for the treatment of cancers of epithelial origin. Each Table lists compounds useful for particular categories of cancer-affected metabolic pathways, intercellular signaling pathways, or intracellular signaling pathways, and thus a composition of the invention will typically be comprised of a combination of compounds selected from at least the first four tables (Tables 1-4).

In certain embodiments, by conducting a careful analysis of, for example, a blood sample from a patient suffering from pancreatic cancer, a compound or compounds will be chosen from each Table (depending on the results of the blood test) to create a nutraceutical/non-chemotherapeutic/chemotherapeutic drug "cocktail" to administer to the patient. By following the teachings disclosed herein, one skilled in the art, for example a patient's oncologist or primary care physician, will be able to choose the most beneficial combination of compounds as well as the optimal dosage of each. As some compounds are listed in more than one Table herein, it will be understood by one skilled in the art that if for example, curcumin is chosen from Table 2, it will not be chosen from any other table in which it is listed for preparation of a composition according to the present invention.

TABLE 1

| Metronomic chemotherapy |
|---|
| Cyclophosphamide |

TABLE 2

| Naltrexone |
|---|
| Opiod Growth Factor (Met5-enkephalin) |
| Curcumin |
| Melatonin |

TABLE 3

| Metformin |
|---|
| Curcumin |
| Alpha Lipoic Acid |
| Genistein |
| N-Acetyl Cysteine |
| Squalamine |

TABLE 4

| Melatonin |
|---|
| Naltrexone |
| Squalamine |
| Metformin |
| Genistein |

A particularly preferred combination or supplement for the treatment of patients diagnosed with cancer, more particularly for the treatment of epithelial cell related cancers cancer, along with a preferred dosage regimen is set forth in Table 14:

TABLE 14

| Compound | Dosage | Times Per Day | Daily Dose |
|---|---|---|---|
| Curcumin | 400 mg | 6 | 2400 mg |
| Melatonin | 10 mg | 1 | 10 mg |
| Naltrexone | 4.5 mg | 1 | 4.5 mg |
| Metformin | 500 mg | 1 | 500 mg |
| Cyclophosphamide | 50 mg | 1 | 50 mg |
| Alpha Lipoic Acid | 300 mg | 4 | 1200 mg |

Example 4: Exemplary Inventive Four-Component Therapeutic Regimen

The present Example describes a particular four-component composition for use in accordance with the present invention.

Although many variations are of course possible based on the disclosure provided herein, a proposed embodiment of the present invention for use with a chemotherapy treatment regimen for cancer, more particularly for the treatment of epithelial cell related cancers cancer would include:

1) CYCLOPHOSPHAMIDE—50 mg/day
2) METFORMIN—500 mg/day;
3) NALTREXONE—4.5 mg at bedtime;
4) MELATONIN—10 mg/day.

To the foregoing ingredients, one or more nutraceutical compounds may be added for particular effects, in accordance with the present disclosure.

Example 5: Designing Therapeutic Regimens

As described in Example 1, and throughout the present disclosure, the present invention recognizes that a variety of prescription drugs and/or traditional or nutraceutical agents have been developed that can target any of the 4 key hallmark cancer pathways described herein. In accordance with the present invention, well tolerated such agents (e.g., that show a high therapeutic index) are particularly useful for inclusion in combination cancer therapies. Particular consideration is given to agents that, when combined, can and/or do show synergistic interaction within the framework of the pathways discussed herein.

Moreover, in accordance with the present invention, selection of agents for inclusion in inventive therapeutic strategies does not rely solely on prevention data, or data demonstrating decreased risk of developing cancer (since, as discussed herein, the mechanisms involved in cancer development do not necessarily overlap with therapeutically relevant mechanisms important in metastatic tumors).

Still further, in some embodiments, in vitro data generated with non-physiological or therapeutically irrelevant drug concentrations is discounted or ignored in designing inventive combination regimens, unless backed up by efficacy or mechanism-based data generated in in vivo tumor models or clinical trials.

The particular therapy set forth in Example 1 is representative of this approach and has the particular benefits that it:

Targets four key cancer pathways, simultaneously, that are most relevant for invasive and metastatic cancer.

Each pathway is targeted with at least three separate approaches using at least three different compounds (Table 15). Each compound has extensive in vitro, in vivo and, for several, clinical profiles that scientifically support potential for intervention in the targeted pathways. Additionally, each is currently being tested in phase II or III clinical trials in oncology. The design is intended to provide therapeutic synergy in each pathway and across pathways to significantly extend progression-free and overall survival; and.

Utilizes non-toxic doses of each compound, which can be administered orally and chronically, to create a high quality of life during long term therapy. Existing preclinical safety data and extensive clinical experience with all of the compounds suggests the combination will be well-tolerated during chronic treatment of advanced malignancies.

TABLE 15

Well Tolerated Compounds Targeting 4 Key Hallmark Cancer Pathways

| Compound (refs) | Status | Angiogenesis (including stem cells) | Apoptosis | Metabolism and Energetics | Immune Surveillance |
|---|---|---|---|---|---|
| | | Target (Direct or Indirect) | | | |
| Metronomic Cyclophosphamide (25-41, 146-147*) | Rx for MTD dosing Phase III Oncology | Killing of tumor assoc. endothelial cells ↑TSP-1 | | | ↓Treg cells ↓TGF-β ↓IL-10 ↑NK cells ↑Dendritic cells |
| Metformin (55-67, 148*) | Rx Type 2 Diabetes Phase III Onc | ↑AMPK ↓HIF-1α ↓VEGF | ↑AMPK ↓mTOR ↓STAT3 ↓Protein syn | ↑AMPK ↓GLUT1 ↓Hepatic glucose | ↓STAT3 (stimulates immune response) |
| Melatonin (68-94, 149*) | Dietary Supplement Phase III Onc | ↓VEGF ↓HIF-1α | ↓Bcl-2 ↑Bax | ↓TNF-α (Blocks cachexia) | ↑TH1 (stimulates immune response) ↑NK cells |
| Curcumin (95-116, 150-151*) | Dietary Supplement Phase II Oncology | | ↓BCL-2 ↓STAT3 ↓NF-kB ↓Survivin | | ↓STAT3 (stimulates immune response) ↓NF-kB (inhibits inflammatory response) |
| Naltrexone (117-125, 152-153*) | Rx Opiate & Alcohol Abuse Phase II Onc | | | | ↑TH1 (stimulates immune response) |
| Genistein (126-137, 154*) | Dietary Supplement Phase II Onc | Unknown target | ↑Caspase 3 | | ↑CTL ↑NK cells |
| Alpha Lipoic Acid (138-145, 155*) | Dietary Supplement Phase II Onc | | | ↓PDK1 (inhibits Warburg effect) | |

*Referring to clinical trial phase status

By using orally bioavailable and non-toxic compounds simultaneously targeting four key pathways required for survival and growth of tumors, this therapeutic regimen has the potential to significantly extend progression-free and overall survival with a high quality of life.

Example 6: Treatment of Patient with Adenocarcinoma, Lung Primary

The present Example describes treatment of a female patient, age 67, diagnosed with adenocarcinoma, lung primary.

Patient initially presented with severe shortness of breath and difficulty breathing. Nasal spray, cough medicines, antibiotics, and steroids were prescribed for persistent cough, but improvement was not observed. After several weeks of such therapy, patient was admitted to the emergency room (ER) for continued shortness of breath. X-ray and CT scans were performed, and nodules on lungs were detected. Subsequent bronchoscopy and PET scan confirmed presence of cancer in lungs, liver, and bones of lower back. Palpable nodules were also felt on exam, in the neck/shoulder area.

Beginning 1 week after diagnosis, patient was treated with traditional chemotherapy with 5FU, oxiliplatinum, and leucovorin. Specifically, the patient received two, two-day rounds of:

| Agent | Daily Dose |
|---|---|
| 5FU | 3240 mg |
| Oxaliplatinum | 115 mg |
| Leucovorin | 540 mg |

Rounds were administered two weeks apart. Patient also used oxygen daily. CT and PET scans were utilized as diagnostic measurements.

Beginning less than two weeks after diagnosis (i.e., between the two rounds of traditional chemotherapy), patient began receiving the following inventive therapeutic protocol:

| Exemplary Inventive Therapeutic Protocol ||
|---|---|
| Agent | Daily Dose |
| Cyclophosphamide | 50 mg |
| Curcumin | 1200 mg (6 × 400 mg) |
| Melatonin | 10 mg |
| Naltrexone | 4.5 mg, as tolerated |
| Alpha Lipoic Acid | 1200 mg (4 × 300 mg) |
| Genistein (pure) | 8400 mg (6 × 1400 mg) |

Patient also received protein powder to increase caloric intake, as well as vitamin D3 and n-acetylcysteine (NAC). Oxygen was also continued.

After two weeks on this inventive therapeutic protocol, the patient's CT scan after inventive therapy and before second round of chemotherapy showed 50% reduction in lung mets. The patient continued to experience breathing difficulty, however.

Treatment with this inventive therapeutic protocol was terminated after less than one month, when the patient was admitted to the hospital due to extreme difficulty breathing and spitting up mucus with blood. Patient was intubated and placed on a ventilator. Patient was treated with broad-spectrum antibiotics, anti-viral drugs, and morphine. Patient was determined to have infection with cytomegalovirus (CMV). Bronchial fluid cytology shows presence of cancer. Fever persisted. Oxygen saturation was unstable. Patient passed away shortly thereafter.

Example 7: Treatment of Patient with Breast Leiomyosarcoma (LMS)

The present Example describes treatment of a female patient, age 64, diagnosed with breast leiomyosarcoma (LMS), which had previously been mis-diagnosed as benign intraductal papilloma, and then as poorly differentiated sarcoma. The patient resides in a community without access to a sarcoma specialty center or sarcoma surgery.

Prior to initiation of inventive therapy, the patient had undergone a variety of therapeutic procedures, in each case followed by a relapse. For example, she had a breast quadrantectomy, followed by a radical mastectomy and preventative lymph node removal, but relapsed in just a couple of weeks. Tumor was reported to have grown from 1.5 cm to 4 cm in three weeks. She then had surgery to remove the tumor, scar tissue and pectoraliz muscle, followed by 2 months of 32 additional sessions of radiotherapy when second relapse detected. After 6 weeks she underwent her third tumor resection along with adjacent rib and muscle tissue. Bone marrow contained malignant cancer cells. She took approximately one month-long break before initiating inventive therapy.

Patient has received the following inventive therapy protocol:

TABLE 16

| Exemplary Inventive Therapeutic Protocol ||
|---|---|
| Agent | Daily Dose |
| Cyclophosphamide | 50 mg |
| Curcumin | 2400 mg (6 × 400 mg) |
| Melatonin | 10 mg |
| Naltrexone | 4.5 mg |
| Metformin | 500 mg |
| Alpha Lipoic Acid | 1200 mg (4 × 300 mg) |
| Genistein (pure) | 8400 mg (6 × 1400 mg) |

Patient has also regularly been taking Omega3, Nutrilite Daily multivitamin, concentrated *ganoderma* mushroom and other plant extracts including dandelion, *petiveria*, and yellow poui (*tabebuia*). The patient also takes prescription drugs on a daily basis including Metoprolol, Losartan, Hydrochlorothiazide and Amlodipine to treat hypertension and Levothyroxine which is a thyroid hormone. The patient maintains a no-sugar diet.

Once patient was on inventive therapy, tumor growth apparently slowed significantly. Relapse was detected after 145 days, at which point the detected tumor was said to be 3.8 cm×4 cm×5 cm, a similar size to the one that had grown in three weeks on prior therapy.

The patient reports that inventive therapy is well tolerated and has a very positive impact on overall state of health and feeling of well-being despite presence of active disease.

Example 8: Treatment of Patient with Ovarian Cancer of Unidentified Origin

The present Example describes treatment of a female patient, age 63, initially diagnosed 6 years before initiation of inventive therapy, with stage IIIC Ovarian Cancer.

Since initial diagnosis, patient underwent therapeutic procedures including: a complete hysterectomy to remove a large ovarian tumor with colon resection; ureteral stent; intra-abdominal port; chest port; removal of a major bowel obstruction together with six feet of small intestine and one foot of colon; treatment of infected wound sites; removal of the gallbladder; pericardial window thoracotomy; and multiple other surgeries to deal with complications. Patient also required regular use of supplemental oxygen. Still further, patient received nine rounds of chemotherapy (Intraperitoneal chemotherapy, Carbopaltin, Taxol, Gemzar, Lipidox, Taxotere, Avastin, Cytoxin, Doxil, Navelbine), and one cyberknife radiation treatment.

After almost six years of such conventional treatment, the patient was given a life expectancy estimate from her oncologist: 2-4 weeks to live. Patient was discharged from the hospital to hospice care.

Patient was presented for consideration for receipt of inventive therapy. At the time, patient suffered from significant fluid in lungs which was regularly drained every 2-3 days. Shortness of breath continued to require supplemental oxygen. Patient had little appetite, had been consistently losing weight, had been feeling very weak, and was confined to bed most of the day. Patient's CA-125 had been rising steadily for more than three months, almost quadrupling (rising from 559 to 2901) between tests run about 3.5 months prior to initiation of therapy and about 3 weeks post-initiation of therapy. By eight weeks post-initiation of therapy, this trend had reversed; CA-125 was measured at 833.

Patient received the following inventive therapy:

TABLE 17

Exemplary Inventive Therapeutic Protocol

| Agent | Daily Dose |
|---|---|
| Cyclophosphamide | 50 mg |
| Curcumin | Occasional low doses (given bowel damage, absorption of curcumin was a particular challenge for this patient) |
| Melatonin | 10 mg |
| Naltrexone | Occasional 2.25 mg doses (patient was on pain meds and naltrexone, though useful to boost the immune system, can decrease effectiveness of some such meds, so half doses were utilized, and only occasionally) |
| Metformin | 500 mg |
| Alpha Lipoic Acid | 1200 mg (4 × 300 mg) |
| Genistein (pure) | 8400 mg (6 × 1400 mg) |

During the first three weeks on the inventive therapeutic protocol, the patient continued to lose weight (98 to 85 lbs). Protein powders were used to try to increase caloric intake. During this period, patient also took dichloroacetate (DCA), resveratrol, vitamin D3, L-glutamine, magnesium oil, and pain/anti-nausea medications as needed, including Zofran, Vicodin, Oxytocin, Delaudid, and Ativan.

After 3 weeks on the inventive therapeutic protocol, the patient's use of supplemental oxygen was significantly reduced, her abdominal distension resolved, her appetite increased, and her weight began to increase toward 92 pounds. As noted above, after about 8 weeks on the inventive therapeutic protofol, CA-125 had dropped to 833. The patient's husband reported that despite some nausea and back pain caused by the lung drains, the patient also had increased appetite and increased energy.

The patient stopped taking the inventive therapy after three months. Two weeks later, her CA-125 measured 3432. She passed away three weeks after that measurement.

Although the patient ultimately terminated the therapy and then lost her battle with cancer, she had lived approximately 16-18 weeks longer than her oncologist and hospice nurse predicted.

Example 9: Treatment of Patient with Advanced Stage IV Leiomyosarcoma Including Multiple Metastases The present Example describes use of an inventive therapeutic protocol in the treatment of a female patient, age 46, diagnosed with retroperitenial leiomyosarcoma with metastases to lungs, liver and spine.

At the time of presentation, patient had only 1 kidney working at 78% because a tumor is pressing against her other kidney's ureter. Patient had not received any chemotherapy, surgery or radiation prior to initiation of inventive therapy. In fact, given location of tumors and extent of disease, patient was not considered to be a candidate for surgery.

Beginning 4 months after diagnosis the patient received the following inventive therapeutic protocol:

TABLE 18

Exemplary Inventive Therapeutic Protocol

| Agent | Daily Dose |
|---|---|
| Cyclophosphamide | 50 mg |
| Curcumin | 2400 mg (6 × 400 mg) |
| Melatonin | 10 mg |
| Naltrexone | 4.5 mg |
| Metformin | 500 mg |
| Alpha Lipoic Acid | 1200 mg (4 × 300 mg) |
| Genistein (pure) | 8400 mg (6 × 1400 mg) |

In addition, the patient regularly took Vitamin D3, Beta Glucanase, Organic Coffee Enema, DHA, DCA, Digestase, Peptidase enzymes, serratiopeptidase enzymes, Hemicaellulase enzymes, Glucoamylase enzymes, Apha Galactosidase enzymes, liver-ND, milk thistle, Thiamin, Riboflavin, Vitamin B6 and B12, Folate, Biotin, Pantothenic Acid, PABA, Inositol, Modified Citrus Pectin, elderberry fruit, fermented soy, *magnolia* bark, red clover, mistletoe, *moringa oliefera*, and medicinal mushrooms including reishi mushrooms, chaga mushrooms, *coriolus* mushrooms, maitake mushrooms and *cordyceps* mushrooms. Also, the patient took various prescription drugs as needed, including: Dilaudid, Dolophine and Hydrocodone for pain, Dexamethasone for inflammation, Klonopin for anxiety and Remeron for sleep.

While receiving inventive therapy, the patient maintained a diet with no gluten, no meat, no dairy, and no sugar; she consumed only whole foods and juices as much as possible.

For the first 2-3 weeks of inventive therapy, patient continued to feel significant pain, particularly in the spine, as would be expected for dying tumors. After seven weeks on inventive therapy, spine pain was significantly reduced; some pain remained, though diminished, on the right side, under the rib case, where significant disease is known to exist.

Patient has reported more energy, better appetite, and brighter outlook notwithstanding terminal prognosis delivered by oncologist. Patient specifically reports that overall feeling and outlook while on inventive therapy changed from a feeling of decline and despair to one of quality of life and strong desire to live. Within the seventh week on inventive therapy, the patient reported that she has not felt this well since before her diagnosis.

Example 10: Treatment of Patient with Retroperitoneal Leiomyosarcoma

The present Example describes use of an inventive therapeutic protocol in the treatment of a female patient, age 65, who had initially been incorrectly diagnosed with "hematoma of the right psoas" (later determined to be a tumor bleed). A year later, the patient was again misdiagnosed, this time with Meckel's diverticulitis or a cyst. Eventually, patient was correctly diagnosed after surgery. Correct diagnosis was stage 2b Retroperitoneal Leiomyosarcoma (LMS). LMS cells were given a grade 3 diagnosis (high-grade) indicating fast growing and highly likely to spread. Mitotic Index measured 23. The patient had an LMS tumor, measuring 3.5 cm×3 cm×3 cm, that was wrapped around the patient's ureter, was fibrosed to her appendix, her inferior vena cava, and the psoas muscle.

Once properly diagnosed with LMS, patient had been treated with, for example, laparoscopic resection of the primary lesion; 2 cycles chemotherapy (doxorubicin/dacarbazine); chemoembolization of liver lesions; RFA (Radio Frequency Ablation) for the liver and cryoablation. Additionally, since diagnosis, interval scans have confirmed the following conditions: small nodules in the lungs and abdomen; "multiple" new pulmonary nodules detected bilaterally in lungs; additional metastases in the upper area of the back, posterior chest wall, and the right psoas.

Patient's cancer continued to develop, and within three years had progressed to Stage IV metastatic disease with lesions to the liver and lungs. By the time patient was referred for receipt of inventive therapy, more than 4 years after diagnosis, it was clear that her disease was getting more aggressive—four new distinct areas of metastasis approaching centimeter magnitudes had been identified.

Patient received the following inventive therapy:

TABLE 19

Exemplary Inventive Therapeutic Protocol

| Agent | Daily Dose |
|---|---|
| Cyclophosphamide | 50 mg |
| Curcumin | 2400 mg (6 × 400 mg) |
| Melatonin | 10 mg |
| Naltrexone | 4.5 mg |
| Metformin | 500 mg |
| Alpha Lipoic Acid | 1200 mg (4 × 300 mg) |
| Genistein (pure) | 8400 mg (6 × 1400 mg) |

In addition, at various times while receiving inventive therapy, the patient has received Lorazepam, Alprazolam, Effexo, Valacyclovier, Beta1,3D Glucan, Yamoa, Cinnamon, and/or Zometa (monthly infusions for bone strengthening).

Within days on the inventive therapy, the patient reported a feeling of well being. Energy and sleep patterns dramatically improved. Two weeks after beginning the inventive therapy the patient could palpate a bump in the right shoulder which had been identified as one of the new areas of metastasis detected in March. Ultimately, it was excised and determined to be LMS.

By 6 months on inventive therapy, scans indicated that not a single nodule on the chest CT was greater than 1.7 cm in width and no new nodules were detected. The "something" previously detected at the right psoas had remained unchanged since beginning the inventive therapy and there have been no new hepatic lesions.

By 8 months on the NED Therapy the patient's multiple pulmonary nodules and hepatic lesions still remained unchanged in size.

After nine months on the inventive protocol, the patient was diagnosed as diabetic. At the same time, MRI imaging revealed a marrow-filling lesion in the right humerus and widely disseminated disease throughout the musculature and skeleton. The size and nature of the right humerus lesion with crenulated edges is indicative of old disease, as per general consensus of the patient's sarcoma expert, local oncologist, and attending radiologist.

A comparison of CT scans pre- and post-inventive therapy, suggests that no new metastases have developed in the imaged areas since beginning the inventive therapy and the patient's known lesions have been stable. The patient's sarcoma expert has advised that she continue on her "current regimen" (NED Therapy) for her "indolent" disease.

Patient has reported no adverse side effects while on inventive therapy. The patient indicates she has high energy, feels twenty years younger than her age, and describes quality of life as "excellent".

REFERENCES

1. Brock D W. Ethical and value issues in insurance coverage for cancer treatment. Oncologist. 2010; 15 Suppl 1:36-42. PubMed PMID:20237216.
2. Schnipper L E, Meropol N J, Brock D W. Value and cancer care: toward an equitable future. Clin Cancer Res. 2010 Dec. 15; 16(24):6004-8. PubMed PMID:21169254.
3. Vogelstein B, Papadopoulos N, Velculescu V E, Zhou S, Diaz L A Jr, Kinzler K W. Cancer genome landscapes. Science. 2013 Mar. 29; 339(6127):1546-58. PubMed PMID: 23539594.
4. Hanahan D, Weinberg R A. The hallmarks of cancer. Cell. 2000 Jan. 7; 100(1):57-70. Review. PubMed PMID: 10647931.
5. Hanahan D, Weinberg R A. Hallmarks of cancer: the next generation. Cell. 2011 Mar. 4; 144(5):646-74. PubMed PMID:21376230.
6. Adams C P, Brantner V V. Estimating the cost of new drug development: is it really 802 million dollars? Health Aff (Millwood). 2006 March-April; 25(2):420-8. PubMed PMID:16522582.
7. DiMasi J A, Hansen R W, Grabowski H G. The price of innovation: new estimates of drug development costs. J Health Econ. 2003 March; 22(2):151-85. PubMed PMID: 12606142.
8. Humphrey R W, Brockway-Lunardi L M, Bonk D T, Dohoney K M, Doroshow J H, Meech S J, Ratain M J, Topalian S L, Pardoll D M. Opportunities and challenges in the development of experimental drug combinations for cancer. J Natl Cancer Inst. 2011 Aug. 17; 103(16):1222-6. PubMed PMID:21765011.
9. Levinson A D. Cancer therapy reform. Science. 2010 Apr. 9; 328(5975):137. PubMed PMID:20378778.
10. Woodcock J, Griffin J P, Behrman R E. Development of novel combination therapies. N Engl J Med. 2011 Mar. 17; 364(11):985-7. PubMed PMID:21323535.
Woodcock et al N Engl J Med 364(11):985, 2011 Mar. 17, PubMed PMID:21323535.
11. Maitland M L, Hudoba C, Snider K L, Ratain M J. Analysis of the yield of phase II combination therapy trials in medical oncology. Clin Cancer Res. 2010 Nov. 1; 16(21):5296-302. PubMed PMID:20837695.
12. Draft Guidance for Industry Codevelopment of Two or More Unmarketed Investigational Drugs for Use in Combination. U.S. Dept of Health and Human Services, FDA, CDER, 9567dft, December 2010.
13. Cao Y, Arbiser J, D'Amato R J, D'Amore P A, Ingber D E, Kerbel R, Klagsbrun M, Lim S, Moses M A, Zetter B, Dvorak H, Langer R. Forty-year journey of angiogenesis translational research. Sci Transl Med. 2011 Dec. 21; 3(114):114rv3. PubMed PMID: 22190240.

14. Conley S J, Gheordunescu E, Kakarala P, Newman B, Korkaya H, Heath A N, Clouthier S G, Wicha M S. Antiangiogenic agents increase breast cancer stem cells via the generation of tumor hypoxia. Proc Natl Acad Sci USA. 2012 Feb. 21; 109(8):2784-9. PubMed PMID: 22308314.
15. Ebos J M, Kerbel R S. Antiangiogenic therapy: impact on invasion, disease progression, and metastasis. Nat Rev Clin Oncol. 2011 Mar. 1; 8(4):210-21. PubMed PMID: 21364524.
16. Ferrara N, Kerbel R S. Angiogenesis as a therapeutic target. Nature. 2005 Dec. 15; 438(7070):967-74. PubMed PMID: 16355214.
17. Folkman J. Tumor Angiogenesis: therapeutic implications. NEJM. 1971 Nov. 18; 285(21):1182-6. PubMed PMID: 4938153.
18. Folkman J. Fundamental concepts of the angiogenic process. Cur Mol Med. 2003 November; 3(7):646-51. PubMed PMID: 14601638.
19. Folkman J, Kalluri R. Cancer without disease. Nature. 2004 Feb. 26; 427(6977):787. PubMed PMID: 14985739.
20. Folkman J. Angiogenesis Annual Review. Annu Rev Med. 2006; 57:1-18.
21. Folkman J. Angiogenesis in cancer therapy—Endostatin and its mechanisms of action. Exp Cell Res. 2006 Mar. 10; 312(5):594-607. PubMed PMID: 16376330.
22. Folkman J. Angiogenesis: an organizing principle for drug discovery. Nature. 2007
23. Hanahan D, Folkman J. Patterns and emerging mechanisms of the Angiogenic switch during tumorigenesis. Cell. 1996 Aug. 9; 86(3):353-364. PubMed PMID: 8756718.
24. Kerbel R S. Tumor angiogenesis. N Engl J Med. 2008 May 8; 358(19):2039-49. PubMed PMID: 18463380.
25. Awwad M, North R J. Cyclophosphamide (Cy)-facilitated adoptive immunotherapy of a Cy-resistant tumour. Evidence that Cy permits the expression of adoptive T-cell mediated immunity by removing suppressor T cells rather than by reducing tumour burden. Immunology. 1988 September; 65(1):87-92. PubMed PMID:2972604.
26. Bertolini F, Paul S, Mancuso P, Monestiroli S, Gobbi A, Shaked Y, Kerbel R S. Maximum tolerable dose and low-dose metronomic chemotherapy have opposite effects on the mobilization and viability of circulating endothelial progenitor cells. Cancer Res. 2003 Aug. 1; 63(15):4342-6. PubMed PMID:12907602.
27. Bocci G, Francia G, Man S, Lawler J, Kerbel R S. Thrombospondin 1, a mediator of the antiangiogenic effects of low-dose metronomic chemotherapy. Proc Natl Acad Sci USA. 2003 Oct. 28; 100(22):12917-22. Epub 2003 Oct. 15. PubMed PMID:14561896.
28. Boehm T, Folkman J, Browder T, O'Reilly M S. Antiangiogenic therapy of experimental cancer does not induce acquired drug resistance. Nature (Lond). 1997; 390: 404-407. PubMed PMID: 9389480.
29. Browder T, Butterfield C E, Kraling B M, Shi B, Marshall B, O'Reilly M S, Folkman J. Antiangiogenic scheduling of chemotherapy improves efficacy against experimental drug-resistant cancer. Cancer Res. 2000; 60:1878-1886. PubMed PMID: 10766175.
30. Cruz-Munoz W, Man S, Kerbel R S. Effective treatment of advanced human melanoma metastasis in immunodeficient mice using combination metronomic chemotherapy regimens. Clin Cancer Res. 2009 Aug. 1; 15(15): 4867-74. PubMed PMID:19622578.
31. Emmenegger U, Man S, Shaked Y, Francia G, Wong J W, Hicklin D J, Kerbel R S. A comparative analysis of low-dose metronomic cyclophosphamide reveals absent or low-grade toxicity on tissues highly sensitive to the toxic effects of maximum tolerated dose regimens. Cancer Res. 2004 Jun. 1; 64(11):3994-4000. PubMed PMID: 15173013.
32. Emmenegger U, Shaked Y, Man S, Bocci G, Spasojevic I, Francia G, Kouri A, Coke R, Cruz-Munoz W, Ludeman S M, Colvin O M, Kerbel R S. Pharmacodynamic and pharmacokinetic study of chronic low-dose metronomic cyclophosphamide therapy in mice. Mol Cancer Ther. 2007 August; 6(8):2280-9. PubMed PMID:17671082.
33. Ghiringhelli F, Menard C, Puig P E, Ladoire S, Roux S, Martin F, Solary E, Le Cesne A, Zitvogel L, Chauffert B. Metronomic cyclophosphamide regimen selectively depletes CD4+CD25+ regulatory T cells and restores T and NK effector functions in end stage cancer patients. Cancer Immunol Immunother. 2007 May; 56(5):641-8. PubMed PMID:16960692.
34. Hermans I F, Chong T W, Palmowski M J, Harris A L, Cerundolo V. Synergistic effect of metronomic dosing of cyclophosphamide combined with specific antitumor immunotherapy in a murine melanoma model. Cancer Res. 2003 Dec. 1; 63(23):8408-13. PubMed PMID: 14679003.
35. Kerbel R S, Kamen B A. The anti-angiogenic basis of metronomic chemotherapy. Nat Rev Cancer. 2004 June; 4(6):423-36. PubMed PMID:15170445.
36. Loven D, Hasnis E, Bertolini F, Shaked Y. Low-dose metronomic chemotherapy: from past experience to new paradigms in the treatment of cancer. Drug Discov Today. 2013 February; 18(3-4):193-201. PubMed PMID: 22868084.
37. Man S, Bocci G, Francia G, Green S K, Jothy S, Hanahan D, Bohlen P, Hicklin D J, Bergers G, Kerbel R S. Antitumor effects in mice of low-dose (metronomic) cyclophosphamide administered continuously through the chinking water. Cancer Res. 2002 May 15; 62(10):2731-5. PubMed PMID:12019144.
38. Nakahara T, Uchi H, Lesokhin A M, Avogadri F, Rizzuto G A, Hirschhorn-Cymerman D, Panageas K S, Merghoub T, Wolchok J D, Houghton A N. Cyclophosphamide enhances immunity by modulating the balance of dendritic cell subsets in lymphoid organs. Blood. 2010 Jun. 3; 115(22):4384-92. PubMed PMID:20154220.
39. Pasquier E, Kavallaris M, André N. Metronomic chemotherapy: new rationale for new directions. Nat Rev Clin Oncol. 2010 August; 7(8):455-65. PubMed PMID: 20531380.
40. Penel N, Adenis A, Bocci G. Cyclophosphamide-based metronomic chemotherapy: after 10 years of experience, where do we stand and where are we going? Crit Rev Oncol Hematol. 2012 April; 82(1):40-50. PubMed PMID: 21641231.
41. Stoelting S, Trefzer T, Kisro J, Steinke A, Wagner T, Peters S O. Low-dose oral metronomic chemotherapy prevents mobilization of endothelial progenitor cells into the blood of cancer patients. In Vivo. 2008 November-December; 22(6):831-6. PubMed PMID:19181016.
42. Ocker M, Höpfner M. Apoptosis-modulating drugs for improved cancer therapy. Eur Surg Res. 2012; 48(3):111-20. PubMed PMID: 22538523.
43. Wong R S. Apoptosis in cancer: from pathogenesis to treatment. J Exp Clin Cancer Res. 2011 Sep. 26; 30:87. PubMed PMID:21943236.

44. Riether C, Schürch C, Ochsenbein A F. From "magic bullets" to specific cancer immunotherapy. Swiss Med Wkly. 2013 Jan. 23; 143:w13734. PubMed PMID: 23348718.
45. Callahan M K, Postow M A, Wolchok J D. Immunomodulatory therapy for melanoma: ipilimumab and beyond. Clin Dermatol. 2013 March-April; 31(2):191-9. PubMed PMID:23438382.
46. Faubert B, Boily G, Izreig S, Griss T, Samborska B, Dong Z, Dupuy F, Chambers C, Fuerth B J, Viollet B, Mamer O A, Avizonis D, DeBerardinis R J, Siegel P M, Jones R G. AMPK is a negative regulator of the Warburg effect and suppresses tumor growth in vivo. Cell Metab. 2013 Jan. 8; 17(1):113-24. PubMed PMID:23274086.
47. Shackelford D B, Shaw R J. The LKB1-AMPK pathway: metabolism and growth control in tumour suppression. Nat Rev Cancer. 2009 August; 9(8):563-75. PubMed PMID:19629071.
48. Vander Heiden M G, Cantley L C, Thompson C B. Understanding the Warburg effect: the metabolic requirements of cell proliferation. Science. 2009 May 22; 324 (5930):1029-33. PubMed PMID:19460998.
49. Ward P S, Thompson C B. Metabolic reprogramming: a cancer hallmark even warburg did not anticipate. Cancer Cell. 2012 Mar. 20; 21(3):297-308. PubMed PMID: 22439925.
50. Wenger J B, Chun S Y, Dang D T, Luesch H, Dang L H. Combination therapy targeting cancer metabolism. Med Hypotheses. 2011 February; 76(2):169-72. PubMed PMID: 20947261.
51. Yun J, Rago C, Cheong I, Pagliarini R, Angenendt P, Rajagopalan H, Schmidt K, Willson J K, Markowitz S, Zhou S, Diaz L A Jr, Velculescu V E, Lengauer C, Kinzler K W, Vogelstein B, Papadopoulos N. Glucose deprivation contributes to the development of KRAS pathway mutations in tumor cells. Science. 2009 Sep. 18; 325(5947): 1555-9. PubMed PMID:19661383.
52. Gomez-Pinillos A, Ferrari A C. mTOR signaling pathway and mTOR inhibitors in cancer therapy. Hematol Oncol Clin North Am. 2012 June; 26(3):483-505, vii. PubMed PMID:22520976.
53. Shaw R J. LKB1 and AMP-activated protein kinase control of mTOR signalling and growth. Acta Physiol (Oxf). 2009 May; 196(1):65-80. PubMed PMID: 19245654.
54. Zoncu R, Efeyan A, Sabatini D M. mTOR: from growth signal integration to cancer, diabetes and ageing. Nat Rev Mol Cell Biol. 2011 January; 12(1):21-35. PubMed PMID:21157483.
55. Del Barco S, Vazquez-Martin A, Cufi S, Oliveras-Ferraros C, Bosch-Barrera J, Joven J, Martin-Castillo B, Menendez J A. Metformin: multi-faceted protection against cancer. Oncotarget. 2011 December; 2(12):896-917. PubMed PMID:22203527.
56. Deng X S, Wang S, Deng A, Liu B, Edgerton S M, Lind S E, Wandan-Alaswad R, Thor A D. Metformin targets Stat3 to inhibit cell growth and induce apoptosis in triple-negative breast cancers. Cell Cycle. 2012 Jan. 15; 11(2):367-76. PubMed PMID:22189713.
57. Duque J E, Velez J, Samudio I, Lai E. Metformin as a Novel Component of Metronomic Chemotherapeutic Use: A Hypothesis. J Exper & Clin Med. 2012 June 1; 4(3):140-144.
58. Foretz M, Hébrard S, Leclerc J, Zarrinpashneh E, Soty M, Mithieux G, Sakamoto K, Andreelli F, Viollet B. Metformin inhibits hepatic gluconeogenesis in mice independently of the LKB1/AMPK pathway via a decrease in hepatic energy state. J Clin Invest. 2010 July; 120(7): 2355-69. PubMed PMID:20577053.
59. Gwinn D M, Shackelford D B, Egan D F, Mihaylova M M, Mery A, Vasquez D S, Turk B E, Shaw R J. AMPK Phosphorylation of Raptor Mediates a Metabolic Checkpoint. Molecular Cell. 2008 Apr. 25; 30(2):214-226. PubMed PMID:18439900.
60. Jiralerspong S, Palla S L, Giordano S H, Meric-Bernstam F, Liedtke C, Barnett C M, Hsu L, Hung M C, Hortobagyi G N, Gonzalez-Angulo A M. Metformin and pathologic complete responses to neoadjuvant chemotherapy in diabetic patients with breast cancer. J Clin Oncol. 2009 Jul. 10; 27(20):3297-302. PubMed PMID: 19487376.
61. Kalender A, Selvaraj A, Kim S Y, Gulati P, Brûlé S, Viollet B, Kemp B E, Bardeesy N, Dennis P, Schlager J J, Marette A, Kozma S C, Thomas G. Metformin, independent of AMPK, inhibits mTORC1 in a rag GTPase-dependent manner. Cell Metab. 2010 May 5; 11(5):390-401. PubMed PMID:20444419.
62. Kumar S, Meuter A, Thapa P, Langstraat C, Giri S, Chien J, Rattan R, Cliby W, Shridhar V. Metformin Intake is Associated with Better Survival in Ovarian Cancer. Cancer. 2013 Feb. 1; 119(3):555-562. PubMed PMID: 23208739.
63. Larsson O, Morita M, Topisirovic I, Alain T, Blouin M J, Pollak M, Sonenberg N. Distinct perturbation of the translatome by the antidiabetic drug metformin. Proc Natl Acad Sci USA. 2012 Jun. 5; 109(23):8977-82. PubMed PMID:22611195.
64. Lin C C, Yeh H H, Huang W L, Yan J J, Lai W W, Su W P, Chen H H, Su W C. Metformin Enhances Cisplatin Cytotoxicity by Suppressing Stat3 Activity Independently of the LKB1-AMPK Pathway. Am J Respir Cell Mol Biol. 2013 Mar. 22. PubMed PMID:23526220.
65. Miller R A, Birnbaum M J. An energetic tale of AMPK-independent effects of metformin. J Clin Invest. 2010 July; 120(7):2267-70. PubMed PMID:20577046.
66. Shaw R J, Lamia K A, Vasquez D, Koo S H, Bardeesy N, Depinho R A, Montminy M, Cantley L C. The kinase LKB1 mediates glucose homeostasis in liver and therapeutic effects of metformin. Science. 2005 Dec. 9; 310 (5754):1642-6. PubMed PMID:16308421.
67. Subramaniam A, Shanmugam M K, Perumal E, Li F, Nachiyappan A, Dai X, Swamy S N, Ahn K S, Kumar A P, Tan B K, Hui K M, Sethi G. Potential role of signal transducer and activator of transcription (STAT)3 signaling pathway in inflammation, survival, proliferation and invasion of hepatocellular carcinoma. Biochim Biophys Acta. 2013 January; 1835(1):46-60. PubMed PMID: 23103770.
68. Arendt J. Safety of melatonin in long-term use (?) J Biol Rhythms. 1997 December; 12(6):673-81. PubMed PMID: 9406044.
69. Barth S, Lissoni P, Cazzaniga M, Ardizzoia A, Meregalli S, Fossati V, Fumagalli L, Brivio F, Tancini G. A randomized study of low-dose subcutaneous interleukin-2 plus melatonin versus supportive care alone in metastatic colorectal cancer patients progressing under 5-fluorouracil and folates. Oncology. 1995 May-June; 52(3):243-5. PubMed PMID:7715908.
70. Buscemi N, Vandermeer B, Hooton N, Pandya R, Tjosvold L, Hartling L, Baker G, Klassen T P, Vohra S. The efficacy and safety of exogenous melatonin for primary sleep disorders. A meta-analysis. J Gen Intern Med. 2005 December; 20(12):1151-8. PubMed PMID: 16423108.

71. Carrillo-Vico A, Guerrero J M, Lardone P J, Reiter R J. A review of the multiple actions of melatonin on the immune system. Endocrine. 2005 July; 27(2):189-200. Review. PubMed PMID:16217132.
72. Cutando A, López-Valverde A, Arias-Santiago S, D E Vicente J, D E Diego R G. Role of melatonin in cancer treatment. Anticancer Res. 2012 July; 32(7):2747-53. PubMed PMID:22753734.
73. Kane M A, Johnson A, Nash A E, Boose D, Mathai G, Balmer C, Yohn J J, Robinson W A. Serum melatonin levels in melanoma patients after repeated oral administration. Melanoma Res. 1994 February; 4(1):59-65. PubMed PMID:8032220.
74. Kim K J, Choi J S, Kang I, Kim K W, Jeong C H, Jeong J W. Melatonin suppresses tumor progression by reducing angiogenesis stimulated by HIF-1 in a mouse tumor model. J Pineal Res. 2013 April; 54(3):264-70. PubMed PMID:22924616.
75. Lemoine P, Garfinkel D, Laudon M, Nir T, Zisapel N. Prolonged-release melatonin for insomnia—an open-label long-term study of efficacy, safety, and withdrawal. Ther Clin Risk Manag. 2011; 7:301-11. PubMed PMID: 21845053.
76. Lissoni P. Biochemotherapy with standard chemotherapies plus the pineal hormone melatonin in the treatment of advanced solid neoplasms. Pathol Biol (Paris). 2007 April-May; 55(3-4):201-4. PubMed PMID:17446010.
77. Lissoni P, Ardizzoia A, Barni S, Paolorossi F, Tancini G, Meregalli S, Esposti D, Zubelewicz B, Braczowski R. A randomized study of tamoxifen alone versus tamoxifen plus melatonin in estrogen receptor-negative heavily pre-treated metastatic breast-cancer patients. Oncol Rep. 1995 September; 2(5):871-3. PubMed PMID:21597833.
78. Lissoni P, Barni S, Ardizzoia A, Paolorossi F, Crispin S, Tancini G, Tisi E, Archili C, De Toma D, Pipino G, et al. Randomized study with the pineal hormone melatonin versus supportive care alone in advanced nonsmall cell lung cancer resistant to a first-line chemotherapy containing cisplatin. Oncology. 1992; 49(5):336-9. PubMed PMID:1382256.
79. Lissoni P, Barni S, Fossati V, Ardizzoia A, Cazzaniga M, Tancini G, Frigerio F. A randomized study of neuroimmunotherapy with low-dose subcutaneous interleukin-2 plus melatonin compared to supportive care alone in patients with untreatable metastatic solid tumour. Support Care Cancer. 1995 May; 3(3):194-7. PubMed PMID: 7655780.
80. Lissoni P, Barni S, Mandala M, Ardizzoia A, Paolorossi F, Vaghi M, Longarini R, Malugani F, Tancini G. Decreased toxicity and increased efficacy of cancer chemotherapy using the pineal hormone melatonin in metastatic solid tumour patients with poor clinical status. Eur J Cancer. 1999 November; 35(12):1688-92. PubMed PMID:10674014.
81. Lissoni P, Barni S, Tancini G, Ardizzoia A, Ricci G, Aldeghi R, Brivio F, Tisi E, Rovelli F, Rescaldani R, et al. A randomised study with subcutaneous low-dose interleukin 2 alone vs interleukin 2 plus the pineal neurohormone melatonin in advanced solid neoplasms other than renal cancer and melanoma. Br J Cancer. 1994 January; 69(1):196-9. PubMed PMID:8286206.
82. Lissoni P, Brivio F, Fumagalli L, Messina G, Vigoré L, Parolini D, Colciago M, Rovelli F. Neuroimmunomodulation in medical oncology: application of psychoneuroimmunology with subcutaneous low-dose IL-2 and the pineal hormone melatonin in patients with untreatable metastatic solid tumors. Anticancer Res. 2008 March-April; 28(2B):1377-81. PubMed PMID:18505083.
83. Lissoni P, Chilelli M, Villa S, Cerizza L, Tancini G. Five years survival in metastatic non-small cell lung cancer patients treated with chemotherapy alone or chemotherapy and melatonin: a randomized trial. J Pineal Res. 2003 August; 35(1):12-5. PubMed PMID:12823608.
84. Lissoni P, Malugani F, Malysheva O, Kozlov V, Laudon M, Conti A, Maestroni G. Neuroimmunotherapy of untreatable metastatic solid tumors with subcutaneous low-dose interleukin-2, melatonin and naltrexone: modulation of interleukin-2-induced antitumor immunity by blocking the opioid system. Neuro Endocrinol Lett. 2002 August; 23(4):341-4. PubMed PMID:12195238.
85. Lissoni P, Paolorossi F, Ardizzoia A, Barni S, Chilelli M, Mancuso M, Tancini G, Conti A, Maestroni G J. A randomized study of chemotherapy with cisplatin plus etoposide versus chemoendocrine therapy with cisplatin, etoposide and the pineal hormone melatonin as a first-line treatment of advanced non-small cell lung cancer patients in a poor clinical state. J Pineal Res. 1997 August; 23(1):15-9. PubMed PMID:9379341.
86. Lissoni P, Paolorossi F, Tancini G, Barni S, Ardizzoia A, Brivio F, Zubelewicz B, Chatikhine V. Is there a role for melatonin in the treatment of neoplastic cachexia? Eur J Cancer. 1996 July; 32A(8):1340-3. PubMed PMID: 8869096.
87. Lissoni P, Rovelli F. Principles of psychoneuroendocrinoimmunotherapy of cancer. Immunotherapy. 2012 January; 4(1):77-86. PubMed PMID:22150002.
88. Lv D, Cui P L, Yao S W, Xu Y Q, Yang Z X. Melatonin inhibits the expression of vascular endothelial growth factor in pancreatic cancer cells. Chin J Cancer Res. 2012 December; 24(4):310-6. PubMed PMID:23358453.
89. Mediavilla M D, Sanchez-Barcelo E J, Tan D X, Manchester L, Reiter R J. Basic mechanisms involved in the anti-cancer effects of melatonin. Curr Med Chem. 2010; 17(36):4462-81. PubMed PMID:21062257.
90. Rodriguez C, Martín V, Herrera F, García-Santos G, Rodriguez-Blanco J, Casado-Zapico S, Sánchez-Sánchez A M, Suárez S, Puente-Moncada N, Anitua M J, Antolín I. Mechanisms involved in the pro-apoptotic effect of melatonin in cancer cells. Int J Mol Sci. 2013 Mar. 25; 14(4):6597-613. PubMed PMID:23528889.
91. Sánchez-Barceló E J, Mediavilla M D, Tan D X, Reiter R J. Clinical uses of melatonin: evaluation of human trials. Curr Med Chem. 2010; 17(19):2070-95. Review. PubMed PMID:20423309.
92. Seely D, Wu P, Fritz H, Kennedy D A, Tsui T, Seely A J, Mills E. Melatonin as adjuvant cancer care with and without chemotherapy: a systematic review and meta-analysis of randomized trials. Integr Cancer Ther. 2012 December; 11(4):293-303. PubMed PMID:22019490.
93. Wang Y M, Jin B Z, Ai F, Duan C H, Lu Y Z, Dong T F, Fu Q L. The efficacy and safety of melatonin in concurrent chemotherapy or radiotherapy for solid tumors: a meta-analysis of randomized controlled trials. Cancer Chemother Pharmacol. 2012 May; 69(5):1213-20. PubMed PMID:22271210.
94. Xu C, Wu A, Zhu H, Fang H, Xu L, Ye J, Shen J. Melatonin is involved in the apoptosis and necrosis of pancreatic cancer cell line SW-1990 via modulating of Bcl-2/Bax balance. Biomed Pharmacother. 2013 March; 67(2):133-9. PubMed PMID:23245210.

95. Aggarwal B B, Gupta S C, Sung B. Curcumin: An Orally Bioavailable Blocker of TNF and Other Pro-inflammatory Biomarkers. Br J Pharmacol. 2013 Feb. 20. PubMed PMID:23425071.

96. Bayet-Robert M, Kwiatkowski F, Leheurteur M, Gachon F, Planchat E, Abrial C, Mouret-Reynier M A, Durando X, Barthomeuf C, Chollet P. Phase I dose escalation trial of docetaxel plus curcumin in patients with advanced and metastatic breast cancer. Cancer Biol Ther. 2010 January; 9(1):8-14. PubMed PMID:19901561.

97. Belcaro G, Cesarone M R, Dugall M, Pellegrini L, Ledda A, Grossi M G, Togni S, Appendino G. Efficacy and safety of Meriva®, a curcumin-phosphatidylcholine complex, during extended administration in osteoarthritis patients. Altern Med Rev. 2010 December; 15(4):337-44. PubMed PMID:21194249.

98. Cuomo J, Appendino G, Dern A S, Schneider E, McKinnon T P, Brown M J, Togni S, Dixon B M. Comparative absorption of a standardized curcuminoid mixture and its lecithin formulation. J Nat Prod. 2011 Apr. 25; 74(4):664-9. PubMed PMID:21413691.

99. Dhillon N, Aggarwal B B, Newman R A, Wolff R A, Kunnumakkara A B, Abbruzzese J L, Ng C S, Badmaev V, Kurzrock R. Phase II trial of curcumin in patients with advanced pancreatic cancer. Clin Cancer Res. 2008 Jul. 15; 14(14):4491-9. PubMed PMID:18628464.

100. Finney L, Mandava S, Ursos L, Zhang W, Rodi D, Vogt S, Legnin D, Maser J, Ikpatt F, Olopade O I, Glesne D. X-ray fluorescence microscopy reveals large-scale relocalization and extracellular translocation of cellular copper during angiogenesis. Natl Acad Sci USA. 2007 Feb. 13; 104(7):2247-52. Epub 2007 Feb. 5. PubMed PMID: 17283338.

101. Glienke W, Maute L, Wicht J, Bergmann L. Curcumin inhibits constitutive STAT3 phosphorylation in human pancreatic cancer cell lines and downregulation of survivin/BIRC5 gene expression. Cancer Invest. 2010 February; 28(2):166-71. PubMed PMID:20121547.

102. Gupta S C, Kismali G, Aggarwal B B. Curcumin, a component of turmeric: from farm to pharmacy. Biofactors. 2013 January-February; 39(1):2-13. PubMed PMID: 23339055.

103. Gupta S C, Patchva S, Aggarwal B B. Therapeutic roles of curcumin: lessons learned from clinical trials. AAPS J. 2013 January; 15(1):195-218. PubMed PMID:23143785.

104. Hasima N, Aggarwal B B. Cancer-linked targets modulated by curcumin. Int J Biochem Mol Biol. 2012; 3(4): 328-51. PubMed PMID:23301199.

105. Hung C S, Liu H H, Huang M T, Cheng C W, Kuo L J, Ho Y S, Wu C H, Chen C M, Wei P L, Chang Y J. Knockdown survivin expression reduces the efficacy of curcumin treatment in hepatocellular carcinoma cells. Ann Surg Oncol. 2012 October; 19(11):3547-55. PubMed PMID:22711176.

106. Kanai M, Otsuka Y, Otsuka K, Sato M, Nishimura T, Mori Y, Kawaguchi M, Hatano E, Kodama Y, Matsumoto S, Murakami Y, Imaizumi A, Chiba T, Nishihira J, Shibata H. A phase I study investigating the safety and pharmacokinetics of highly bioavailable curcumin (Theracurmin (®)) in cancer patients. Cancer Chemother Pharmacol. 2013 Mar. 30. PubMed PMID:23543271.

107. Kanai M, Yoshimura K, Asada M, Imaizumi A, Suzuki C, Matsumoto S, Nishimura T, Mori Y, Masui T, Kawaguchi Y, Yanagihara K, Yazumi S, Chiba T, Guha S, Aggarwal B B. A phase I/II study of gemcitabine-based chemotherapy plus curcumin for patients with gemcitabine-resistant pancreatic cancer. Cancer Chemother Pharmacol. 2011 July; 68(1):157-64. PubMed PMID: 20859741.

108. Mackenzie G G, Queisser N, Wolfson M L, Fraga C G, Adamo A M, Oteiza P I. Curcumin induces cell-arrest and apoptosis in association with the inhibition of constitutively active NF-kappaB and STAT3 pathways in Hodgkin's lymphoma cells. Int J Cancer. 2008 Jul. 1; 123(1): 56-65. PubMed PMID:18386790.

109. Marczylo T H, Verschoyle R D, Cooke D N, Morazzoni P, Steward W P, Gescher A J. Comparison of systemic availability of curcumin with that of curcumin formulated with phosphatidylcholine. Cancer Chemother Pharmacol. 2007 July; 60(2):171-7. PubMed PMID:17051370.

110. Marín Y E, Wall B A, Wang S, Namkoong J, Martino J J, Suh J, Lee H J, Rabson A B, Yang C S, Chen S, Ryu J H. Curcumin downregulates the constitutive activity of NF-kappaB and induces apoptosis in novel mouse melanoma cells. Melanoma Res. 2007 October; 17(5):274-83. PubMed PMID:17885582.

111. Saydmohammed M, Joseph D, Syed V. Curcumin suppresses constitutive activation of STAT-3 by up-regulating protein inhibitor of activated STAT-3 (PIAS-3) in ovarian and endometrial cancer cells. J Cell Biochem. 2010 May 15; 110(2):447-56. PubMed PMID:20235152.

112. Sharma R A, Euden S A, Platton S L, Cooke D N, Shafayat A, Hewitt H R, Marczylo T H, Morgan B, Hemingway D, Plummer S M, Pirmohamed M, Gescher A J, Steward W P. Phase I clinical trial of oral curcumin: biomarkers of systemic activity and compliance. Clin Cancer Res. 2004 Oct. 15; 10(20):6847-54. PubMed PMID:15501961.

113. Su C C, Yang J S, Lu C C, Chiang J H, Wu C L, Lin J J, Lai K C, Hsia T C, Lu H F, Fan M J, Chung J G. Curcumin inhibits human lung large cell carcinoma cancer tumour growth in a murine xenograft model. Phytother Res. 2010 February; 24(2):189-92. PubMed PMID: 20077433.

114. Watson J L, Greenshields A, Hill R, Hilchie A, Lee P W, Giacomantonio C A, Hoskin D W. Curcumin-induced apoptosis in ovarian carcinoma cells is p53-independent and involves p38 mitogen-activated protein kinase activation and downregulation of Bcl-2 and survivin expression and Akt signaling. Mol Carcinog. 2010 January; 49(1):13-24. PubMed PMID:19676105.

115. Wu B, Yao H, Wang S, Xu R. DAPK1 modulates a curcumin-induced G2/M arrest and apoptosis by regulating STAT3, NF-κB, and caspase-3 activation. Biochem Biophys Res Commun 2013 Apr. 26; 434(1):75-80. PubMed PMID:23545262.

116. Zhang C, Li B, Zhang X, Hazarika P, Aggarwal B B, Duvic M. Curcumin selectively induces apoptosis in cutaneous T-cell lymphoma cell lines and patients' PBMCs: potential role for STAT-3 and NF-kappaB signaling. J Invest Dermatol. 2010 August; 130(8):2110-9. PubMed PMID:20393484.

117. Agrawal Y P. Low dose naltrexone therapy in multiple sclerosis. Med Hypotheses. 2005; 64(4):721-4. PubMed PMID:15694688.

118. Lissoni P, Malugani F, Bordin V, Conti A, Maestroni G, Tancini G. A new neuroimmunotherapeutic strategy of subcutaneous low-dose interleukin-2 plus the long-acting opioid antagonist naltrexone in metastatic cancer patients progressing on interleukin-2 alone. Neuro Endocrinol Lett. 2002 June; 23(3):255-8. PubMed PMID:12080288.

119. Lissoni P, Malugani F, Malysheva O, Kozlov V, Laudon M, Conti A, Maestroni G. Neuroimmunotherapy of 119. untreatable metastatic solid tumors with subcutaneous low-dose interleukin-2, melatonin and naltrexone: modulation of interleukin-2-induced antitumor immunity by blocking the opioid system. Neuro Endocrinol Lett. 2002 August; 23(4):341-4. PubMed PMID:12195238.
120. Lissoni P, Rovelli F. Principles of psychoneuroendocrinoimmunotherapy of cancer. Immunotherapy. 2012 January; 4(1):77-86. PubMed PMID:22150002.
121. Marrazzi M A, Wroblewski J M, Kinzie J, Luby E D. High-dose naltrexone and liver function safety. Am J Addict. 1997 Winter; 6(1):21-9. PubMed PMID:9097868.
122. Smith J P, Field D, Bingaman S I, Evans R, Mauger D T. Safety and tolerability of low-dose naltrexone therapy in children with moderate to severe Crohn's disease: a pilot study. J Clin Gastroenterol. 2013 April; 47(4):339-45. PubMed PMID:23188075.
123. Smith J P, Stock H, Bingaman S, Mauger D, Rogosnitzky M, Zagon I S. Low-dose naltrexone therapy improves active Crohn's disease. Am J Gastroenterol. 2007 April; 102(4):820-8. PubMed PMID:17222320.
124. Yoon G, Kim S W, Thuras P, Westermeyer J. Safety, tolerability, and feasibility of high-dose naltrexone in alcohol dependence: an open-label study. Hum Psychopharmacol. 2011 March; 26(2):125-32. PubMed PMID: 21437991.
125. Younger J, Noor N, McCue R, Mackey S. Low-dose naltrexone for the treatment of fibromyalgia: findings of a small, randomized, double-blind, placebo controlled, counterbalanced, crossover trial assessing daily pain levels. Arthritis Rheum. 2013 February; 65(2):529-38. PubMed PMID:23359310.
126. Büchler P, Gukovskaya A S, Mouria M, Buchler M C, Büchler M W, Friess H, Pandol S J, Reber H A, Hines O J. Prevention of Metastatic Pancreatic Cancer Growth in vivo by Induction of Apoptosis with Genistein, a Naturally Occurring Isoflavanoid. Pancreas. 2003 April; 26(3): 264-73. PubMed PMID:12657953.
127. Guo T L, McCay J A, Zhang L X, Brown R D, You L, Karrow N A, Germolec D R, White K L Jr. Genistein modulates immune responses and increases host resistance to B16F10 tumor in adult female B6C3F1 mice. J Nutr. 2001 December; 131(12):3251-8. PubMed PMID: 11739876.
128. Lakshman M, Xu L, Ananthanarayanan V, Cooper J, Takimoto C H, Helenowski I, Pelling J C, Bergan R C. Dietary genistein inhibits metastasis of human prostate cancer in mice. Cancer Res. 2008 Mar. 15; 68(6):2024-32. PubMed PMID:18339885.
129. Lazarevic B, Boezelijn G, Diep L M, Kvernrod K, Ogren O, Ramberg H, Moen A, Wessel N, Berg R E, Egge-Jacobsen W, Hammarstrom C, Svindland A, Kucuk O, Saatcioglu F, Tasken K A, Karlsen S J. Efficacy and safety of short-term genistein intervention in patients with localized prostate cancer prior to radical prostatectomy: a randomized, placebo-controlled, double-blind Phase 2 clinical trial. Nutr Cancer. 2011; 63(6):889-98. PubMed PMID:21714686.
130. Marini H, Bitto A, Altavilla D, Burnett B P, Polito F, Di Stefano V, Minutoli L, Atteritano M, Levy R M, D'Anna R, Frisina N, Mazzaferro S, Cancellieri F, Cannata M L, Corrado F, Frisina A, Adamo V, Lubrano C, Sansotta C, Marini R, Adamo E B, Squadrito F. Breast safety and efficacy of genistein aglycone for postmenopausal bone loss: a follow-up study. J Clin Endocrinol Metab. 2008 December; 93(12):4787-96. PubMed PMID:18796517.
131. McClain M R, Wolz E, Davidovich A, Bausch J. Genetic toxicity studies with genistein. Food Chem Toxicol. 2006 January; 44(1):42-55. PubMed PMID: 16198038.
132. McClain M R, Wolz E, Davidovich A, Pfannkuch F, Bausch J. Subchronic and chronic safety studies with genistein in dogs. Food Chem Toxicol. 2005 October; 43(10):1461-82. PubMed PMID:15885867.
133. McClain M R, Wolz E, Davidovich A, Pfannkuch F, Edwards J A, Bausch J. Acute, subchronic and chronic safety studies with genistein in rats. Food Chem Toxicol. 2006 January; 44(1):56-80. PubMed PMID:16213646.
134. Messing E, Gee J R, Saltzstein D R, Kim K, diSant'Agnese A, Kolesar J, Harris L, Faerber A, Havighurst T, Young J M, Efros M, Getzenberg R H, Wheeler M A, Tangrea J, Parnes H, House M, Busby J E, Hohl R, Bailey H. A phase 2 cancer chemoprevention biomarker trial of isoflavone G-2535 (genistein) in presurgical bladder cancer patients. Cancer Prev Res (Phila). 2012 April; 5(4):621-30. PubMed PMID:22293631.
135. Record I R, Broadbent J L, King R A, Dreosti I E, Head R J, Tonkin A L. Genistein inhibits growth of B16 melanoma cells in vivo and in vitro and promotes differentiation in vitro. Int J Cancer. 1997 Sep. 4; 72(5):860-4. PubMed PMID:9311605.
136. Rozman K K, Bhatia J, Calafat A M, Chambers C, Culty M, Etzel R A, Flaws J A, Hansen D K, Hoyer P B, Jeffery E H, Kesner J S, Marty S, Thomas J A, Umbach D. NTP-CERHR expert panel report on the reproductive and developmental toxicity of genistein. Birth Defects Res B Dev Reprod Toxicol. 2006 December; 77(6):485-638. Review. PubMed PMID:17186522.
137. Taylor C K, Levy R M, Elliott J C, Burnett B P. The effect of genistein aglycone on cancer and cancer risk: a review of in vitro, preclinical, and clinical studies. Nutr Rev. 2009 July; 67(7):398-415. PubMed PMID: 19566600.
138. Cremer D R, Rabeler R, Roberts A, Lynch B. Long-term safety of alpha-lipoic acid (ALA) consumption: A 2-year study. Regul Toxicol Pharmacol. 2006 December; 46(3):193-201. PubMed PMID: 16899332.
139. Cremer D R, Rabeler R, Roberts A, Lynch B. Safety evaluation of alpha-lipoic acid (ALA). Regul Toxicol Pharmacol. 2006 October; 46(1):29-41. PubMed PMID: 16904799.
140. Foster T S. Efficacy and safety of alpha-lipoic acid supplementation in the treatment of symptomatic diabetic neuropathy. Diabetes Educ. 2007 January-February; 33(1):111-7. PubMed PMID: 17272797.
141. Guais A, Baronzio G, Sanders E, Campion F, Mainini C, Fiorentini G, Montagnani F, Behzadi M, Schwartz L, Abolhassani M. Adding a combination of hydroxycitrate and lipoic acid (METABLOC™) to chemotherapy improves effectiveness against tumor development: experimental results and case report. Invest New Drugs. 2012 February; 30(1):200-11. PubMed PMID: 20931262.
142. Korotchkina L G, Sidhu S, Patel M S. R-lipoic acid inhibits mammalian pyruvate dehydrogenase kinase. Free Radic Res. 2004 October; 38(10):1083-92. PubMed PMID:15512796.
143. Schwartz L, Abolhassani M, Guais A, Sanders E, Steyaert J M, Campion F, Israël M. A combination of alpha lipoic acid and calcium hydroxycitrate is efficient against mouse cancer models: preliminary results. Oncol Rep. 2010 May; 23(5):1407-16. PubMed PMID: 20372858.
144. Schwartz L, Guais A, Israel M, Junod B, Steyaert J M, Crespi E, Baronzio G, Abolhassani M. Tumor regression with a combination of drugs interfering with the tumor metabolism: efficacy of hydroxycitrate, lipoic acid and capsaicin. Invest New Drugs. 2013 April; 31(2):256-64. PubMed PMID:22797854.
145. Shay K P, Moreau R F, Smith E J, Smith A R, Hagen™. Alpha-lipoic acid as a dietary supplement: Molecular 146. Jones S E, Savin M A, Holmes F A, O'Shaughnessy J A, Blum J L, Vukelja S, McIntyre K J, Pippen J E, Bordelon J H, Kirby R, Sandbach J, Hyman W J, Khandelwal P, Negron A G, Richards D A, Anthony S P, Mennel R G, Boehm K A, Meyer W G, Asmar L. Phase III trial comparing doxorubicin plus cyclophosphamide with docetaxel plus cyclophosphamide as adjuvant therapy for operable breast cancer. J Clin Oncol. 2006 Dec. 1; 24(34):5381-7. Erratum in: J Clin Oncol. 2007 May 1; 25(13):1819. PMID: 17135639.
147. Hudis, C; Cancer and Leukemia Group B. Phase III Comparison of Adjuvant Chemotherapy W/High-Dose Cyclophosphamide Plus Doxorubicin (AC) vs Sequential Doxorubicin Fol by Cyclophosphamide (A-C) in High Risk Breast Cancer Patients With 0-3 Positive Nodes (Intergroup, CALGB 9394) IN: ClinicalTrials.gov [Internet]. Bethesda (Md.): National Library of Medicine (US). 2000-[2011 Feb. 23]. Available from http://clinical-trials.gov/ct2/show/ NCT00590785?term=NCT00590785: NCT00590785.
148. Goodwin P J, Stambolic V, Lemieux J, Chen B E, Parulekar W R, Gelmon K A, Hershman D L, Hobday T J, Ligibel J A, Mayer I A, Pritchard K I, Whelan T J, Rastogi P, Shepherd L E. Evaluation of metformin in early breast cancer: a modification of the traditional paradigm for clinical testing of anti-cancer agents. Breast Cancer Res Treat. 2011 February; 126(1):215-20. doi: 10.1007/s10549-010-1224-1. Epub 2010 Oct. 26. Review. PMID: 20976543. ClinicalTrials.gov Identifier: NCT01101438.
149. Seely A J, Seely D; Ottowa Hospital. Adjuvent Melatonin for Prevention of Lung Cancer Recurrence and Mortality (AMPLCaRe). IN: ClinicalTrials.gov [Internet]. Bethesda (Md.): National Library of Medicine (US). 2000-[2011 Feb. 23]. Available from http://clinical-trials.gov/ct2/show/ NCT00668707?term=NCT00668707: NCT00668707.
150. Kanai M, Yoshimura K, Asada M, Imaizumi A, Suzuki C, Matsumoto S, Nishimura T, Mori Y, Masui T, Kawaguchi Y, Yanagihara K, Yazumi S, Chiba T, Guha S, Aggarwal B B. A phase I/II study of gemcitabine-based chemotherapy plus curcumin for patients with gemcitabine-resistant pancreatic cancer. Cancer Chemother Pharmacol. 2011 July; 68(1):157-64. doi: 10.1007/s00280-010-1470-2. Epub 2010 Sep. 22. PubMed PMID: 20859741
151. Dhillon N, Aggarwal B B, Newman R A, Wolff R A, Kunnumakkara A B, Abbruzzese J L, Ng C S, Badmaev V, Kurzrock R. Phase II trial of curcumin in patients with advanced pancreatic cancer. Clin Cancer Res. 2008 July 15; 14(14):4491-9. PubMed PMID: 18628464
152. Peters K; Brain Tumor Fund for the Carolinas. Low-Dose Naltrexone for Glioma Patients. IN: ClinicalTrials.gov [Internet]. Bethesda (Md.): National Library of Medicine (US). 2000-[2011 Feb. 23]. Available from http://clinicaltrials.gov/ct2/show/NCT01303835: NCT01303835.
153. Constantinou, M; Brown University. Low Dose Naltrexone for Metastatic Melanoma, Castrate Resistant Prostate Cancer and Renal Cancer. IN: ClinicalTrials.gov [Internet]. Bethesda (Md.): National Library of Medicine (US). 2000-[2012 Jul. 24]. Available from http://clinical-trials.gov/ct2/show/NCT01650350: NCT01650350.
154. Lazarevic B, Boezelijn G, Diep L M, Kvernrod K, Ogren O, Ramberg H, Moen A, Wessel N, Berg R E, Egge-Jacobsen W, Hammarstrom C, Svindland A, Kucuk O, Saatcioglu F, Taskén K A, Karlsen S J. Efficacy and safety of short-term genistein intervention in patients with localized prostate cancer prior to radical prostatectomy: a randomized, placebo-controlled, double-blind Phase 2 clinical trial. Nutr Cancer. 2011; 63(6):889-98. doi: 10.1080/01635581.2011.582221. Epub 2011 Jun. 29. PMID: 21714686
155. University of Toronto. ALA and Prostate Cancer. IN: ClinicalTrials.gov [Internet]. Bethesda (Md.): National Library of Medicine (US). 2000-[2006 Mar. 29]. Available from http://clinicaltrials.gov/ct2/show/ NCT00309439: NCT00309439.

All patents, applications, and publications cited in the text above are incorporated herein by reference.

EQUIVALENTS

Other variations and embodiments of the invention described herein will now be apparent to those of skill in the art without departing from the disclosure of the invention or the coverage of the claims to follow.

The invention claimed is:

1. A method of treating late stage ovarian cancer by orally administering at least seven agents to a subject whose cancer is at least stage II, wherein the at least seven agents include a regimen comprising a combination of:
   metronomic 50 mg/day cyclophosphamide,
   metformin dosed within a range of 500-1000 mg/day,
   alpha-lipoic acid dosed at 1200 mg/day,
   curcumin dosed within a range of 750-4500 mg/day;
   genistein dosed at 500 mg/day,
   melatonin dosed at 10 mg/day, and
   naltrexone at a low dose within a range of 1.5-4.5 mg/day.

2. The method of claim 1, wherein the ovarian cancer has metastasized.

3. The method of claim 1, wherein each of the agents is administered in doses well below the maximum tolerated dose for the agent.

4. The method of claim 1, wherein the ovarian cancer is terminal cancer.

5. The method of claim 1, wherein the ovarian cancer has relapsed after treatment with another therapeutic modality.

6. The method of claim 1, wherein the ovarian cancer comprises one or more solid tumors.

7. A combination comprising:
   at least one oral dose of metformin, within a range of 500-1000 mg;
   at least one oral 50 mg dose of cyclophosphamide,
   at least one oral 1200 mg dose of alpha-lipoic acid,
   at least one oral dose of curcumin, in an amount of 750-4500 mg/day;
   at least one oral dose of genistein at 500 mg/day,
   at least one oral 10 mg dose of melatonin, and
   at least one oral dose of naltrexone within a range of 1.5-4.5 mg/day.

8. The method of claim 3, wherein each of the agents is administered at a non-toxic dose, orally and chronically.

* * * * *